(12) United States Patent
Shin et al.

(10) Patent No.: US 11,362,281 B2
(45) Date of Patent: Jun. 14, 2022

(54) COMPOUND FOR ORGANIC OPTOELECTRONIC DIODE, COMPOSITION FOR ORGANIC OPTOELECTRONIC DIODE, ORGANIC OPTOELECTRONIC DIODE, AND DISPLAY APPARATUS

(71) Applicants: SAMSUNG SDI CO., LTD., Yongin-si (KR); SAMSUNG ELECTRONICS CO., LTD., Suwon-si (KR)

(72) Inventors: Chang Ju Shin, Suwon-si (KR); Jaejin Oh, Suwon-si (KR); Eun Sun Yu, Suwon-si (KR); Hanill Lee, Suwon-si (KR); Sung-Hyun Jung, Suwon-si (KR); Ho Kuk Jung, Suwon-si (KR); Sujin Han, Suwon-si (KR)

(73) Assignees: SAMSUNG SDI CO., LTD., Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 407 days.

(21) Appl. No.: 16/336,955

(22) PCT Filed: May 24, 2017

(86) PCT No.: PCT/KR2017/005410
§ 371 (c)(1),
(2) Date: Mar. 27, 2019

(87) PCT Pub. No.: WO2018/062659
PCT Pub. Date: Apr. 5, 2018

(65) Prior Publication Data
US 2019/0267552 A1 Aug. 29, 2019

(30) Foreign Application Priority Data
Sep. 29, 2016 (KR) .................. 10-2016-0125669

(51) Int. Cl.
*H01L 51/00* (2006.01)
*C07D 405/10* (2006.01)
(Continued)

(52) U.S. Cl.
CPC ........ *H01L 51/0067* (2013.01); *C07D 307/77* (2013.01); *C07D 405/10* (2013.01);
(Continued)

(58) Field of Classification Search
CPC .. C07D 307/77; C07D 405/10; C07D 405/14; C07D 409/10; C07D 409/14;
(Continued)

(56) References Cited

U.S. PATENT DOCUMENTS

| 7,651,761 B2 | 1/2010 | Shimomura et al. |
| 2012/0126208 A1* | 5/2012 | Kawamura ......... H01L 51/0072 257/40 |

(Continued)

FOREIGN PATENT DOCUMENTS

| CN | 103058987 A | 4/2013 |
| CN | 104364344 A | 2/2015 |

(Continued)

OTHER PUBLICATIONS

Machine translation of KR 20160107669 A (publication date: Sep. 2016). (Year: 2016).*

(Continued)

*Primary Examiner* — Dawn L Garrett
(74) *Attorney, Agent, or Firm* — Lee IP Law, P.C.

(57) ABSTRACT

Disclosed are a compound for an organic optoelectronic diode, the compound expressed by Chemical Formula 1, a composition for an organic optoelectronic diode, an organic (Continued)

optoelectronic diode utilizing same, a display apparatus. The specific content of Chemical Formula 1 is defined in the specification.

17 Claims, 1 Drawing Sheet

(51) Int. Cl.
*C07D 405/14* (2006.01)
*C07D 409/10* (2006.01)
*C07D 409/14* (2006.01)
*H01L 51/50* (2006.01)
*C07D 307/77* (2006.01)
*C09K 11/06* (2006.01)

(52) U.S. Cl.
CPC ......... *C07D 405/14* (2013.01); *C07D 409/10* (2013.01); *C07D 409/14* (2013.01); *C09K 11/06* (2013.01); *H01L 51/00* (2013.01); *H01L 51/0058* (2013.01); *H01L 51/0073* (2013.01); *H01L 51/0074* (2013.01); *H01L 51/50* (2013.01); *H01L 51/5012* (2013.01); *H01L 51/5072* (2013.01)

(58) Field of Classification Search
CPC . C09K 11/06; H01L 2251/5384; H01L 51/00; H01L 51/0058; H01L 51/0067; H01L 51/0072; H01L 51/0073; H01L 51/0074; H01L 51/50; H01L 51/5012; H01L 51/5016; H01L 51/5072
See application file for complete search history.

(56) References Cited

U.S. PATENT DOCUMENTS

2016/0093808 A1    3/2016  Adamovich et al.
2017/0207396 A1*   7/2017  Park .................... H01L 51/0067
2018/0351113 A1*  12/2018  Ahn ..................... H01L 51/0074

FOREIGN PATENT DOCUMENTS

| CN | 104638202 A | 5/2015 |
| CN | 105377822 A | 3/2016 |
| JP | 2001-043979 A | 2/2001 |
| JP | 2011-029220 A | 2/2011 |
| KR | 10-2008-0080306 A | 9/2008 |
| KR | 10-1120917 B1 | 1/2012 |
| KR | 10-2013-0042901 A | 4/2013 |
| KR | 10-2015-0007139 A | 1/2015 |
| KR | 10-2015-0129606 A | 11/2015 |
| KR | 10-2016-0030003 A | 3/2016 |
| KR | 10-2016-0046703 A | 4/2016 |
| KR | 10-2016-0076461 A | 6/2016 |
| KR | 10-2016-0079548 A | 7/2016 |
| KR | 10-2016-0080307 A | 7/2016 |
| KR | 10-2016-0085603 A | 7/2016 |
| KR | 10-2016-0107669 A | 9/2016 |
| KR | 20170097450 A * | 8/2017 |
| WO | WO 2016/084962 A1 * | 6/2016 |

OTHER PUBLICATIONS

Machine translation of KR 20130042901 A (publication date: Apr. 2013). (Year: 2013).*
S. Wise, et al., "Effect of C18 Surface Coverage on Selectivity in Reversed-Phase Liquid Chromatography of Polycyclic Aromatic Hydrocarbons", Anal. Chem., 1983, 55, pp. 1479-1485.
International Search Report for PCT/KR2017/005410 filed May 24, 2017.

* cited by examiner

【Figure 1】
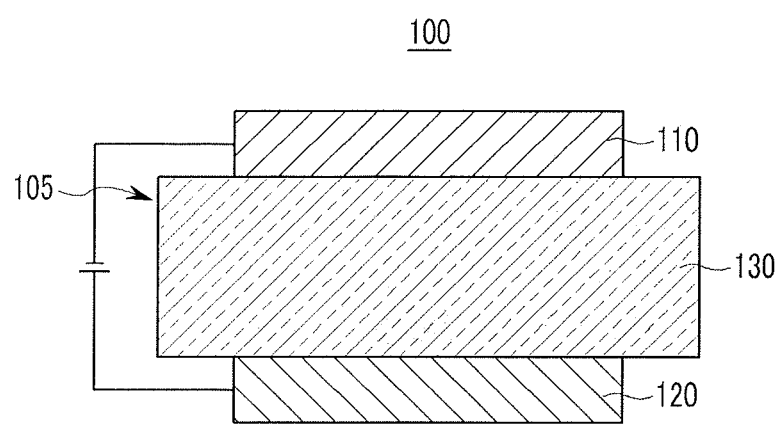
【Figure 2】
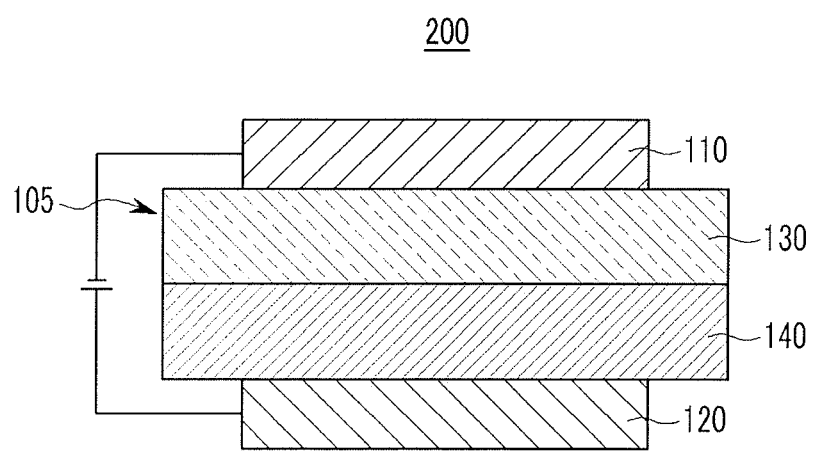

COMPOUND FOR ORGANIC OPTOELECTRONIC DIODE, COMPOSITION FOR ORGANIC OPTOELECTRONIC DIODE, ORGANIC OPTOELECTRONIC DIODE, AND DISPLAY APPARATUS

CROSS-REFERENCE TO THE RELATED APPLICATION

This is the U.S. national phase application based on PCT Application No. PCT/KR2017/005410, filed May 24, 2017, which is based on Korean Patent Application No. 10-2016-0125669, filed Sep. 29, 2016, the entire contents of all of which are hereby incorporated by reference.

TECHNICAL FIELD

A compound for an organic optoelectronic diode, a composition for an organic optoelectronic diode, an organic optoelectronic diode, and a display apparatus are disclosed.

BACKGROUND ART

An organic optoelectronic diode is a diode that converts electrical energy into photoenergy, and vice versa.

An organic optoelectronic diode may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic diode may be an organic photoelectric diode, an organic light emitting diode, an organic solar cell, and an organic photo conductor drum.

Of these, an organic light emitting diode (OLED) has recently drawn attention due to an increase in demand for flat panel displays. The organic light emitting diode is a diode converting electrical energy into light by applying a current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic diode capable of realizing high efficiency and long life-span organic optoelectronic diode.

Technical Solution

Another embodiment provides a composition for an organic optoelectronic diode including the compound for an organic optoelectronic diode.

Yet another embodiment provides an organic optoelectronic diode including the compound.

Still another embodiment provides a display apparatus including the organic optoelectronic diode.

According to an embodiment, a compound for an organic optoelectronic diode represented by Chemical Formula 1 is provided.

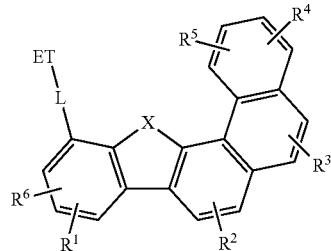

[Chemical Formula 1]

In Chemical Formula 1,

ET is an N-containing substituted or unsubstituted C2 to C30 heterocyclic group except a carbazolyl group, L is a single bond, a substituted or unsubstituted C6 to C20 arylene group, or a substituted or unsubstituted C2 to C30 heteroarylene group, X is O or S, and $R^1$ to $R^6$ are independently hydrogen, deuterium, a substituted or unsubstituted C1 to C10 alkyl group, or a substituted or unsubstituted C6 to C18 aryl group, wherein the "substituted" refers to replacement of at least one hydrogen by deuterium, a cyano group, a C1 to C20 alkyl group, a C6 to C30 aryl group, or a C2 to C30 heteroaryl group.

According to another embodiment, a composition for an organic optoelectronic diode includes the aforementioned first compound for an organic optoelectronic diode; and a second compound for an organic optoelectronic diode represented by Chemical Formula 2.

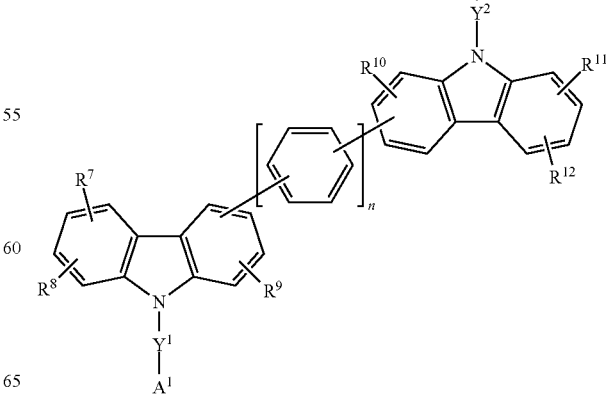

[Chemical Formula 2]

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $A^1$ and $A^2$ are independently a substituted or unsubstituted C6 to C30 aryl group, a substituted or unsubstituted C2 to C30 heterocyclic group, or a combination thereof, $R^7$ to $R^2$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, n is one of integers of 0 to 2; and the "substituted" refers to replacement of at least one hydrogen by deuterium, a C1 to C4 alkyl group, a C6 to C18 aryl group, or a C2 to C30 heteroaryl group.

According to another embodiment, an organic optoelectronic diode includes an anode and a cathode facing each other and at least one organic layer disposed between the anode and the cathode, wherein the organic layer includes the aforementioned compound for an organic optoelectronic diode, or the composition for an organic optoelectronic diode.

According to another embodiment, a display apparatus including the organic optoelectronic diode is provided.

Advantageous Effects

An organic optoelectronic diode having high efficiency and a long life-span may be realized.

DESCRIPTION OF THE DRAWINGS

FIGS. 1 and 2 are cross-sectional views showing organic light emitting diodes according to embodiments.

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a quinazolinyl group, a dibenzofuranyl group, a dibenzothiophenyl group, or a carbazolyl group. In addition, in specific examples of the present invention, the "substituted" refers to replacement of at least one hydrogen of a substituent or a compound by deuterium, a C1 to C5 alkyl group, a C6 to C18 aryl group, a pyridinyl group, a quinazolinyl group, a dibenzofuranyl group, or a dibenzothiophenyl group. In addition, in specific examples of the present invention, the "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a fluorenyl group, a pyridinyl group, a quinazolinyl group, a carbazolyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may include a pyridinyl group, a pyrimidinyl group, a pyrazinyl group, a pyridazinyl group, a triazinyl group, a quinolinyl group, an isoquinolinyl group, a quinazolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted benzoquinolinyl group, a substituted or unsubstituted benzoisoquinolinyl group, a substituted or unsubstituted benzoquinazolinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic diode according to an embodiment is described.

A compound for an organic optoelectronic diode according to an embodiment is represented by Chemical Formula 1.

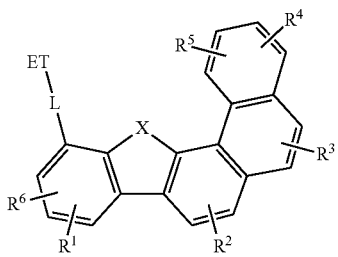

[Chemical Formula 1]

In Chemical Formula 1,

ET is an N-containing substituted or unsubstituted C2 to C30 heterocyclic group except a carbazolyl group, L is a single bond, a substituted or unsubstituted C6 to C20 arylene group, or a substituted or unsubstituted C2 to C30 heteroarylene group, X is O or S, and $R^1$ to $R^6$ are independently hydrogen, deuterium, a substituted or unsubstituted C1 to C10 alkyl group, or a substituted or unsubstituted C6 to C18 aryl group, wherein the "substituted" refers to replacement of at least one hydrogen by deuterium, a cyano group, a C1 to C20 alkyl group, a C6 to C30 aryl group, or a C2 to C30 heteroaryl group.

In one example of the present invention, the "substituted" refers to replacement of at least one hydrogen by deuterium, a phenyl group, a biphenyl group, a terphenyl group, a naphthyl group, a fluorenyl group, a carbazolyl group, a dibenzofuranyl group, or a dibenzothiophenyl group.

The compound for an organic optoelectronic diode according to the present invention may increase stability of the compound in a process and prevent degradation thereof when applied to a diode because naphthalene is fused to dibenzofuran or dibenzothiophene to increase a glass transition temperature (Tg). The glass transition temperature (Tg) may be related to thermal stability of the compound and the diode to which it is applied. That is, when the compound for an organic optoelectronic diode having a high glass transition temperature (Tg) is applied as a thin film to an organic light emitting diode, it may be prevented from being degraded by temperatures in subsequent processes such as an encapsulation process after the compound for an organic optoelectronic diode is deposited and thus life-span characteristics of the compound and the diode may be ensured.

On the other hand, when the substituent represented by ET is substituted in the direction in which naphthalene is not fused, an effect of increasing T1 energy value may be obtained. As a result, an organic light emitting diode with high efficiency may be produced. These effects are particularly exhibited in a green light emitting diodes.

In addition, since a polar group of the nitrogen included in the ET unit may interact with the electrode, charge injection is easy and mobility is high so that a low driving voltage may be realized.

That is, by applying a compound for an organic optoelectronic diode according to the present invention, a long life-span, low driving, and high efficiency diode may be realized.

ET of Chemical Formula 1 may be an N-containing substituted or unsubstituted C2 to C30 heterocyclic group except a carbazolyl group and Chemical Formula 1 may be for example represented by Chemical Formula 1A.

[Chemical Formula 1A]

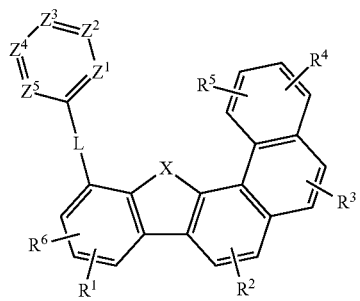

In Chemical Formula 1A, $Z^1$ to $Z^5$ are independently N or $CR^a$, wherein at least one of $Z^1$ to $Z^5$ is N and $R^a$ is independently hydrogen, deuterium, a substituted or unsubstituted C1 to C10 alkyl group, a substituted or unsubstituted C6 to C18 aryl group, or a substituted or unsubstituted C2 to C20 heterocyclic group, and $R^a$ is independently present or adjacent groups thereof are linked with each other to form a substituted or unsubstituted aliphatic, aromatic, or heteroaromatic monocyclic or polycyclic ring.

In one example of the present invention, two or three of $Z^1$ to $Z^5$ in Chemical Formula 1A may be N, when $Z^1$ to $Z^5$ are $CR^a$, $R^a$ may independently be selected from hydrogen, deuterium, a phenyl group, a naphthyl group, a terphenyl group, a biphenyl group, a triphenylene group, a fluorenyl group, a dibenzofuranyl group, and a dibenzothiophenyl group.

L, X, and $R^1$ to $R^6$ may be the same as described above.

In an embodiment of the present invention, when $R^a$ is independently present, ET may be a substituted or unsubstituted pyridinyl group, a substituted or unsubstituted pyrimidinyl group, a substituted or unsubstituted triazinyl group, a substituted or unsubstituted pyrazinyl group, or a substituted or unsubstituted pyridazinyl group.

When adjacent groups of $R^a$ are linked with each other to form a substituted or unsubstituted aliphatic, aromatic, or heteroaromatic monocyclic or polycyclic ring, ET may be a substituted or unsubstituted quinolinyl group, a substituted or unsubstituted isoquinolinyl group, a substituted or unsubstituted quinazolinyl group, a substituted or unsubstituted benzofuranpyridinyl group, a substituted or unsubstituted benzofuranpyrimidinyl group, a substituted or unsubstituted benzothiophenepyridinyl group, or a substituted or unsubstituted benzothiophenepyrimidinyl group, and in an embodiment of the present invention, ET may be selected from substituents of Group I.

[Group 1]

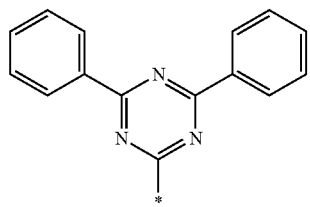

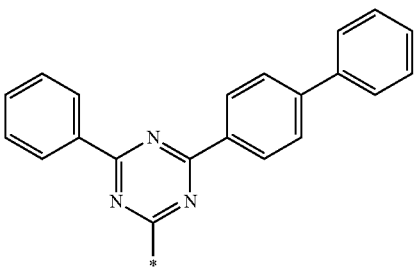

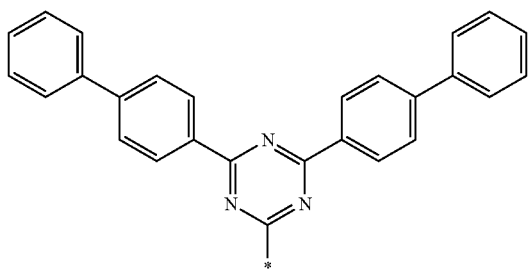

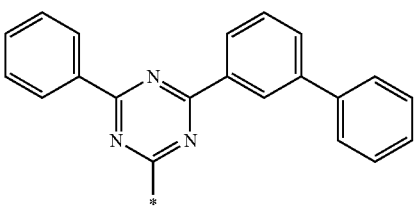

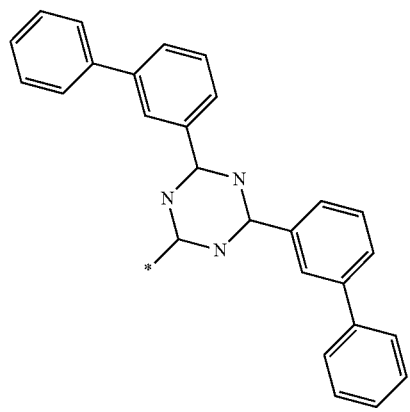

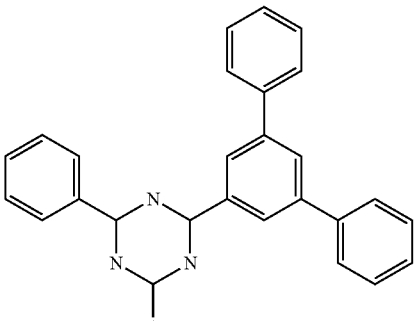

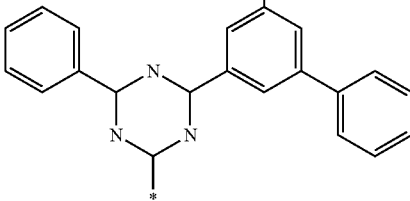

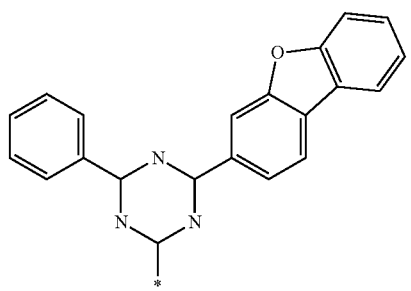
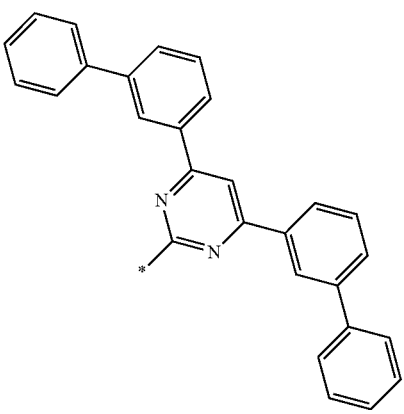
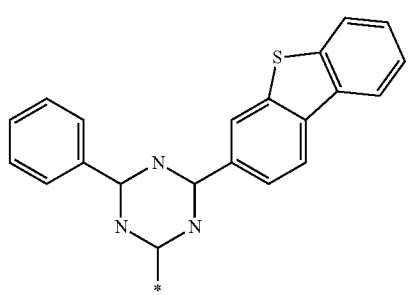
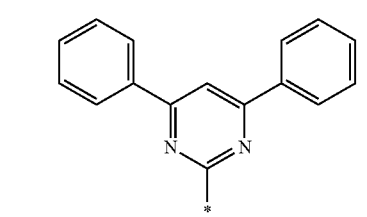
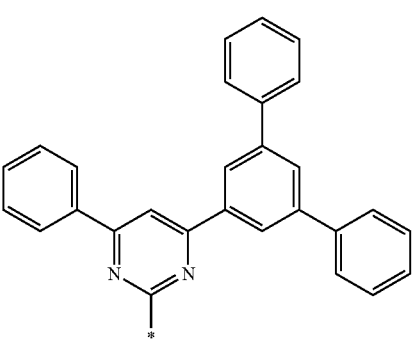
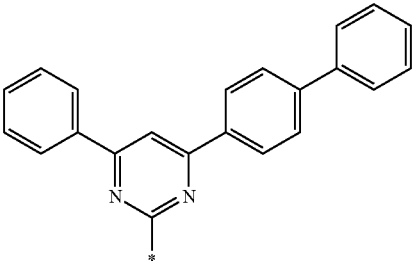
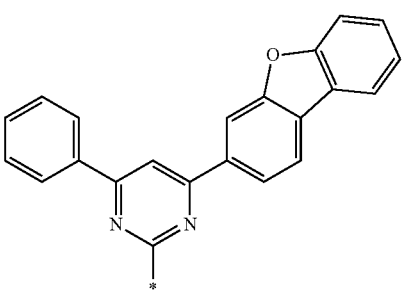
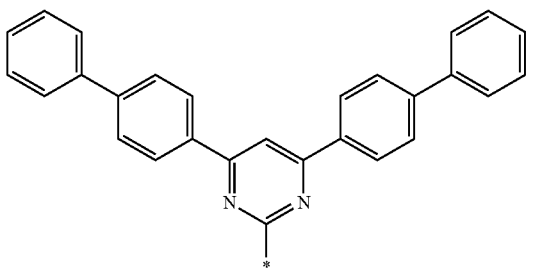
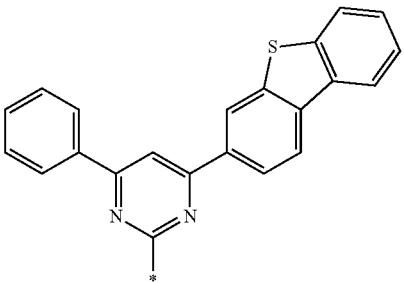
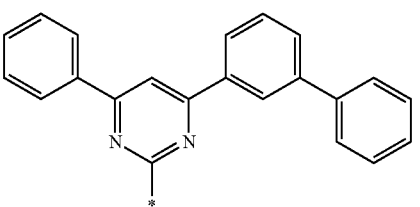
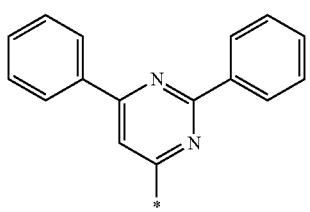

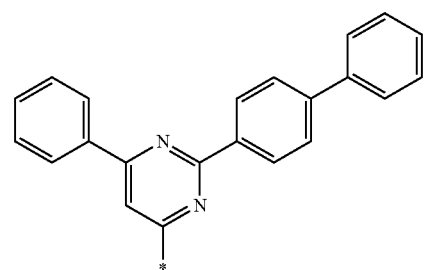
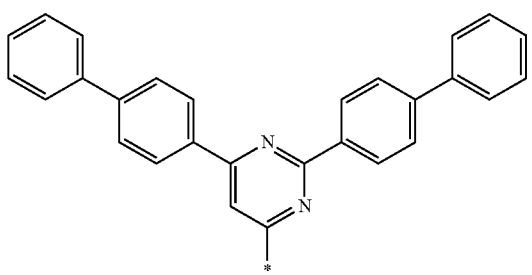
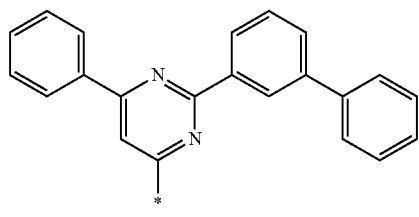
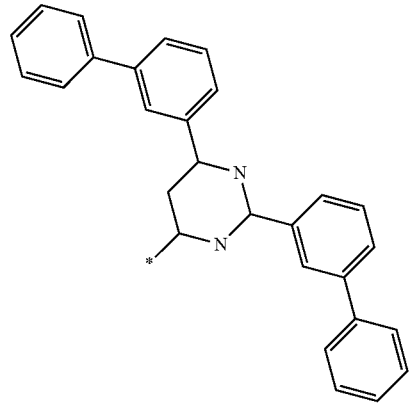
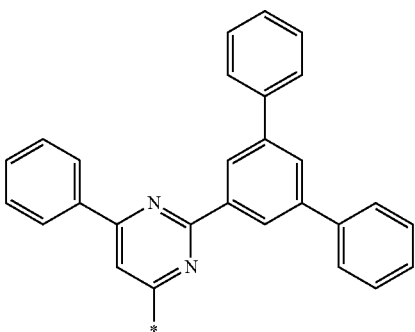
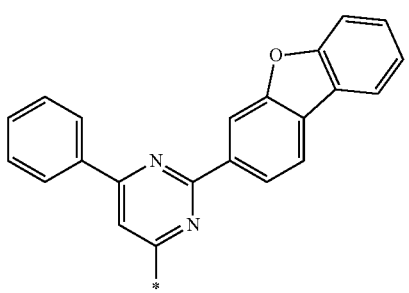
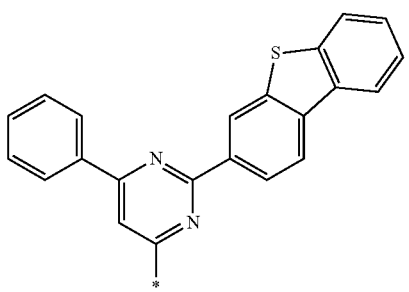
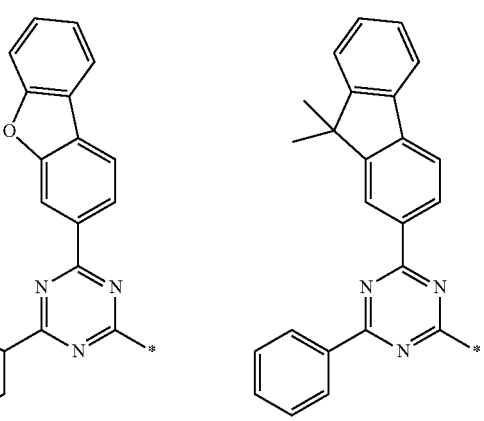
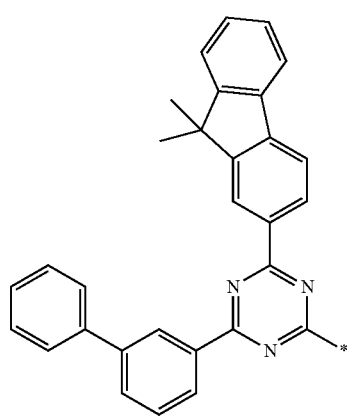

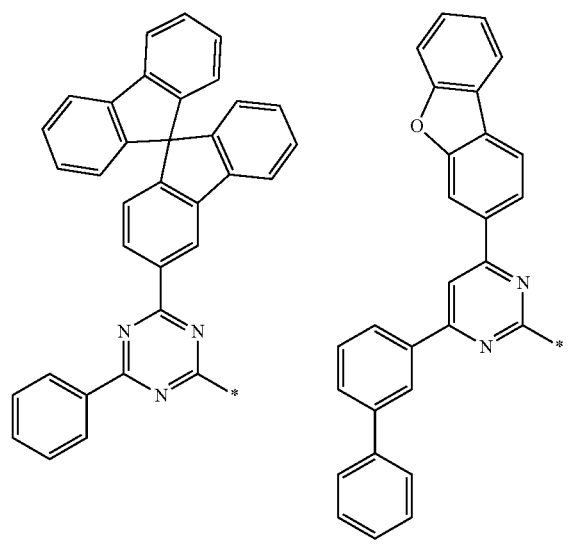
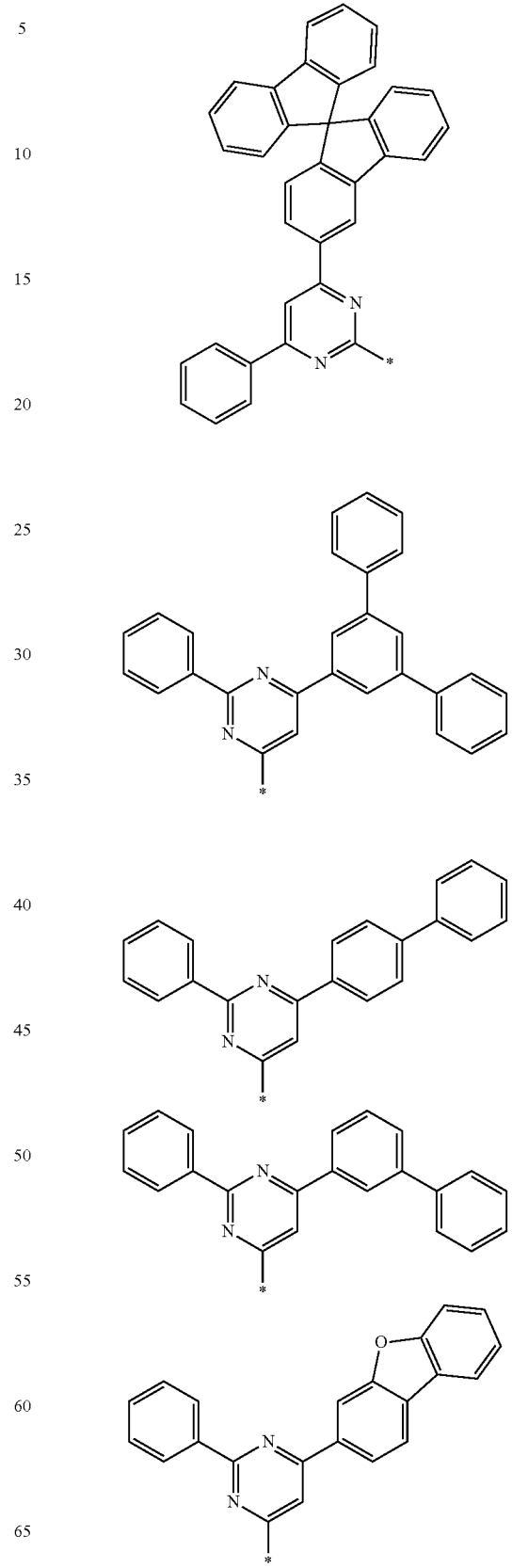

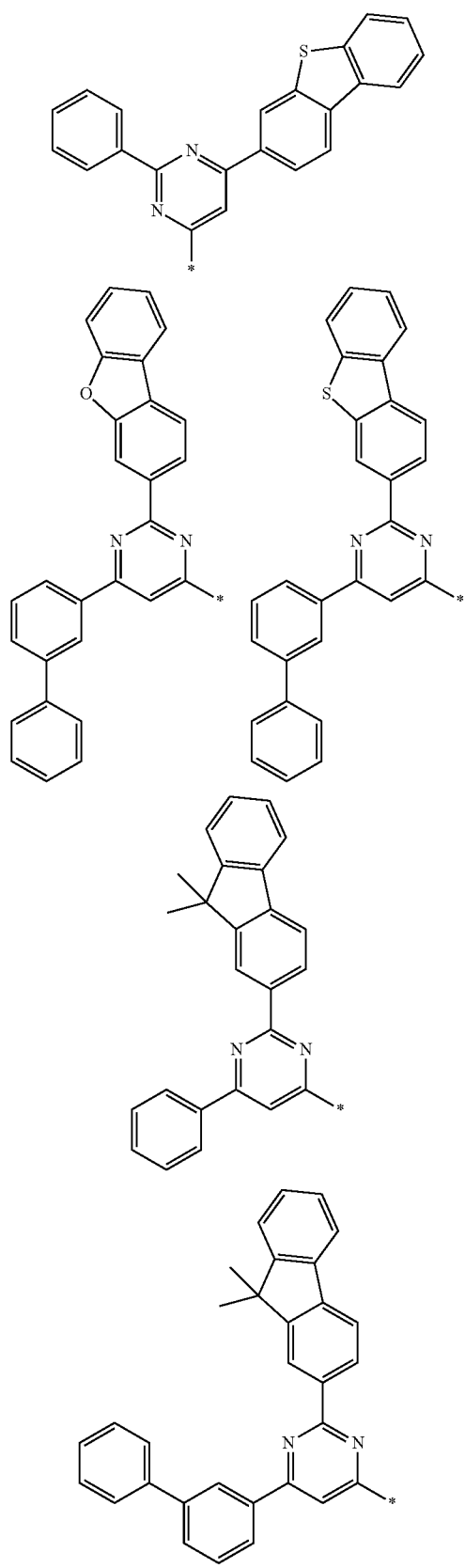
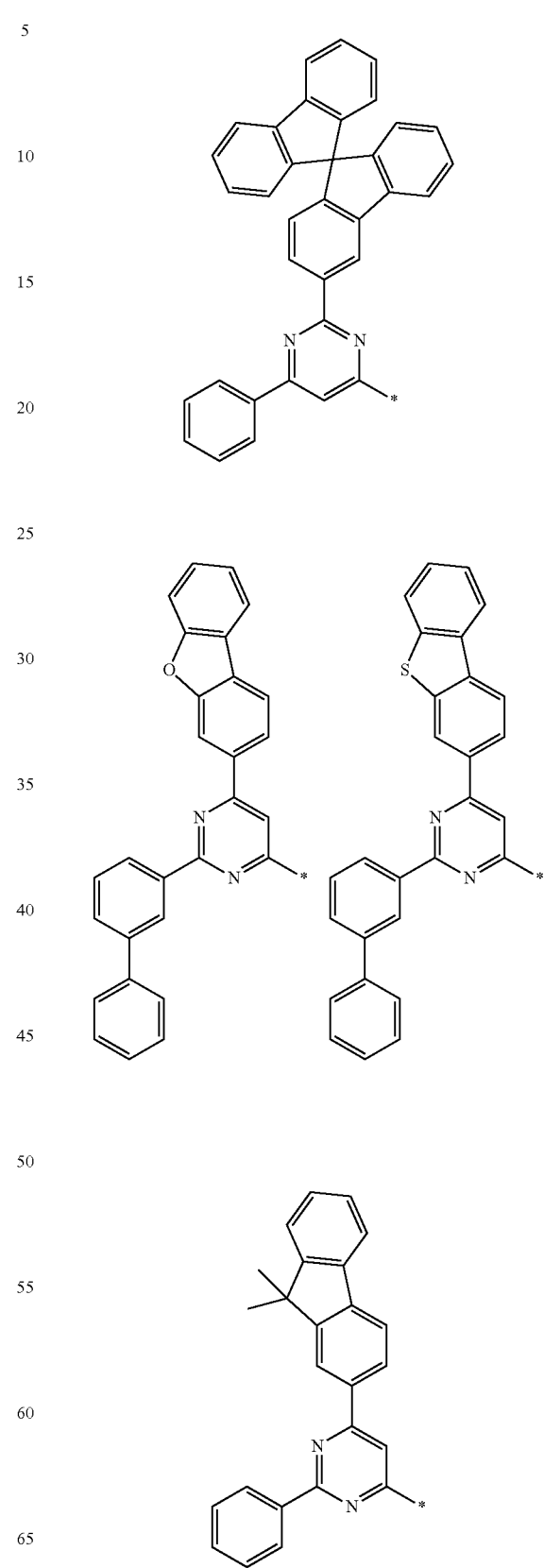

-continued

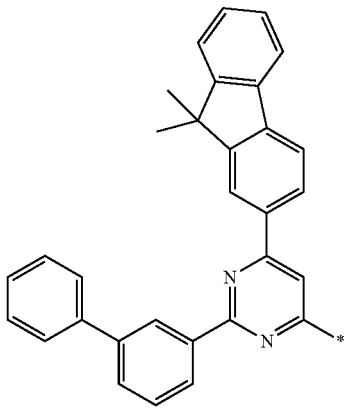

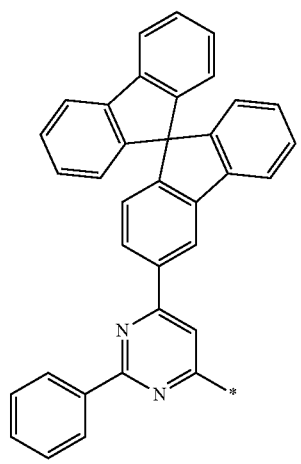

In Group I, * is a linking point with "L" of Chemical Formula 1.

In a specific embodiment of the present invention, the ET group may be a substituted or unsubstituted pyridinyl group, a substituted or unsubstituted pyrimidinyl group, or a substituted or unsubstituted triazinyl group, and in the most specific embodiment of the present invention, it may be a substituted or unsubstituted pyrimidinyl group, or a substituted or unsubstituted triazinyl group.

In an embodiment of the present invention, L may be a single bond, or a substituted or unsubstituted C6 to C20 arylene group and in a specific embodiment of the present invention, L may be a single bond, a substituted or unsubstituted phenylene group, or a substituted or unsubstituted biphenylene group.

When L is a substituted or unsubstituted phenylene group, Chemical Formula 1 may be for example represented by one of Chemical Formula 1A-I, Chemical Formula 1A-II, and Chemical Formula 1A-III.

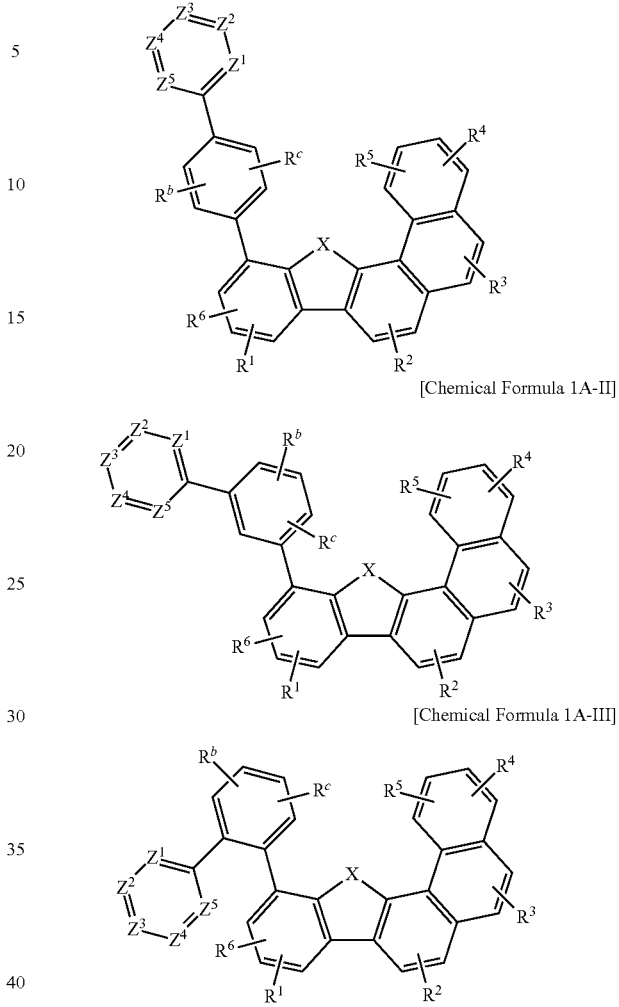

In Chemical Formula 1A-I, Chemical Formula 1A-II and Chemical Formula 1A-III, $R^b$ and $R^c$ are independently hydrogen, deuterium, a substituted or unsubstituted C1 to C10 alkyl group, or a substituted or unsubstituted C6 to C18 aryl group, to $Z^5$, X, and $R^1$ to $R^6$ are the same as described above.

In an embodiment of the present invention, $R^1$ to $R^p$ may independently be hydrogen, deuterium, a substituted or unsubstituted C1 to C5 alkyl group, or a substituted or unsubstituted C6 to C12 aryl group, in a specific embodiment, $R^1$ to $R^6$ may be hydrogen, deuterium, a substituted or unsubstituted C1 to C5 alkyl group, a substituted or unsubstituted phenyl group, a substituted or unsubstituted biphenyl group, or a substituted or unsubstituted naphthyl group, and in the most specific embodiment of the present invention, they may be all hydrogen.

In an embodiment of the present invention, $R^a$ may independently be hydrogen, deuterium, a substituted or unsubstituted C1 to C5 alkyl group, a substituted or unsubstituted C6 to C12 aryl group, or a substituted or unsubstituted C2 to C20 heterocyclic group, in a specific embodiment, it may be a substituted or unsubstituted C6 to C12 aryl group, or a substituted or unsubstituted C2 to C20 heterocyclic group, and in the most specific embodiment of the present invention, it may be a substituted or unsubstituted phenyl group, a substituted or unsubstituted biphenyl group, a substituted or unsubstituted terphenyl group, a substituted or unsubstituted fluorenyl group, a substituted or unsubstituted dibenzofuranyl group, or a substituted or unsubstituted dibenzothiophenyl group.

In an embodiment of the present invention, $R^b$ and $R^c$ may independently be hydrogen, deuterium, a substituted or unsubstituted C1 to C5 alkyl group, or a substituted or unsubstituted C6 to C12 aryl group, in a specific embodiment, they may be hydrogen, deuterium, a substituted or unsubstituted C1 to C5 alkyl group, a substituted or unsubstituted phenyl group, a substituted or unsubstituted biphenyl group, or a substituted or unsubstituted naphthyl group, and in the most specific embodiment of the present invention, they may be all hydrogen.

The compound for an organic optoelectronic diode represented by Chemical Formula 1 may be for example selected from compounds of Group 1, but is not limited thereto.

[Group 1]

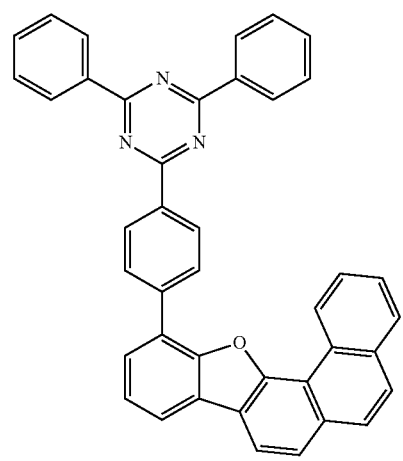

1

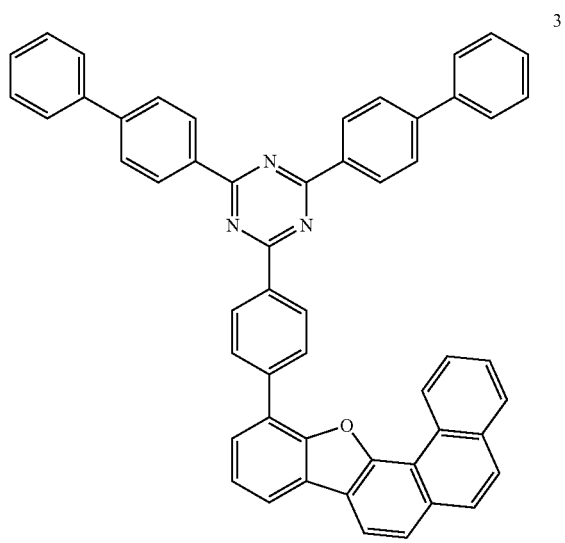

3

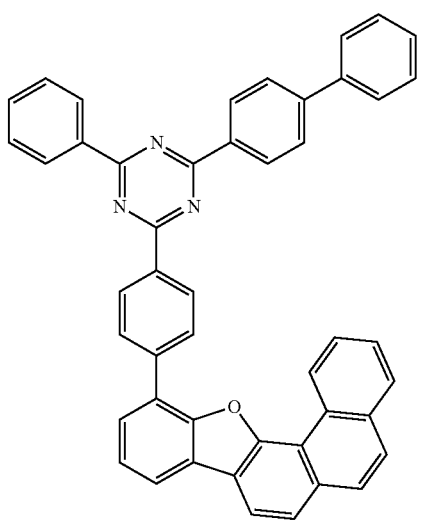

2

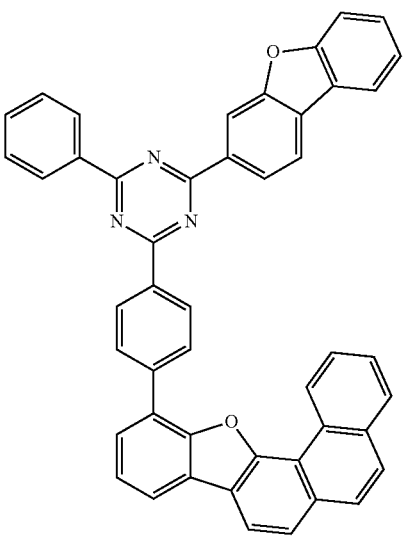

4

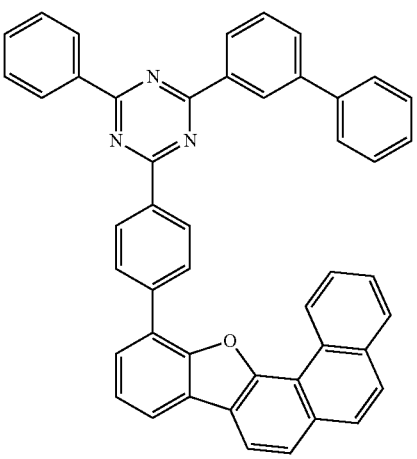

5

6
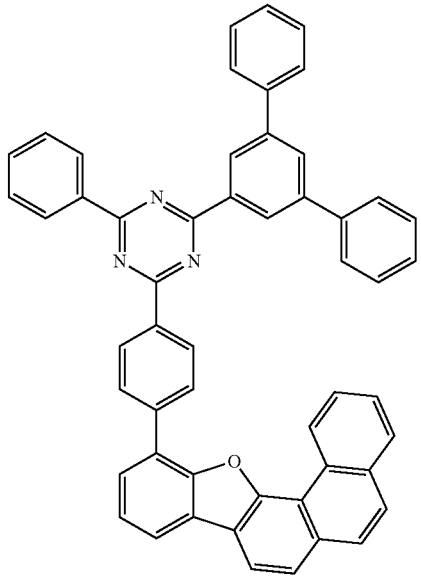
7
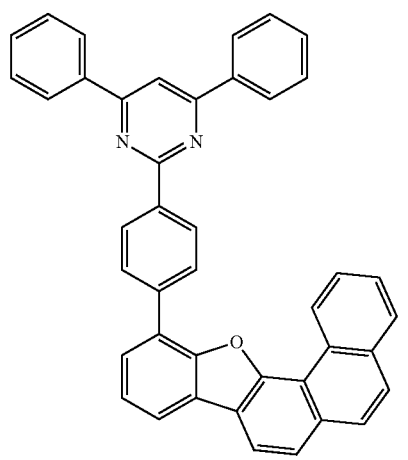
8
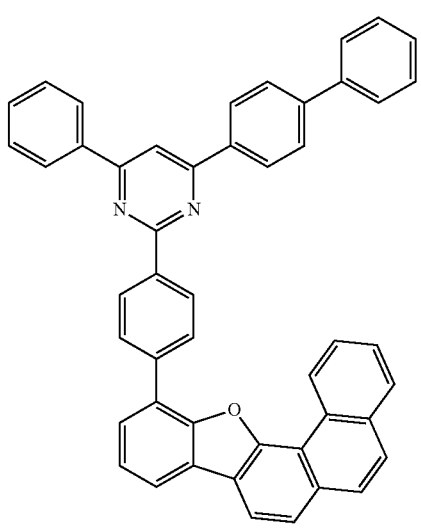
5
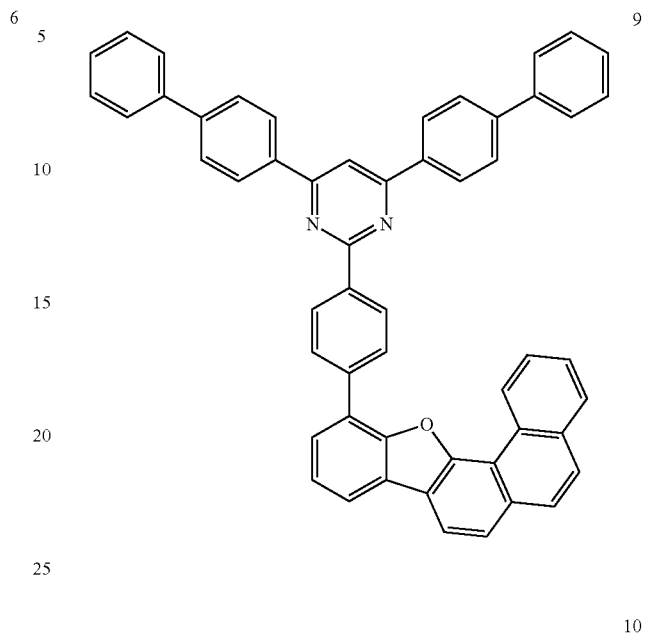
10
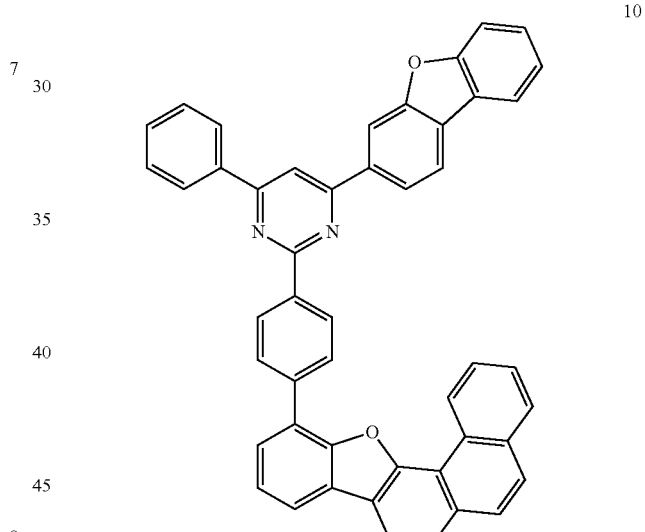
11
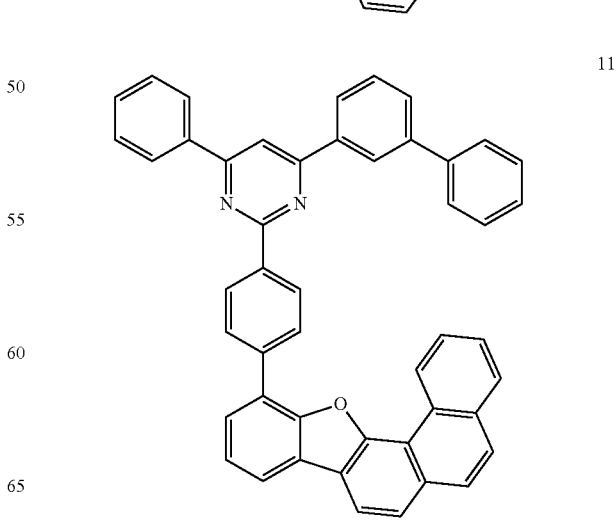

-continued
12
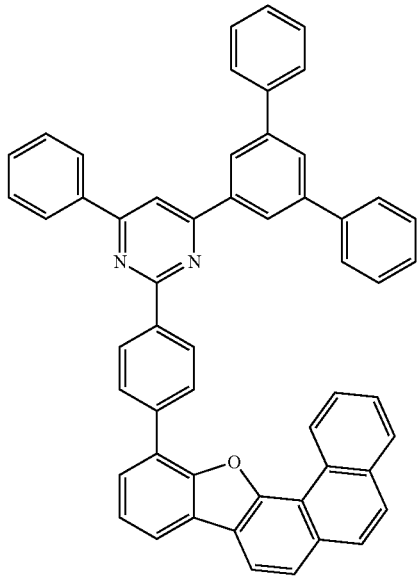
15
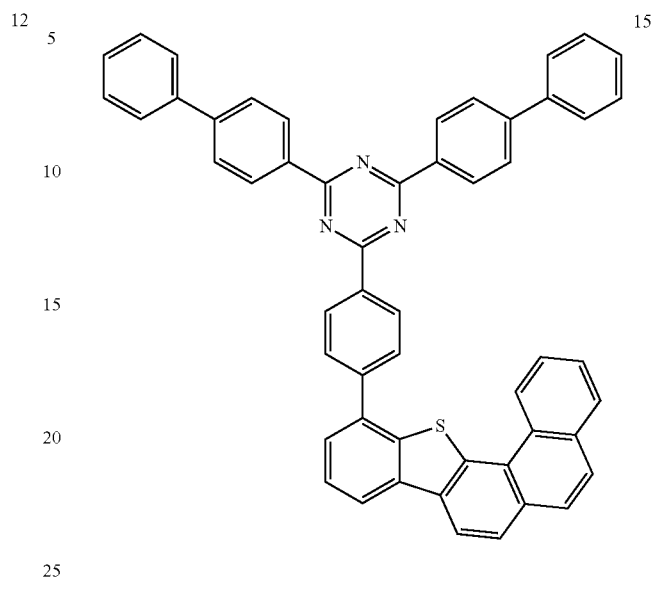
13
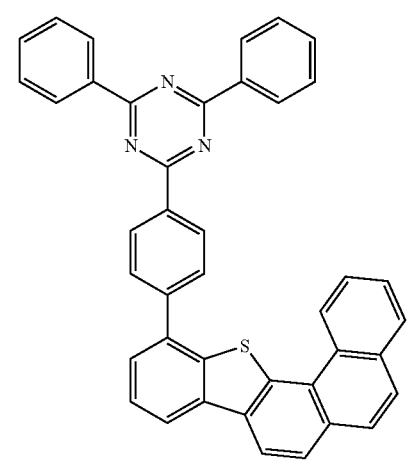
16
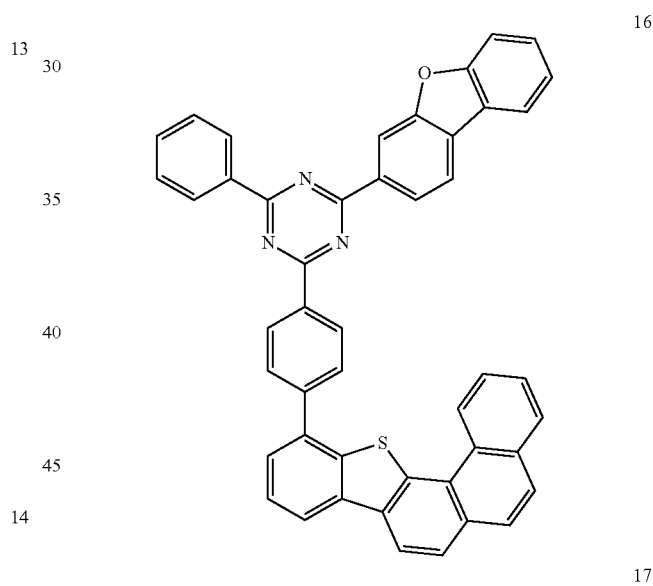
14
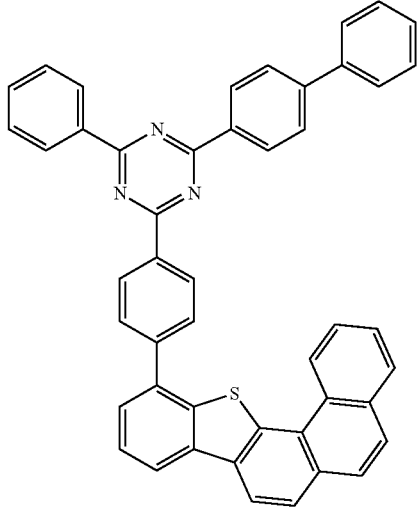
17
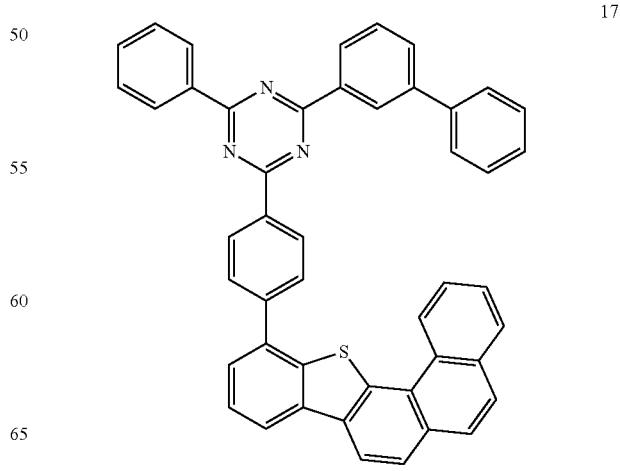

25
-continued
18
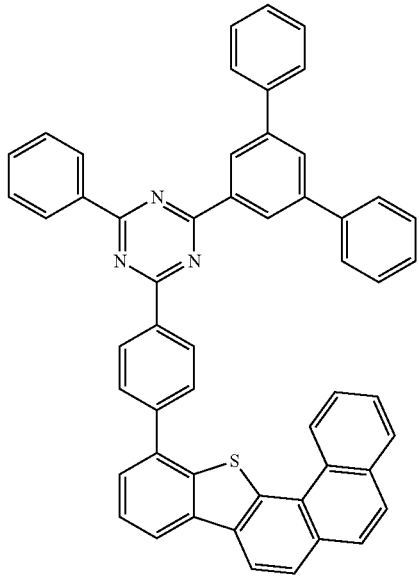
19
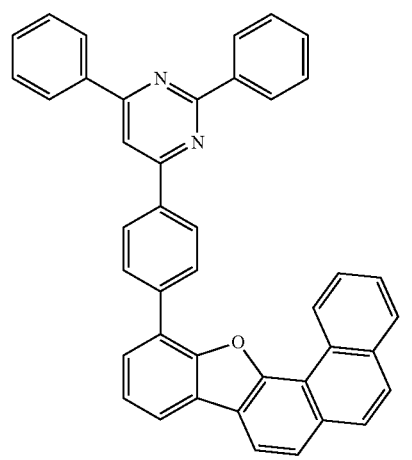
20
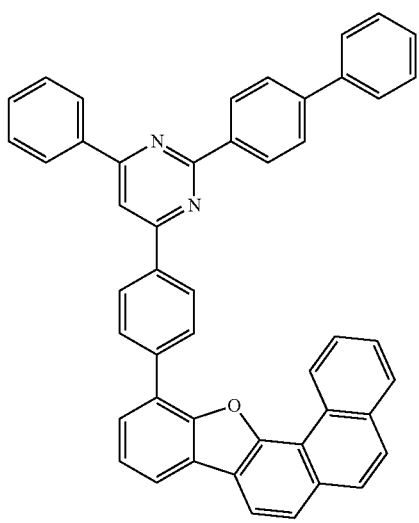
26
-continued
21
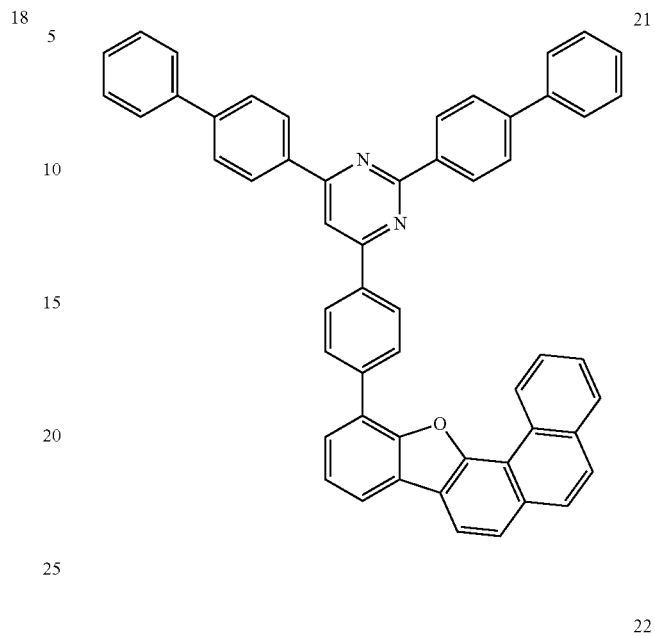
22
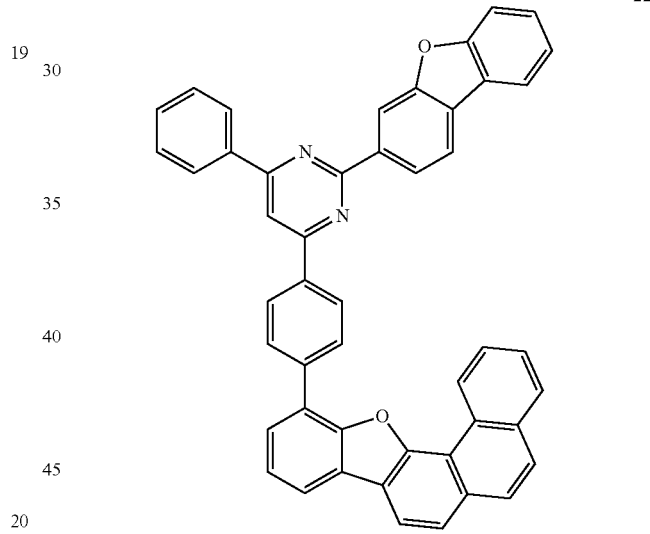
23
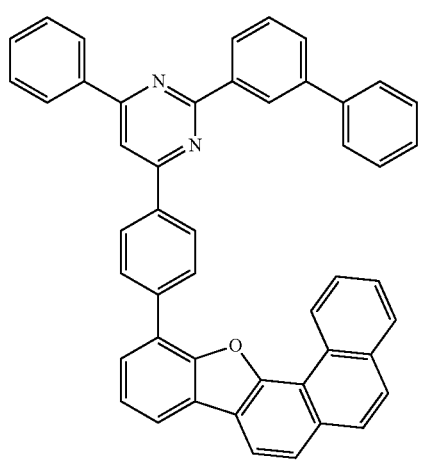

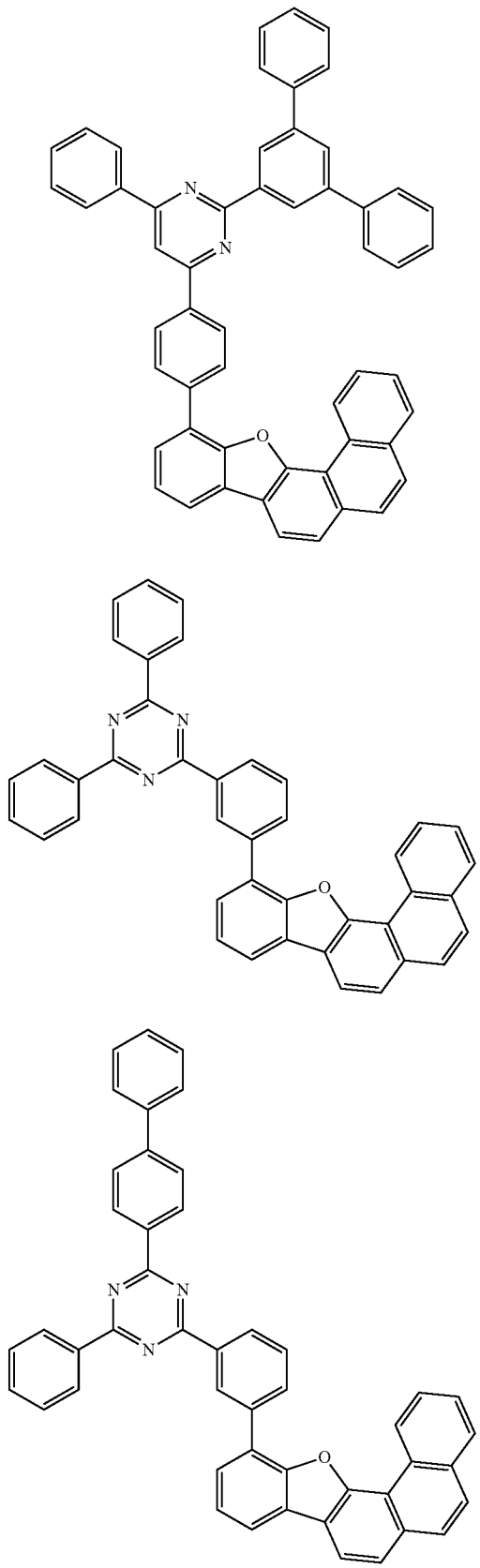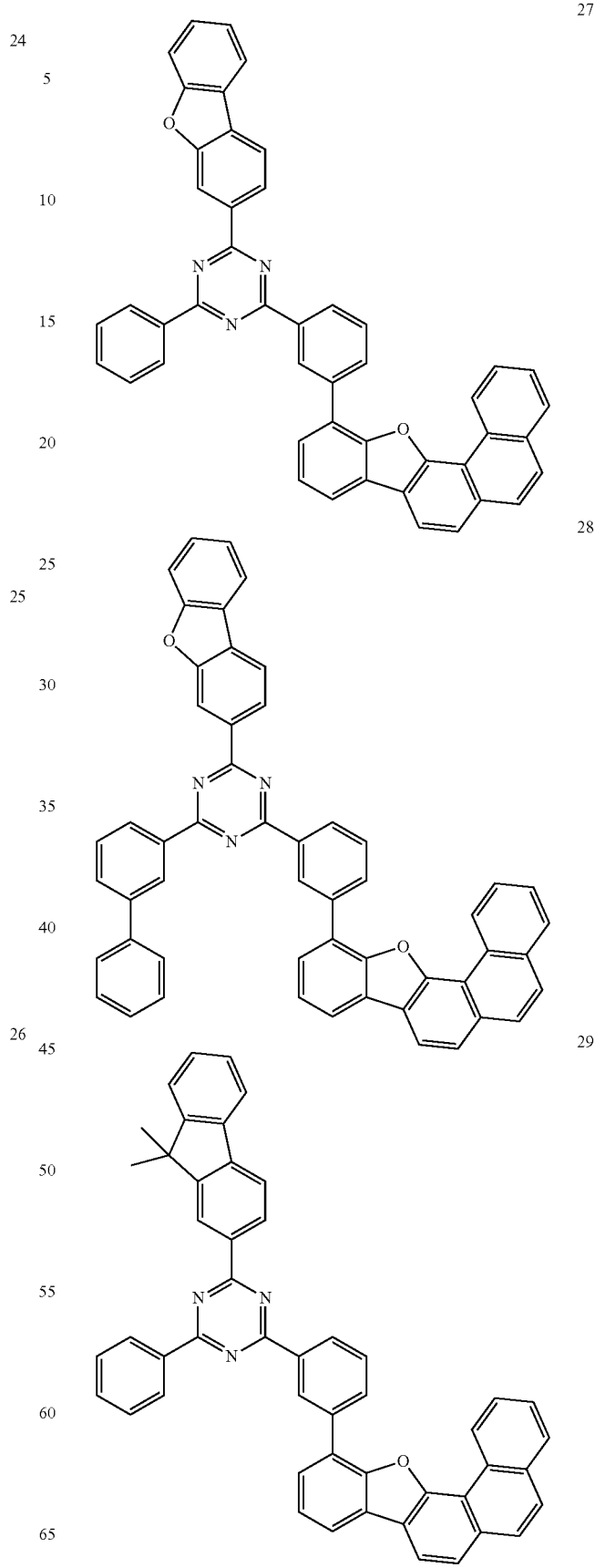

30
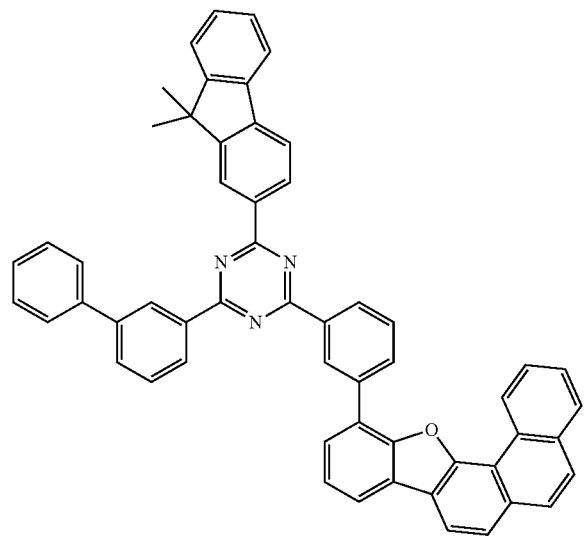
31
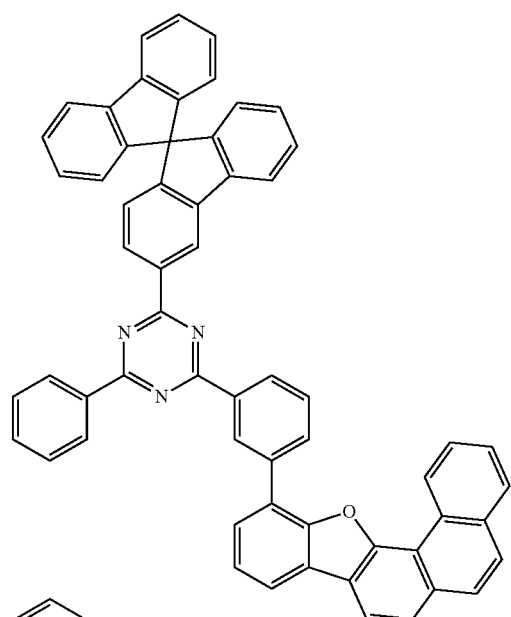
32
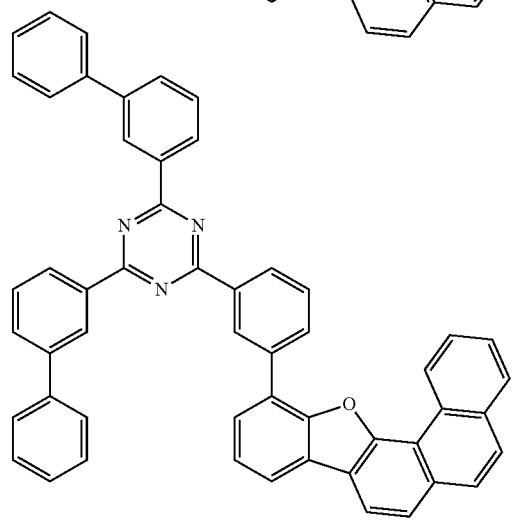
33
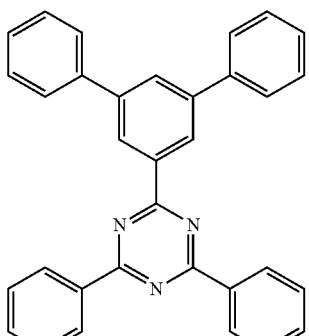
34
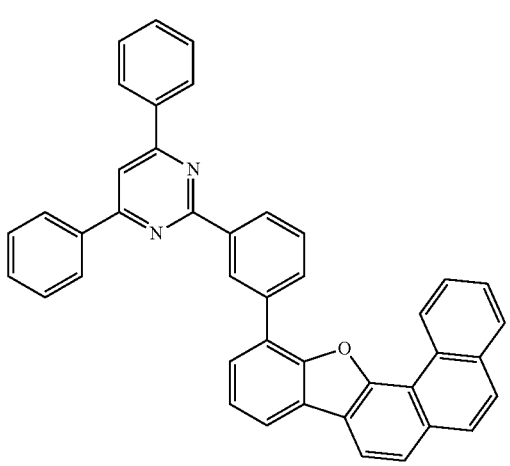
35
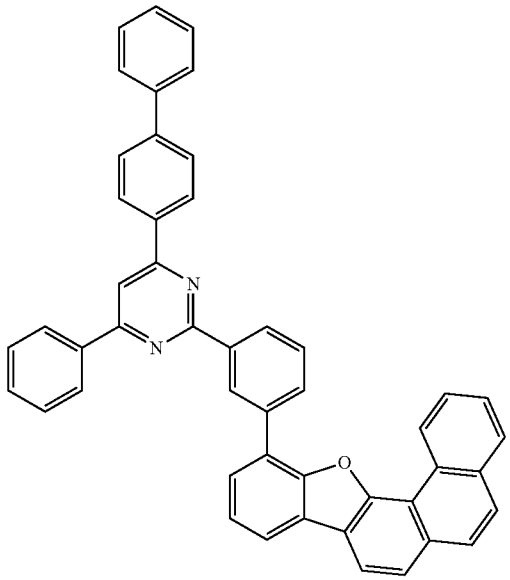

31
-continued
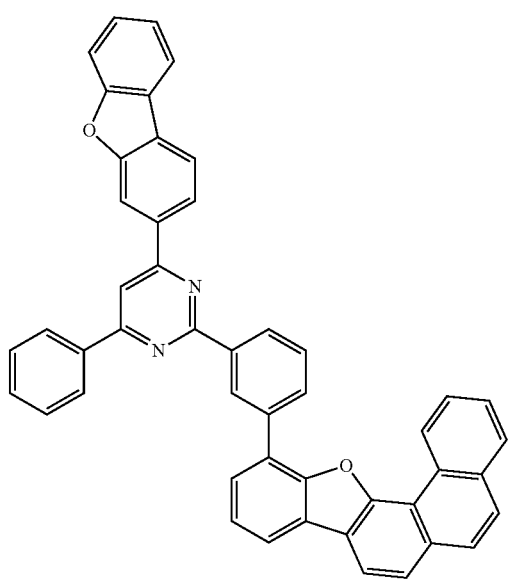
36
32
-continued
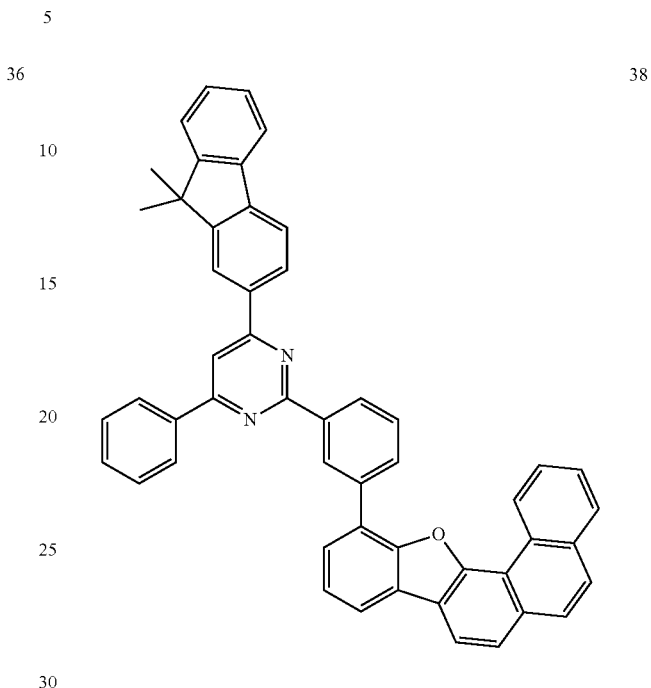
38
37
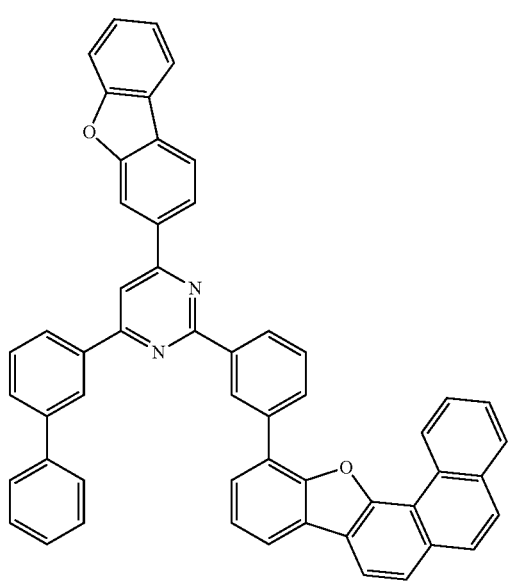
39
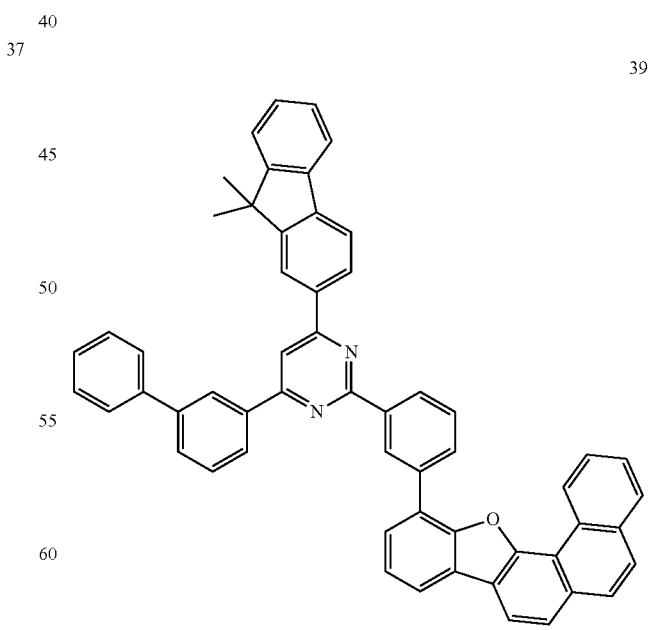

40
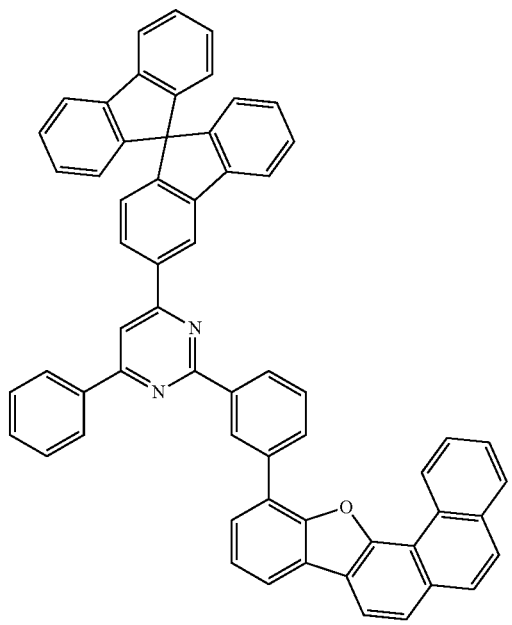
41
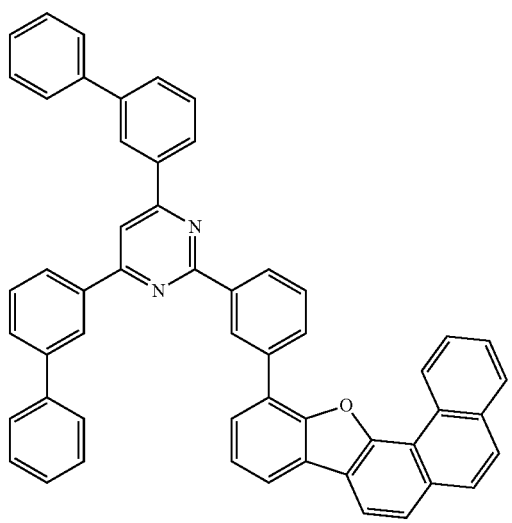
42
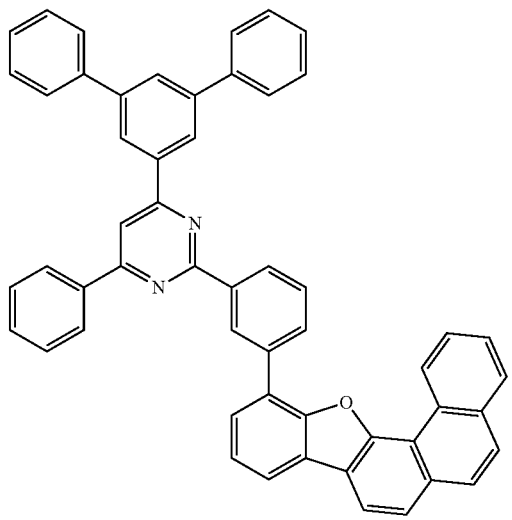
43
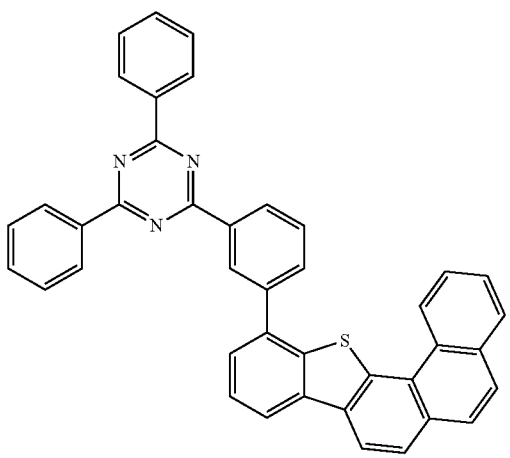
44
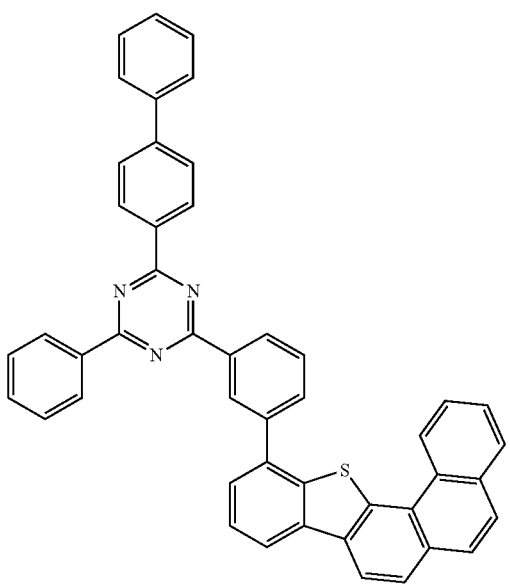
45
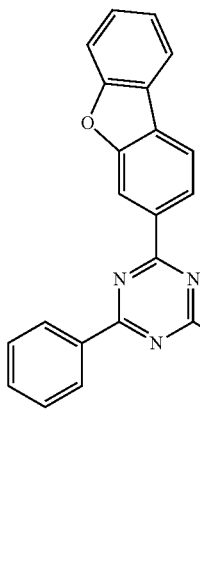

46
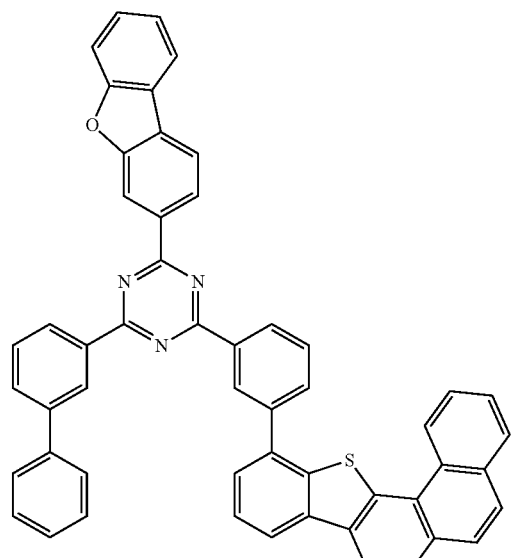
47
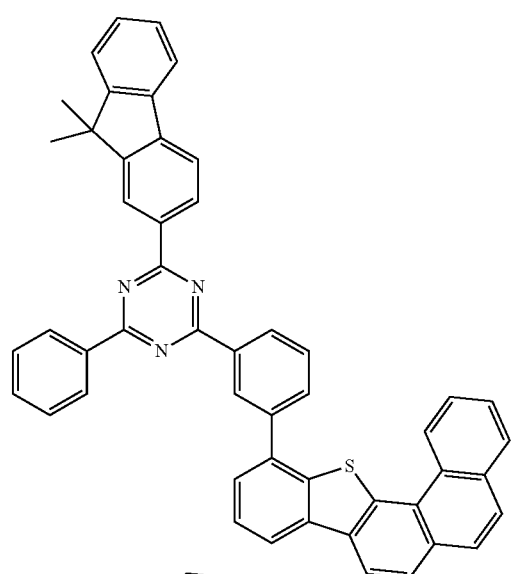
48
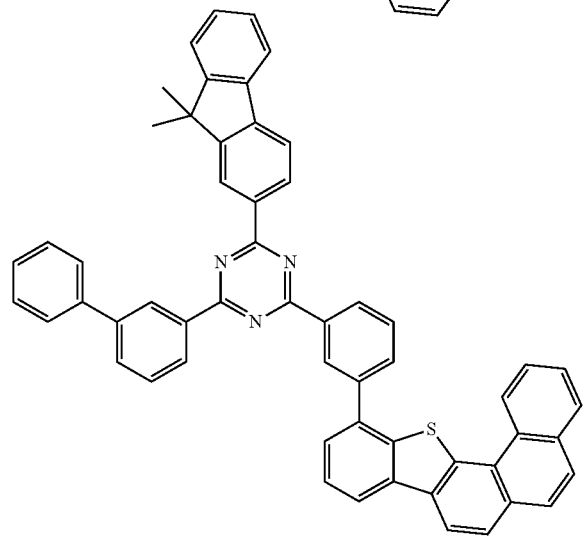
49
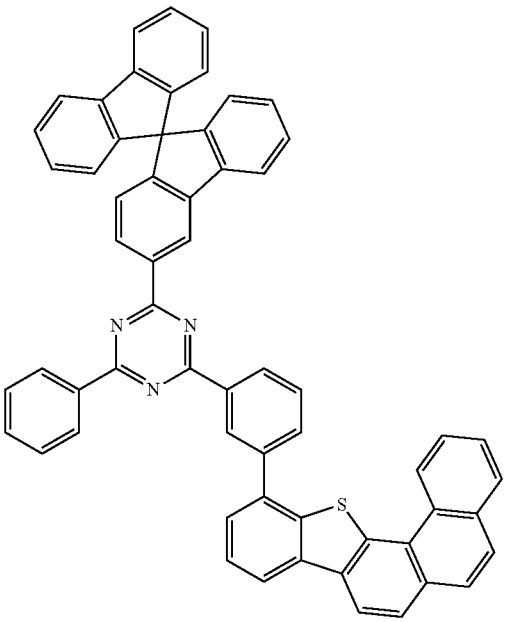
50
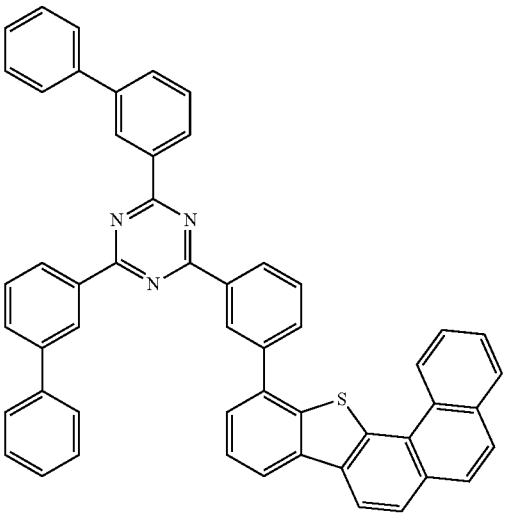
51
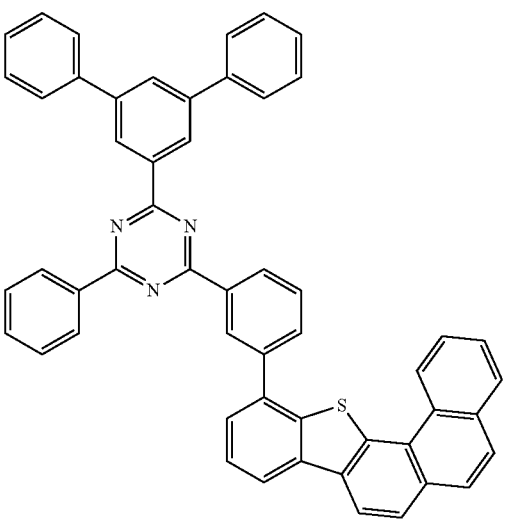

T1 energy of the aforementioned compound for an organic optoelectronic diode may be 2.55 eV to 2.65 eV.

In addition, the aforementioned first compound for an organic optoelectronic diode may be applied to an organic optoelectronic diode and may be applied to an organic optoelectronic diode alone or with other compound for an organic optoelectronic diode. When the aforementioned compound for an organic optoelectronic diode is used with the other compound for an organic optoelectronic diode, they may be applied in a form of a composition.

Hereinafter, one example of a composition for an organic optoelectronic diode including the aforementioned first compound for an organic optoelectronic diode is described.

A composition for an organic optoelectronic diode according to another embodiment of the present invention includes the aforementioned first compound for an organic optoelectronic diode; and a second compound for an organic optoelectronic diode represented by Chemical Formula 2.

[Chemical Formula 2]

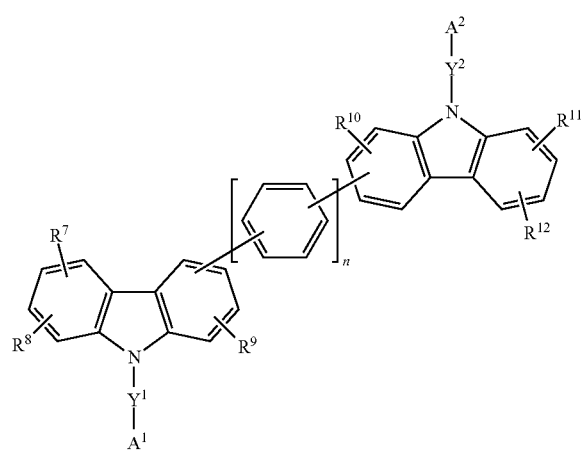

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $A^1$ and $A^2$ are independently a substituted or unsubstituted C6 to C30 aryl group, a substituted or unsubstituted C2 to C30 heterocyclic group, or a combination thereof, $R^7$ to $R^{12}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, n is one of integers of 0 to 2; and the "substituted" refers to replacement of at least one hydrogen by deuterium, a C1 to C4 alkyl group, a C6 to C18 aryl group, or a C2 to C30 heteroaryl group. In a specific embodiment of the present invention, the "substituted" refers to replacement of at least one hydrogen by deuterium, a phenyl group, an ortho-biphenyl group, a meta-biphenyl group, a para-biphenyl group, a terphenyl group, a naphthyl group, a fluorenyl group, a triphenylene group, a pyridinyl group, a carbazolyl group, a dibenzofuranyl group, or a dibenzothiophenyl group.

In an embodiment of the present invention, $Y^1$ and $Y^2$ of Chemical Formula 2 may independently be a single bond, or a substituted or unsubstituted C6 to C18 arylene group. Specifically, they may be a single bond, meta-phenylene group, or para-phenylene group.

In an embodiment of the present invention, $A^1$ and $A^2$ of Chemical Formula 2 may independently be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted dibenzofuranyl group, a substituted or unsubstituted dibenzothiophenyl group, a substituted or unsubstituted carbazolyl group, a substituted or unsubstituted fluorenyl group, or a combination thereof. Specifically, they may be a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted fluorenyl group, a substituted or unsubstituted carbazolyl group, a substituted or unsubstituted dibenzothiophenyl group, or a substituted or unsubstituted dibenzofuranyl group.

In an embodiment of the present invention, $R^6$ to $R^{11}$ of Chemical Formula 2 may independently be hydrogen, deuterium, or a substituted or unsubstituted C6 to C12 aryl group. Specifically, they may be hydrogen, or a phenyl group, and for example one of $R^6$ to $R^{11}$ may be a phenyl group and other may be hydrogen.

In an embodiment of the present invention, n of Chemical Formula 2 may be 0 or 1.

In a specific embodiment of the present invention, Chemical Formula 2 may be one of structures of Group II and *—$Y^1$-$A^1$ and *—$Y^2$-$A^2$ may be one of substituents of Group III.

[Group II]

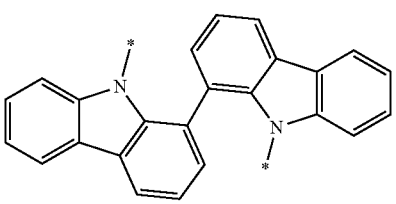

C-1

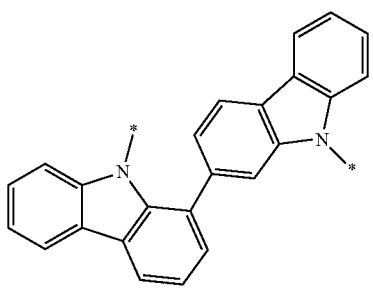

C-2

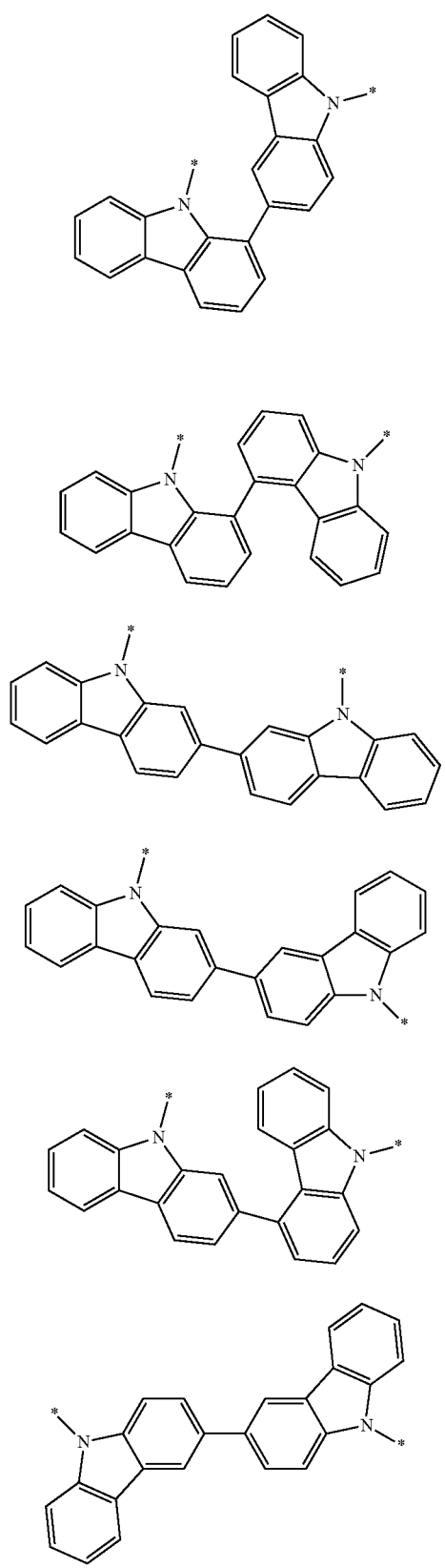
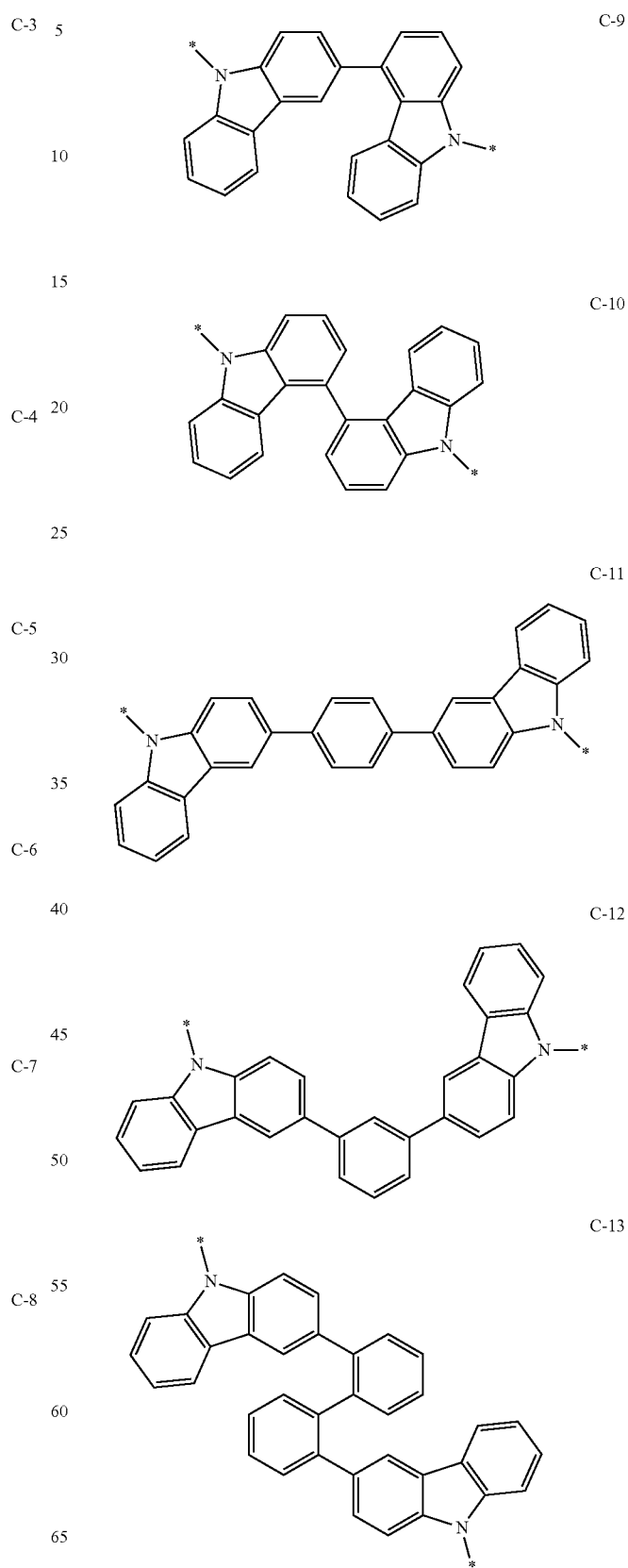

[Group III]
C-14
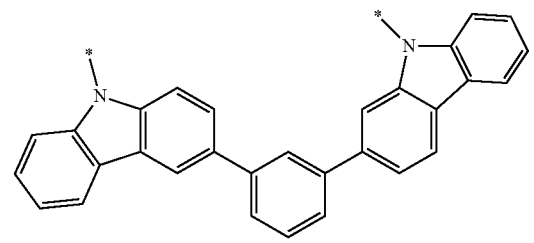
C-15
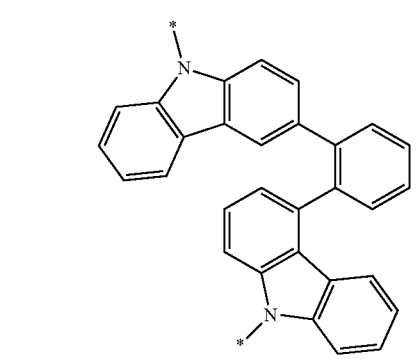
C-16
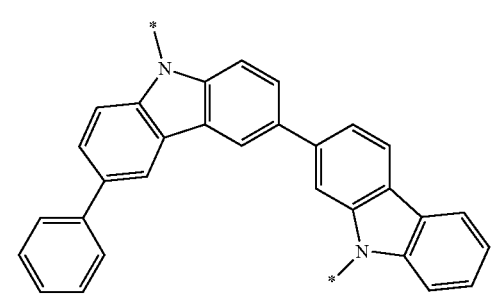
C-17
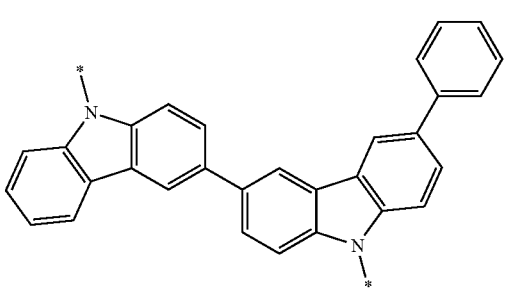
C-18
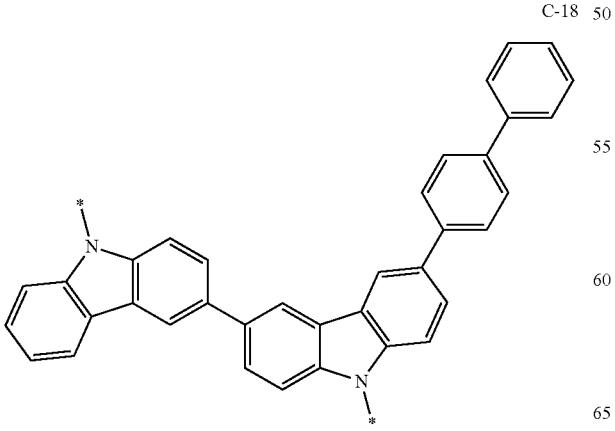
B-1
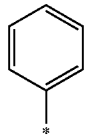
B-2
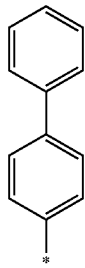
B-3
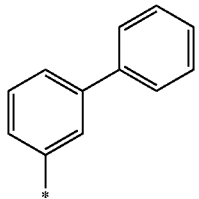
B-4
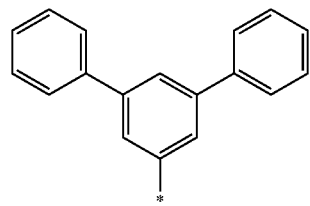
B-5
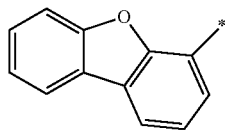
B-6
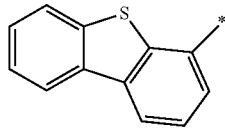
B-7
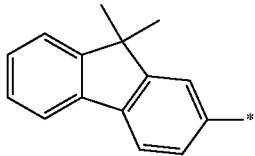
B-8
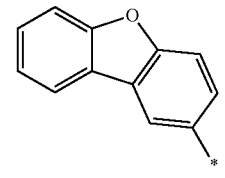

-continued
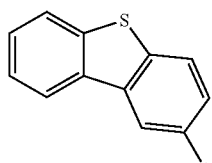
B-9
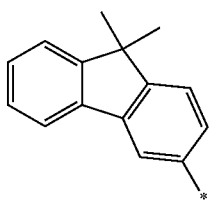
B-10
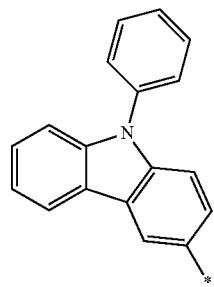
B-11
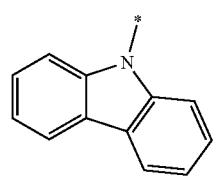
B-12
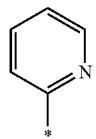
B-13
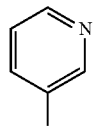
B-14
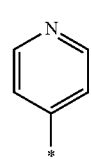
B-15
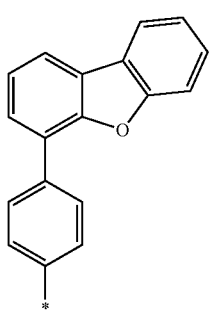
B-16
-continued
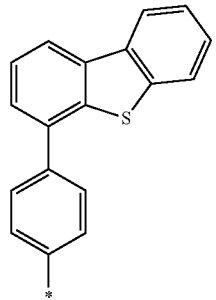
B-17
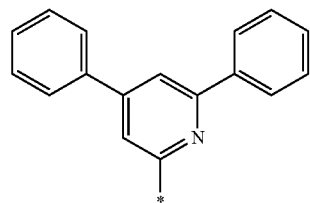
B-18
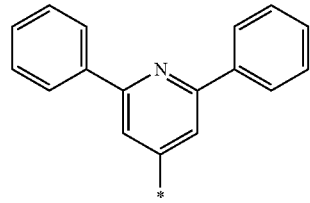
B-19
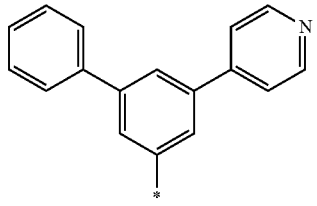
B-20
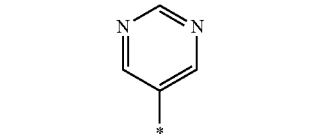
B-21
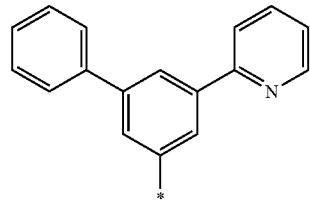
B-22
B-23

B-24

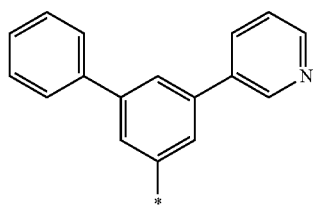

B-27

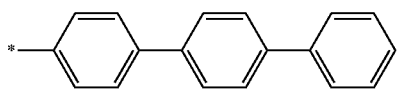

B-25

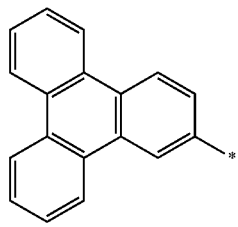

B-28

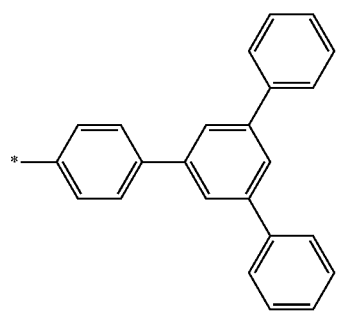

B-26

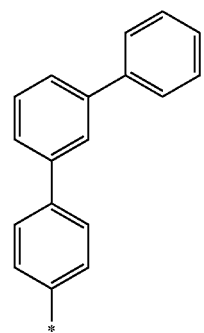

In Groups II and III, * is a linking point.

In an embodiment of the present invention, Chemical Formula 2 may be represented by Chemical Formula C-8 or Chemical Formula C-17 of Group II, and

*—$Y^1$-$A^1$ and *—$Y^2$-$A^2$ may be selected from B-1, B-2, and B-3 of Group III.

The second compound for an organic optoelectronic diode represented by Chemical Formula 2 may be for example selected from compounds of Group 2.

[Group 2]

[E-1]

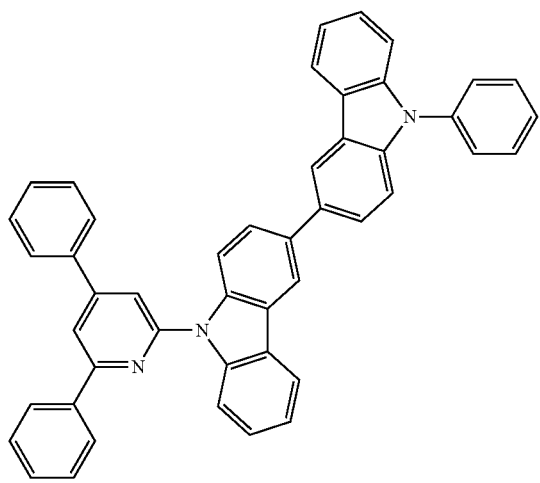

[E-2]

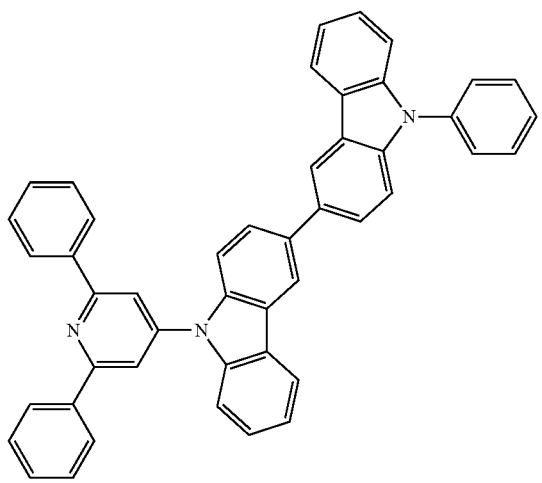

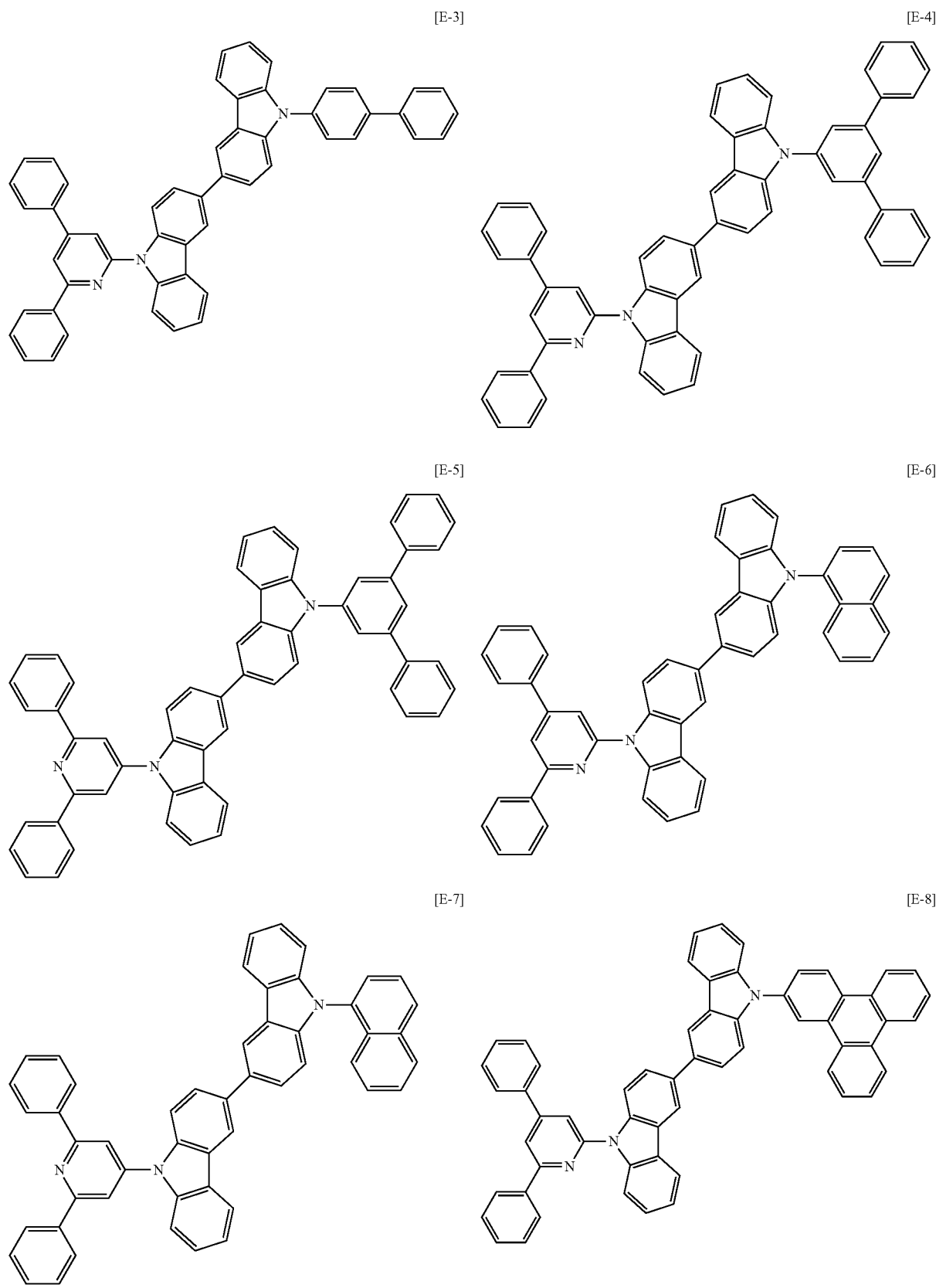

-continued
[E-9]
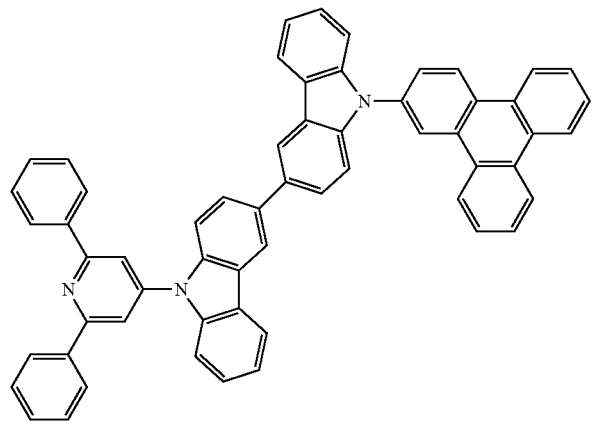
[E-10]
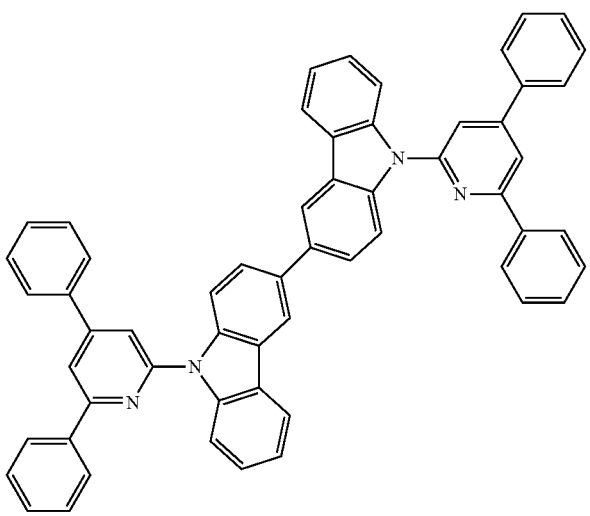
[E-11]
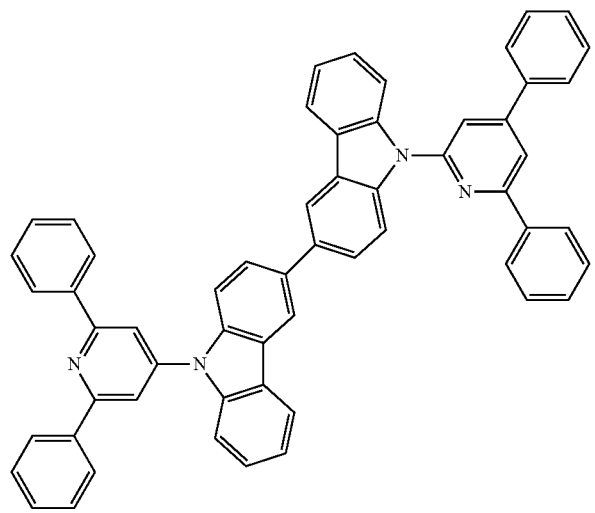
[E-12]
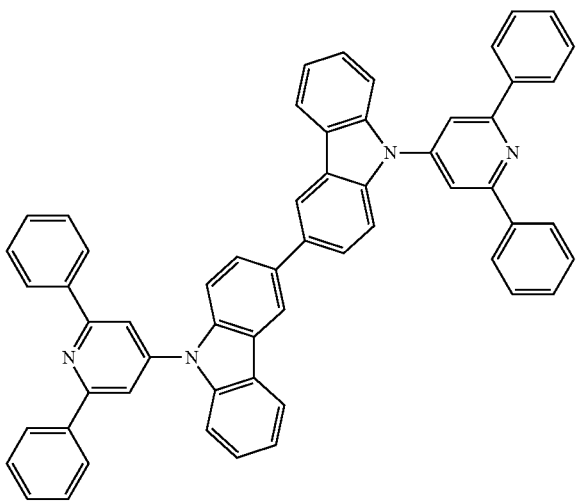
[E-13]
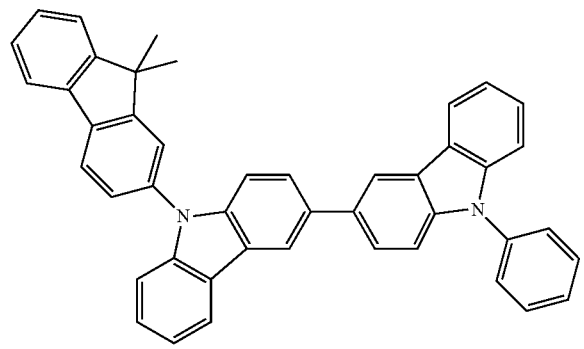
[E-14]
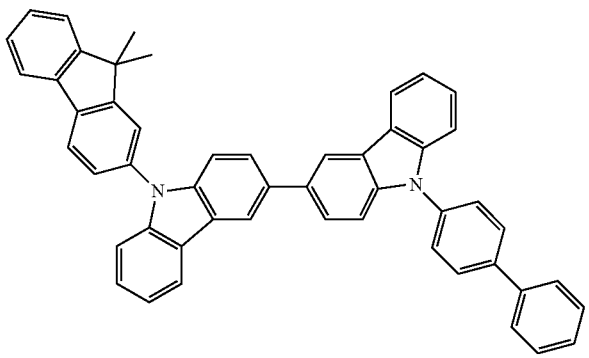

[E-15]
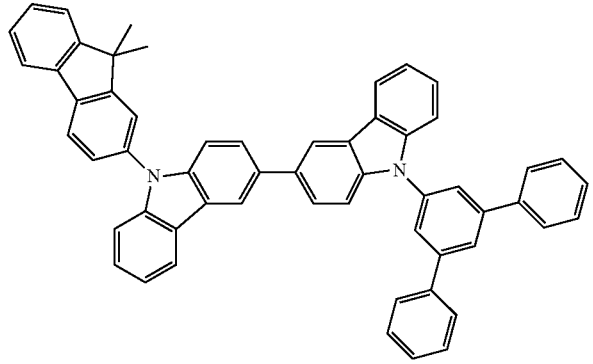
[E-16]
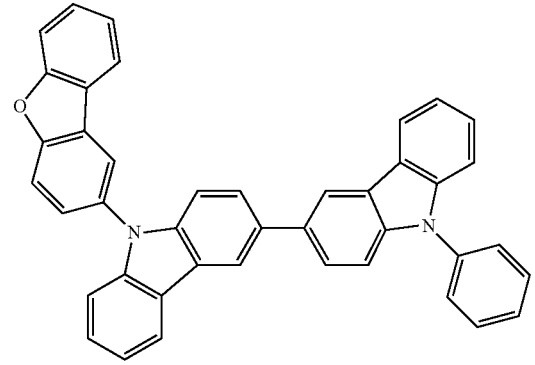
[E-17]
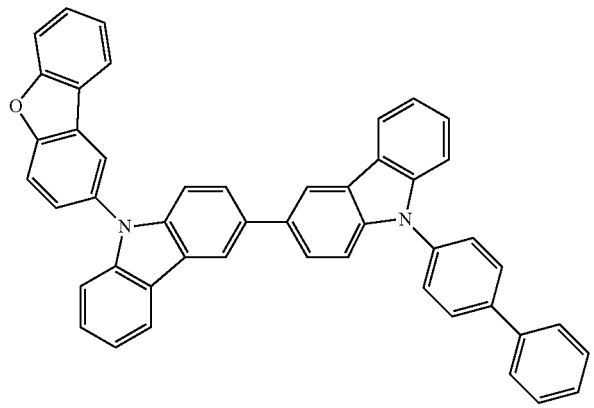
[E-18]
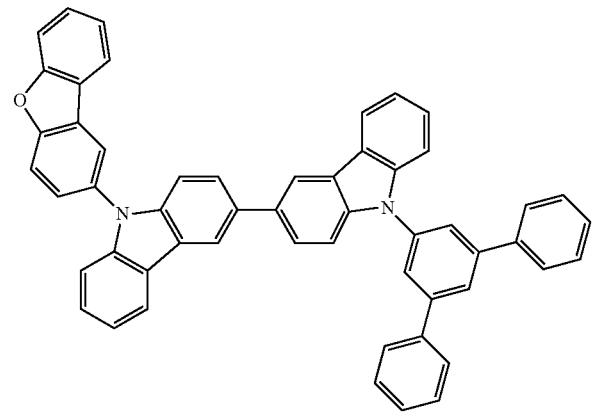
[E-19]
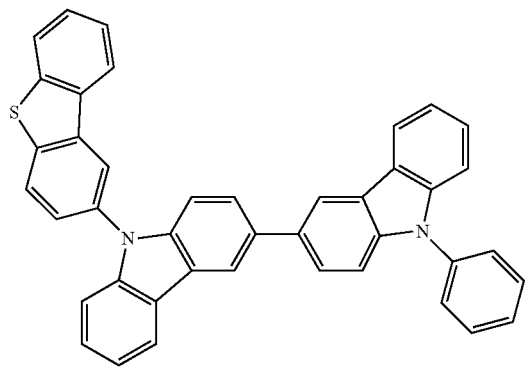
[E-20]
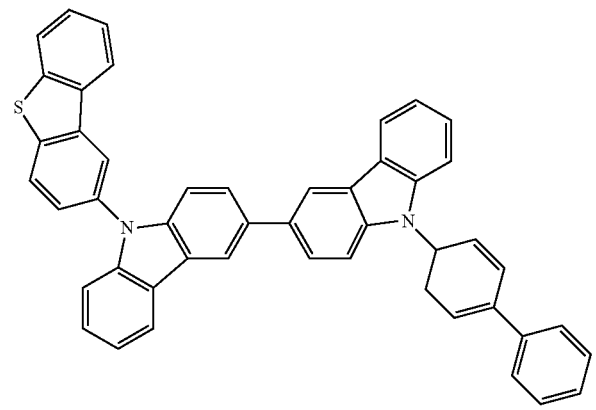

-continued
[E-21]
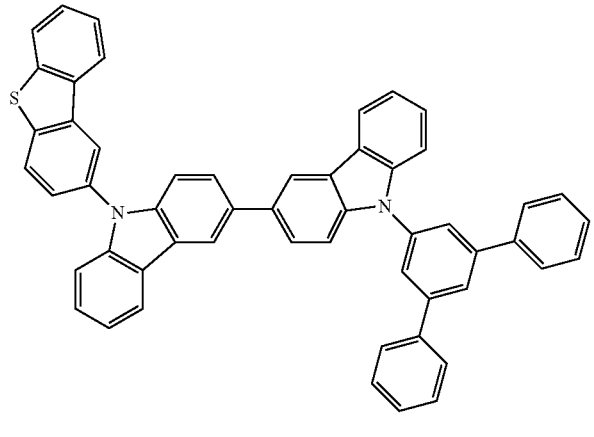
[E-22]
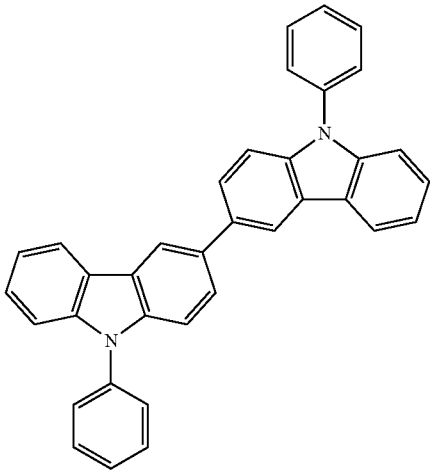
[E-23]
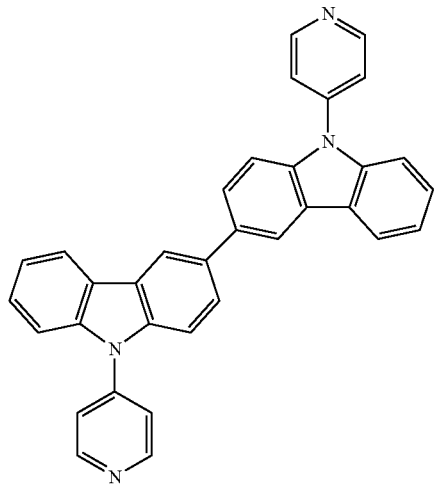
[E-24]
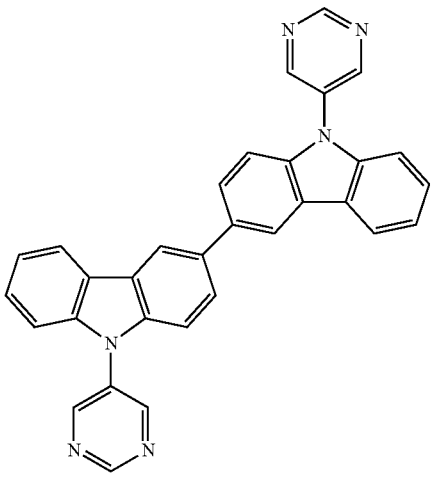
[E-25]
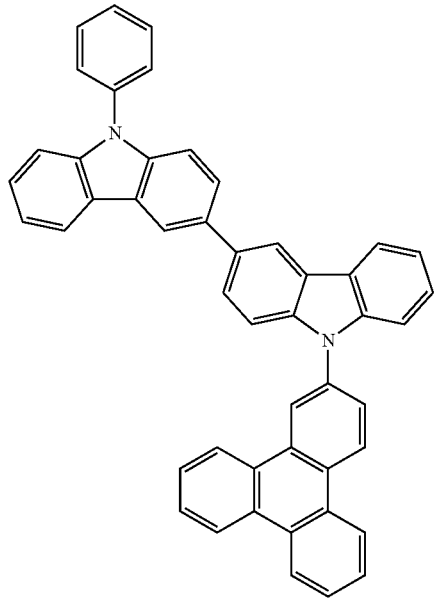
[E-26]
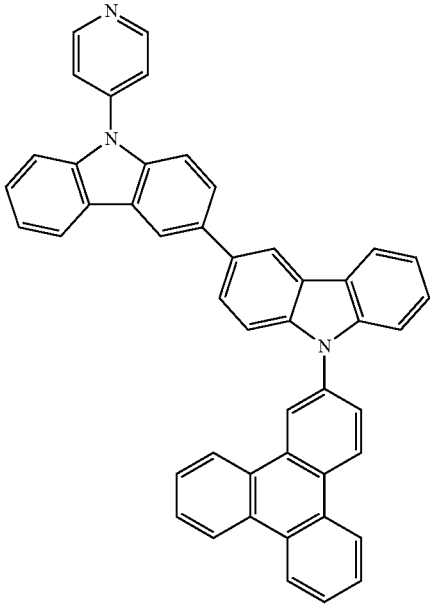

-continued
[E-27]
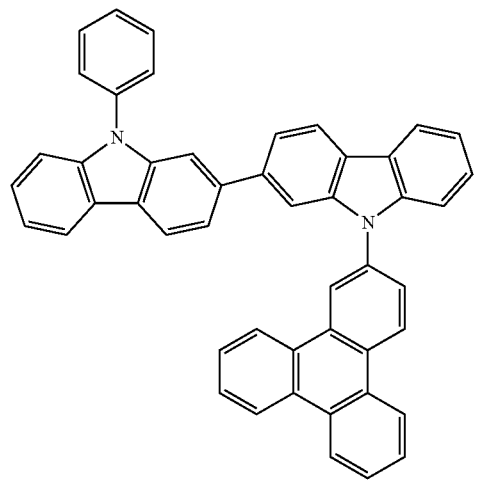
[E-28]
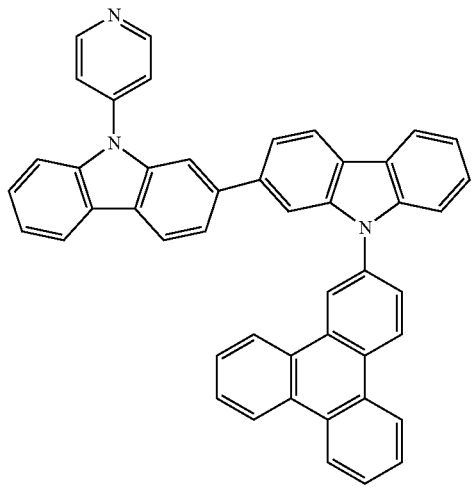
[E-29]
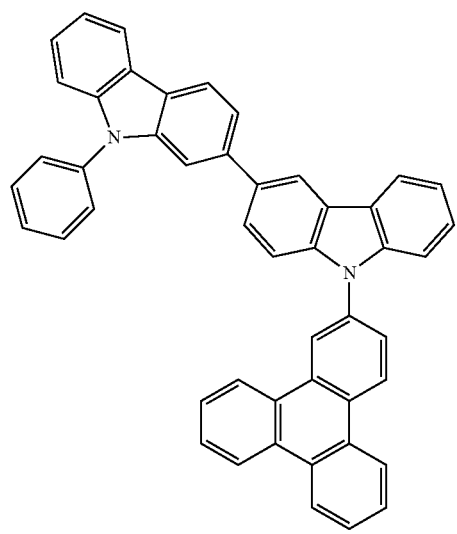
[E-30]
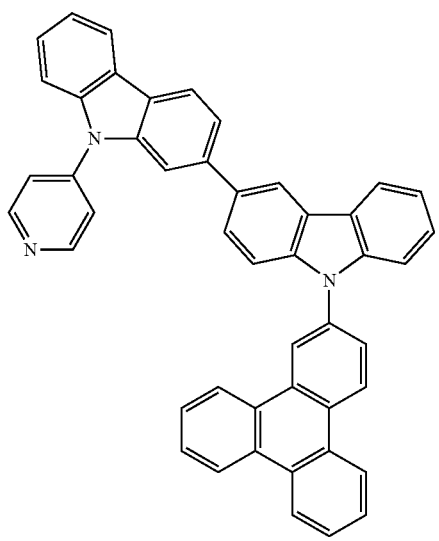
[E-31]
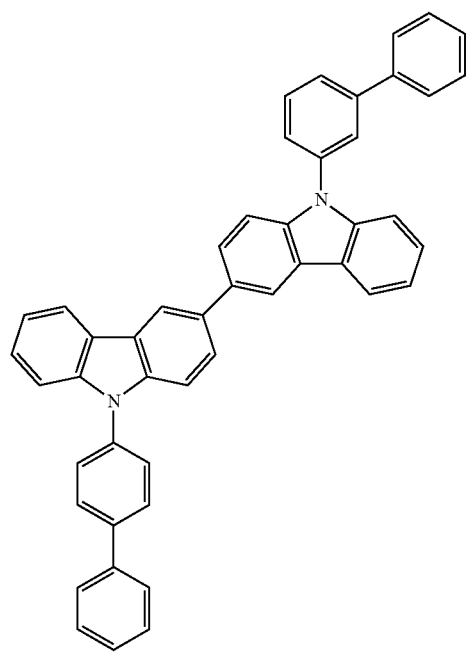
[E-32]
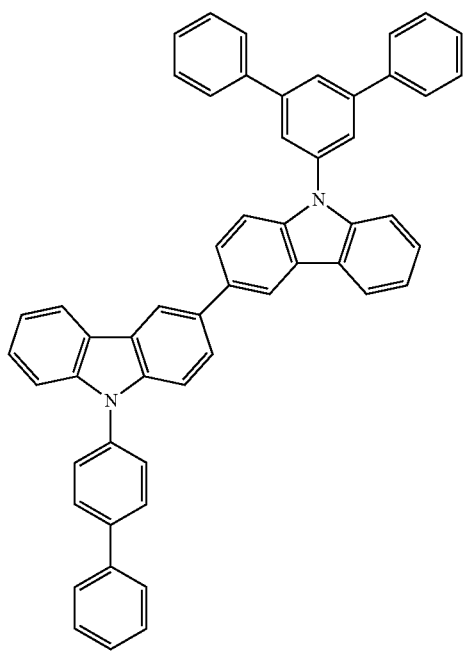

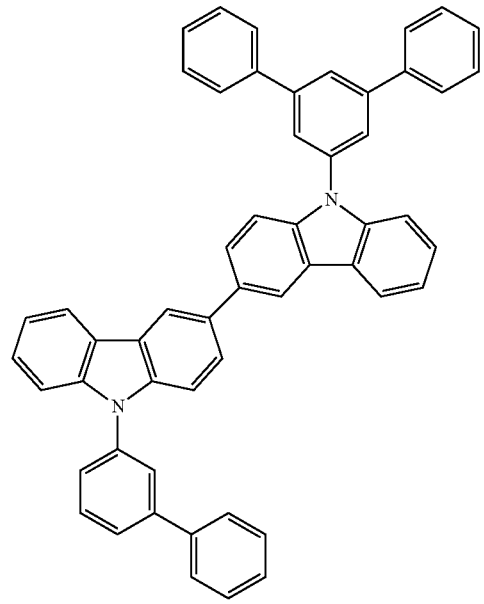
[E-33]
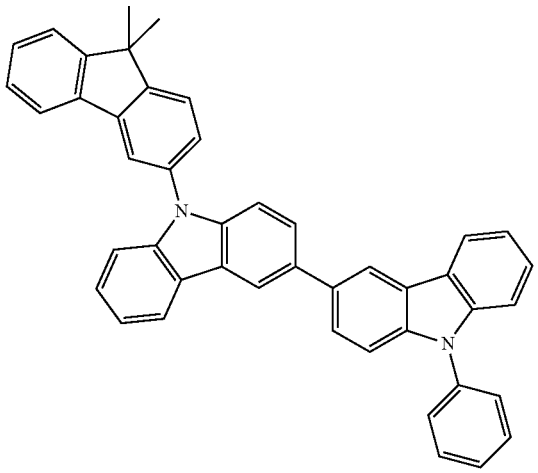
[E-34]
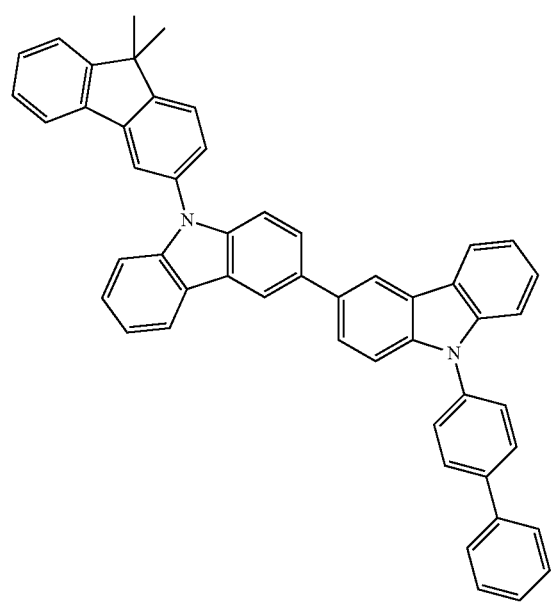
[E-35]
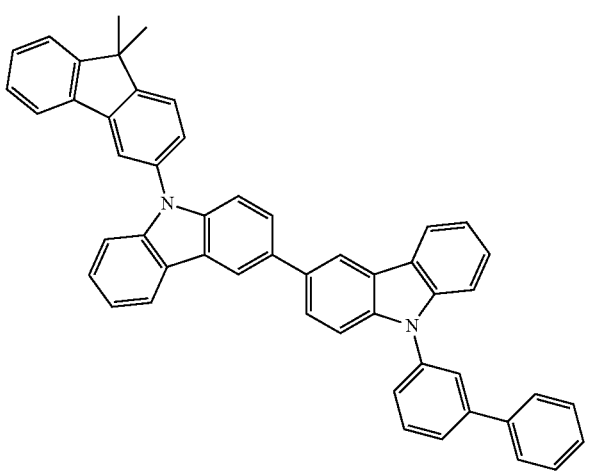
[E-36]

-continued
[E-37]
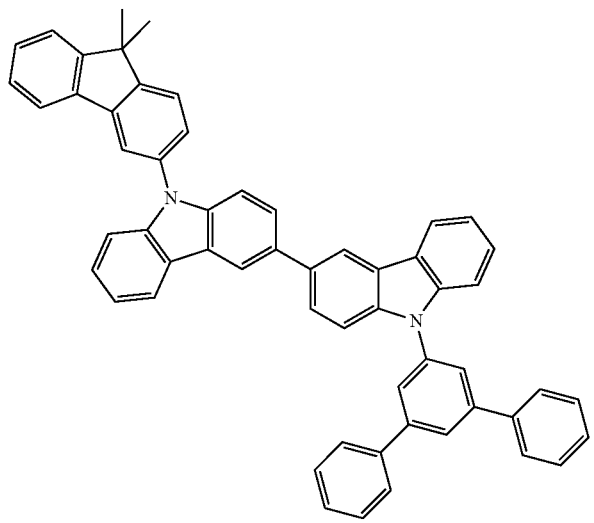
[E-38]
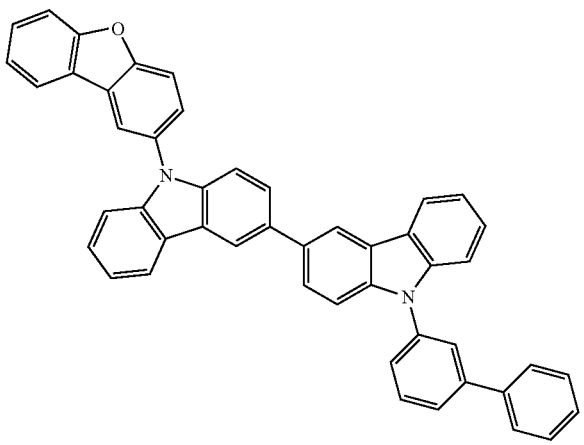
[E-39]
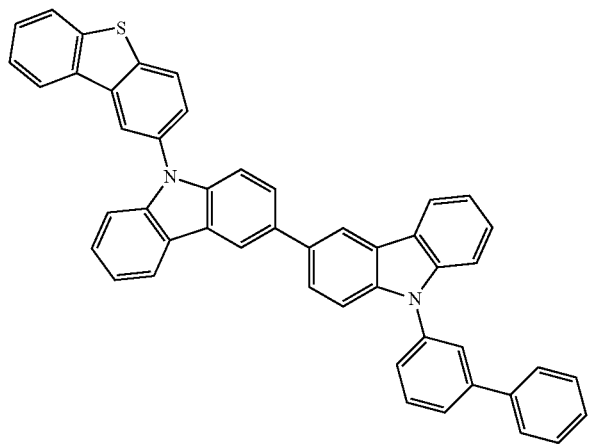
[E-40]
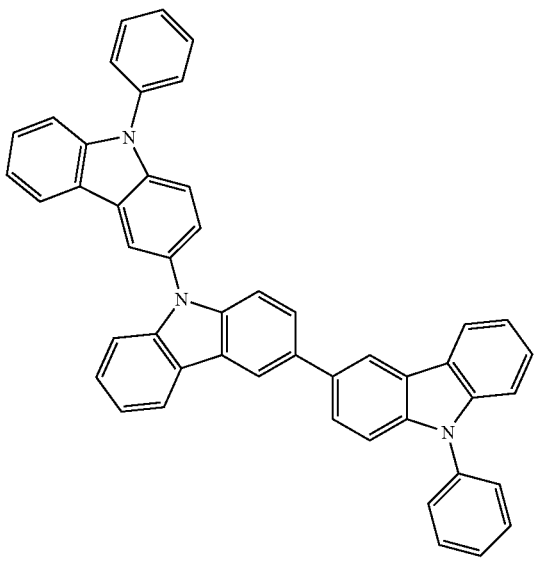
[E-41]
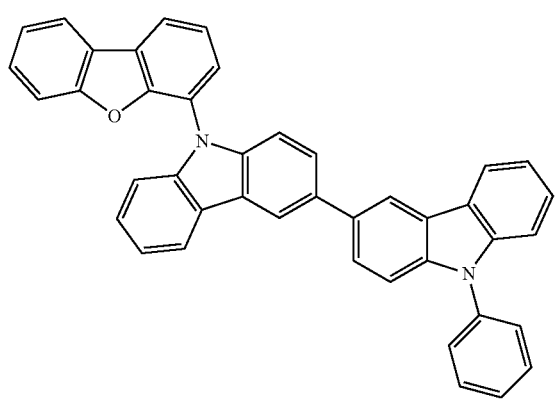
[E-42]
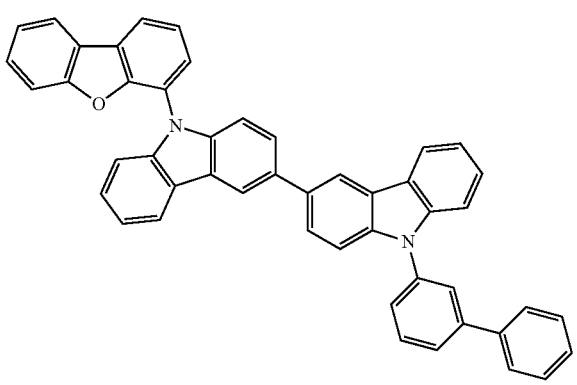

-continued
[E-43]
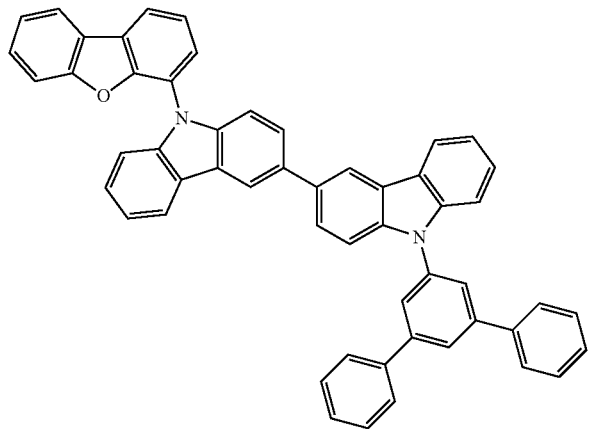
[E-44]
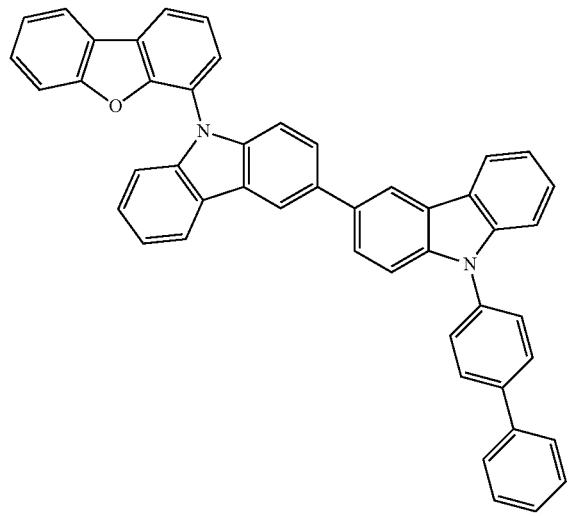
[E-45]
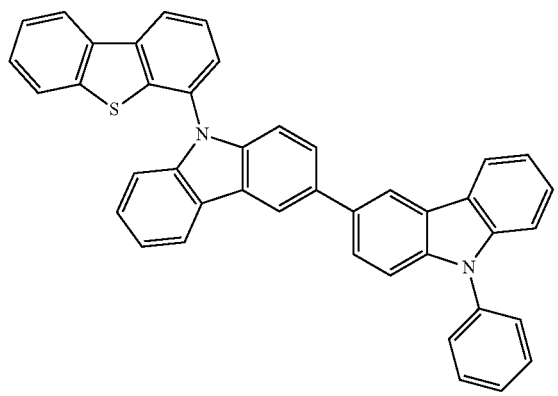
[E-46]
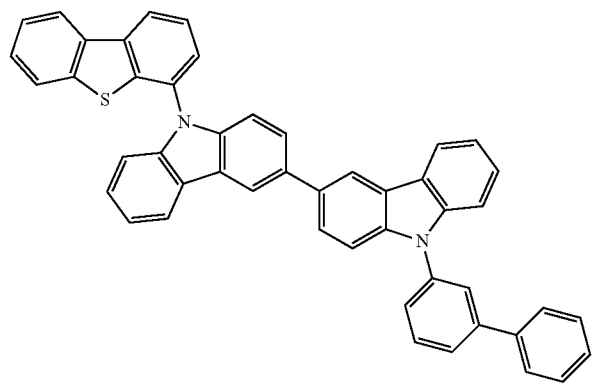
[E-47]
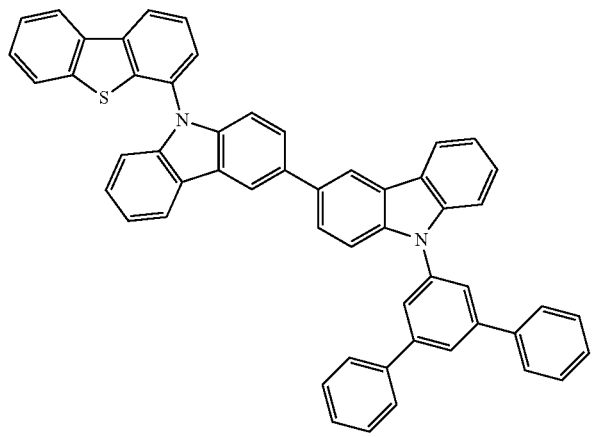
[E-48]
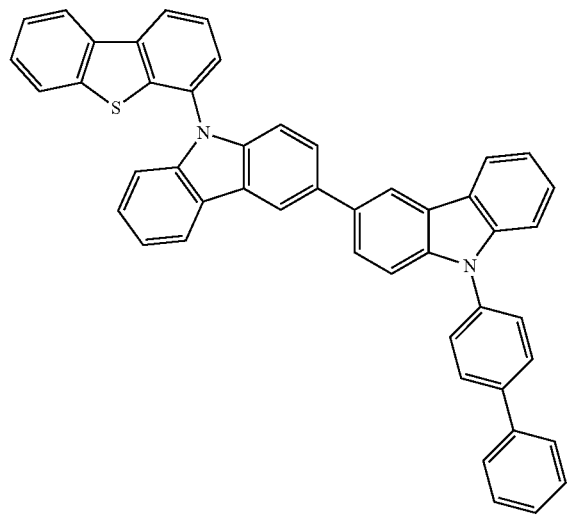

[E-49]
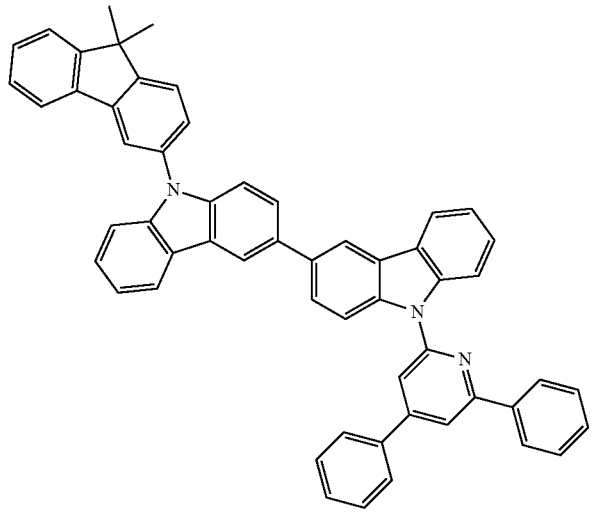
[E-50]
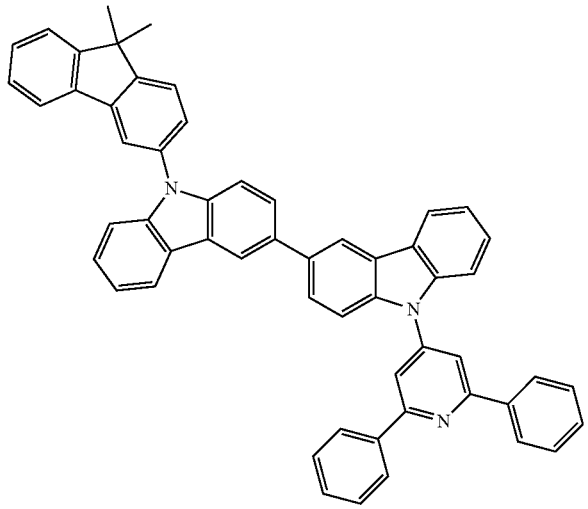
[E-51]
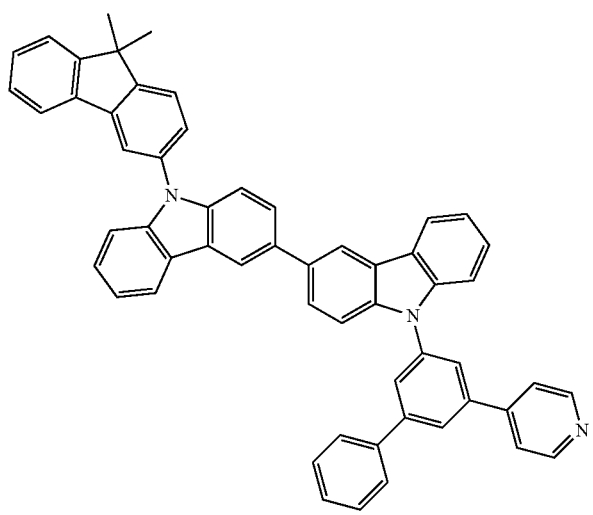
[E-52]
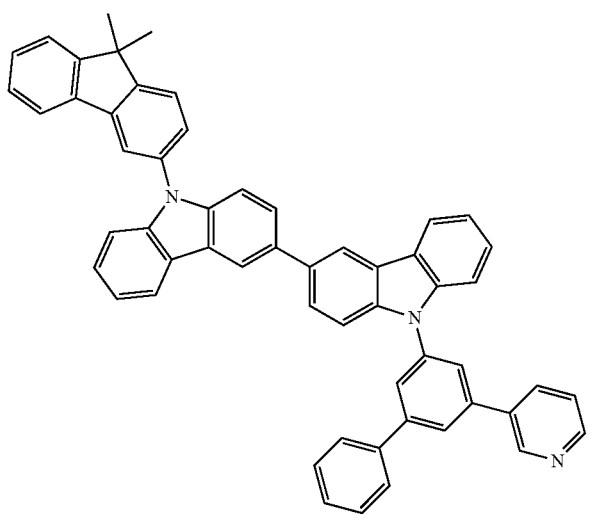
[E-53]
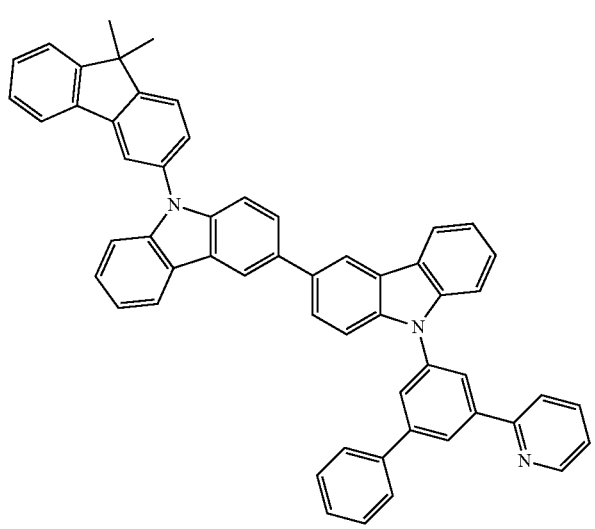
[E-54]
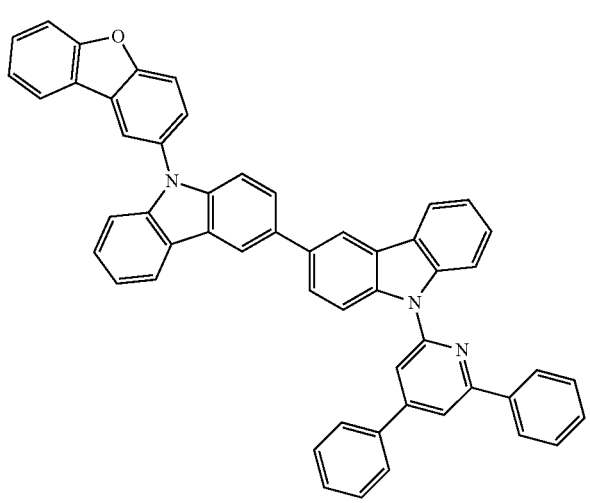

-continued
[E-55]
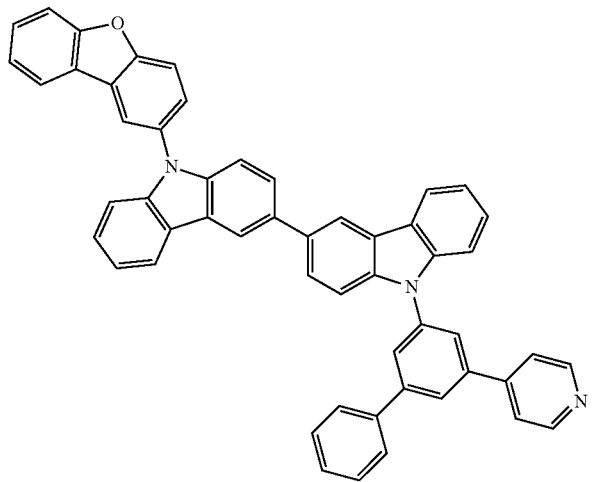
[E-56]
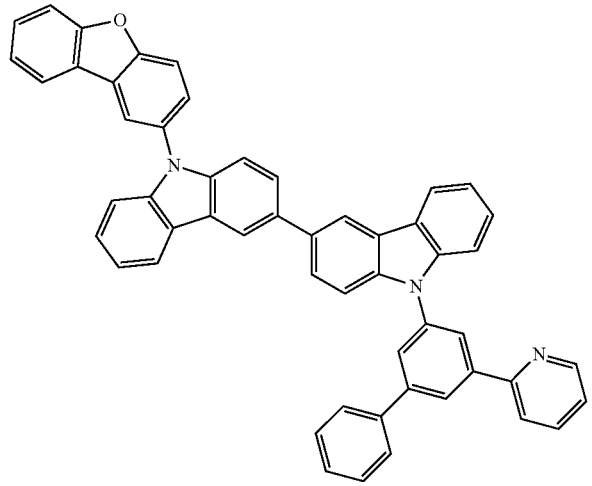
[E-57]
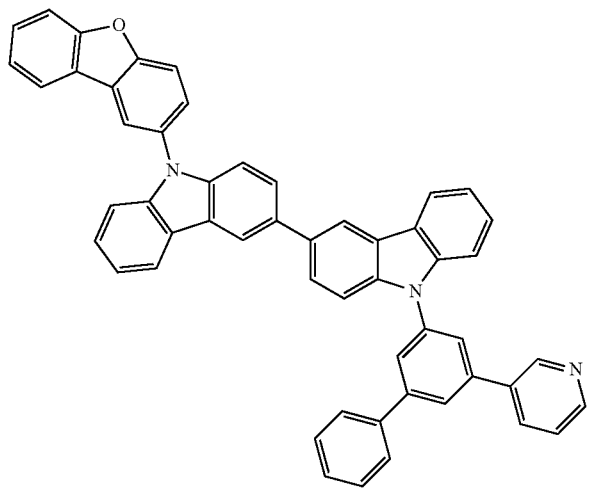
[E-58]
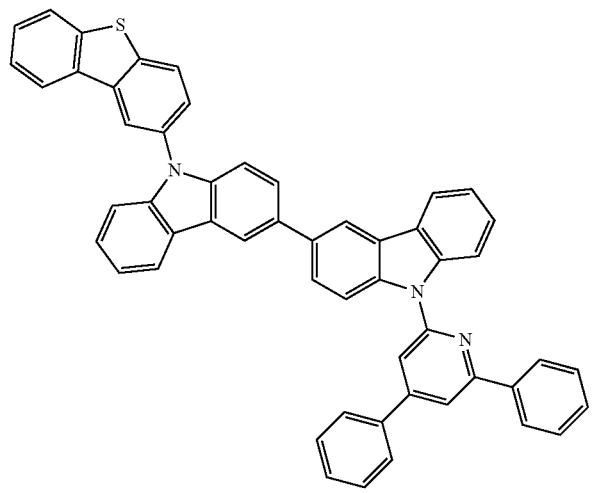
[E-59]
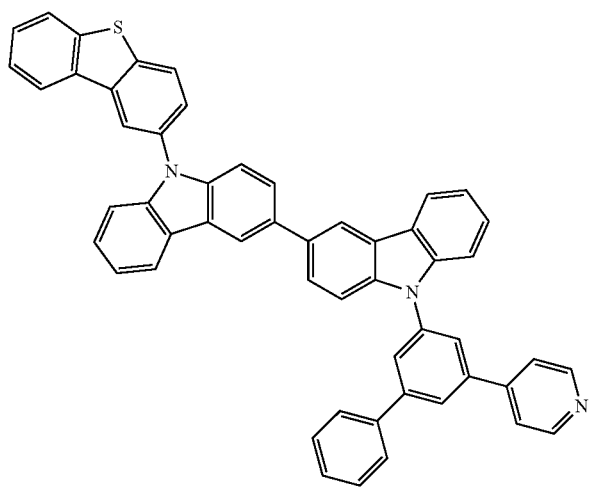
[E-60]
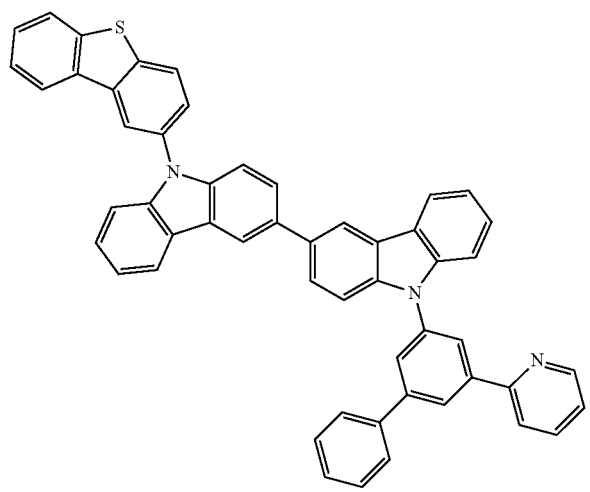

-continued
[E-61]
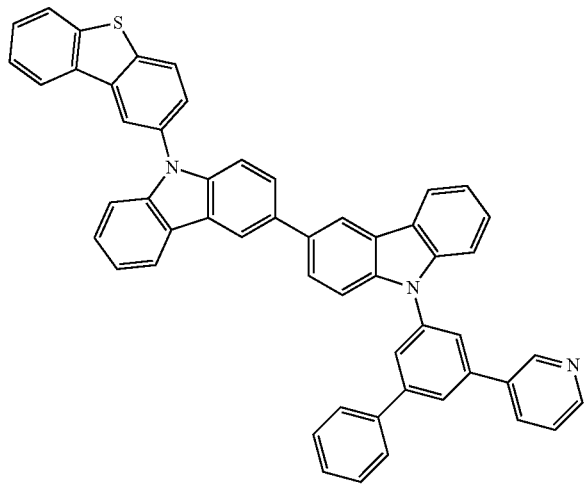
[E-62]
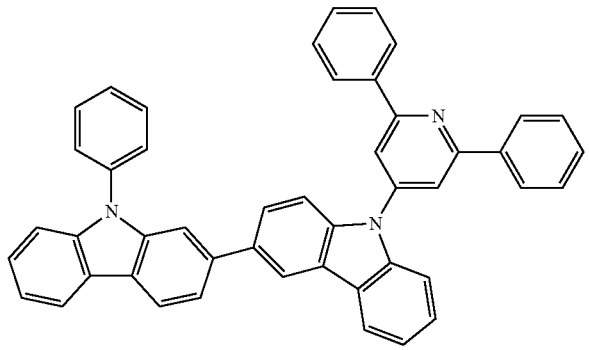
[E-63]
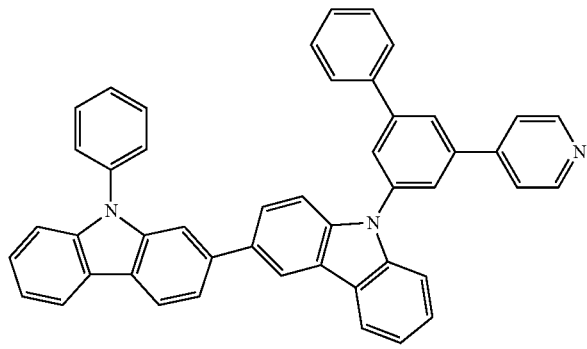
[E-64]
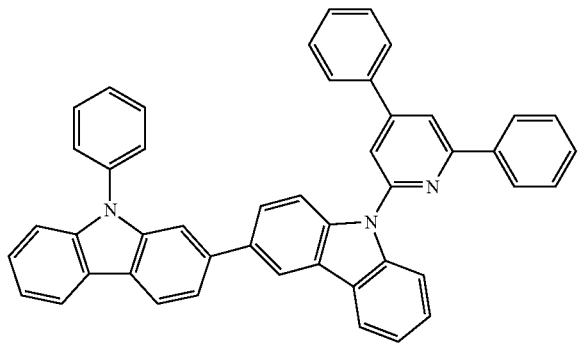
[E-65]
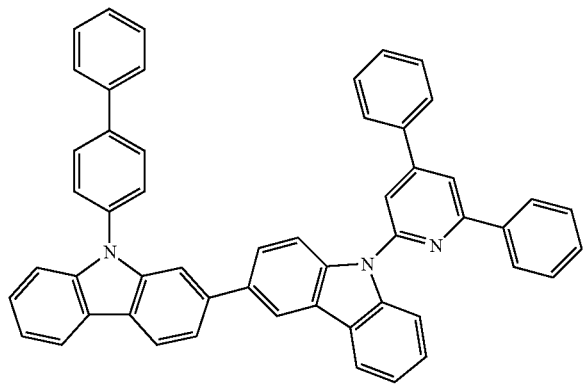
[E-66]
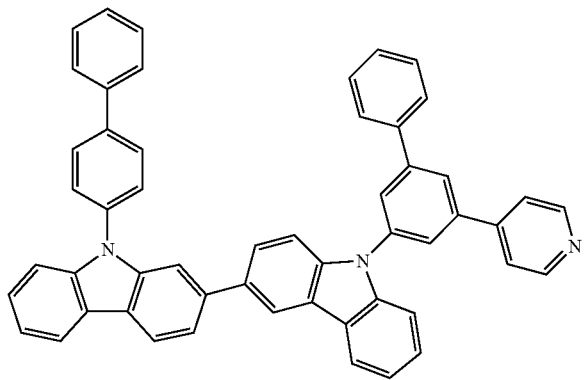

-continued
[E-67]
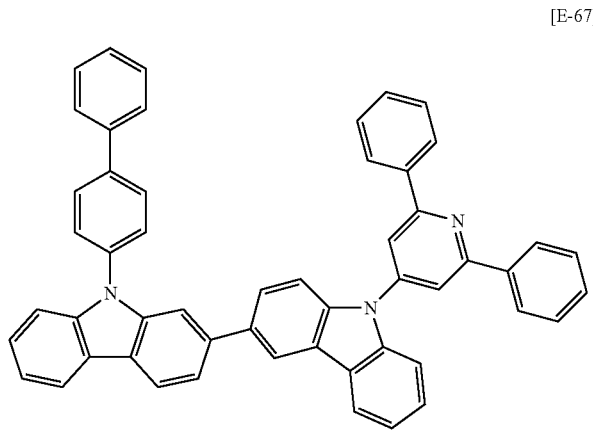
[E-68]
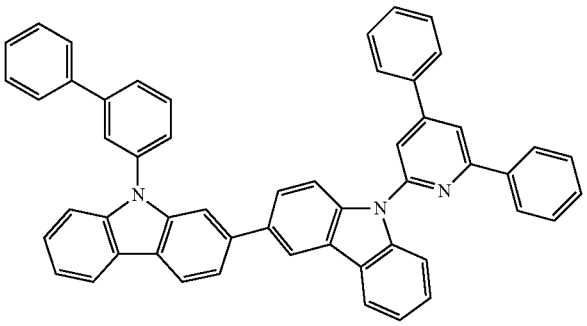
[E-69]
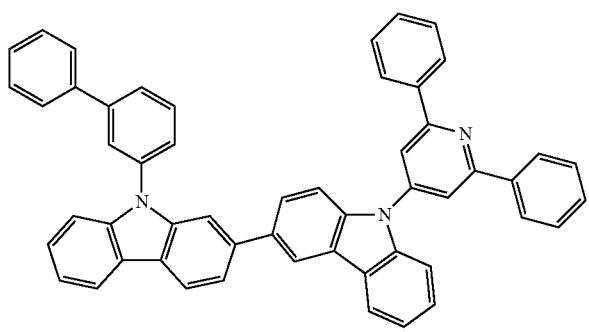
[E-70]
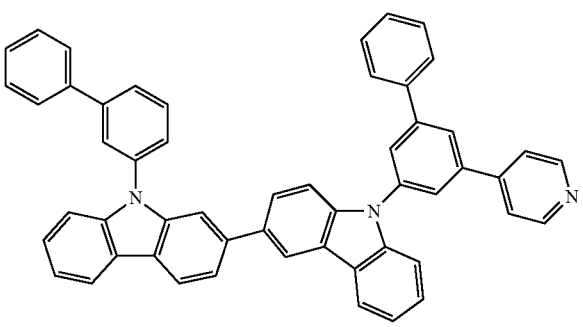
[E-71]
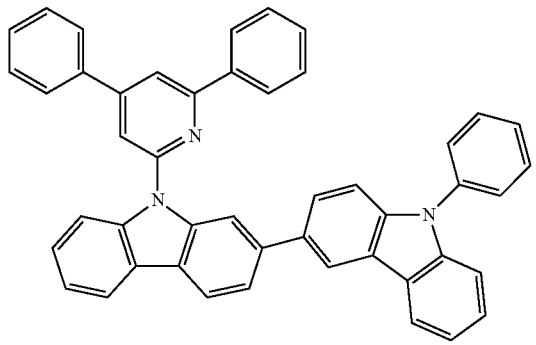
[E-72]
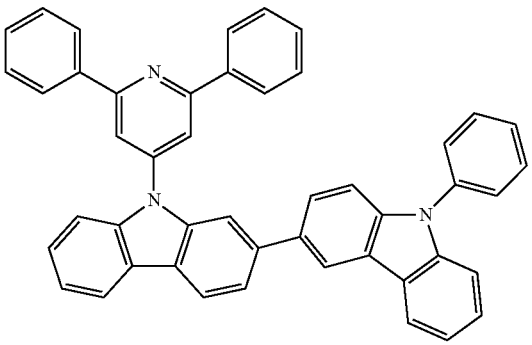
[E-73]
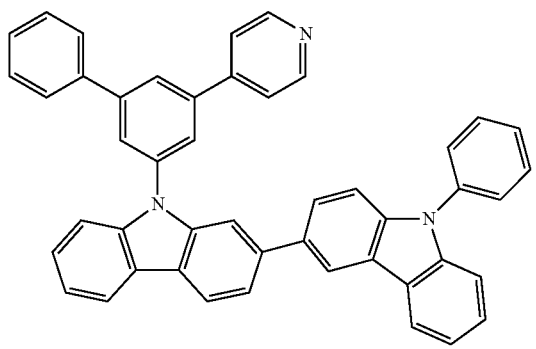
[E-74]
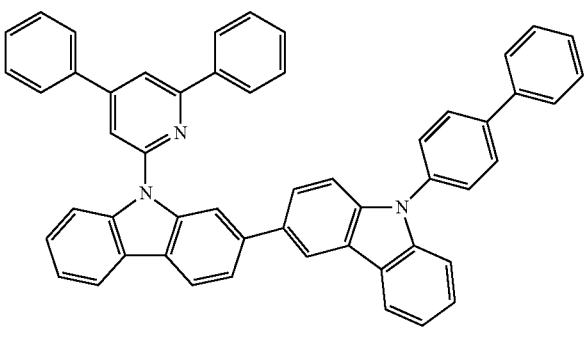

[E-75]
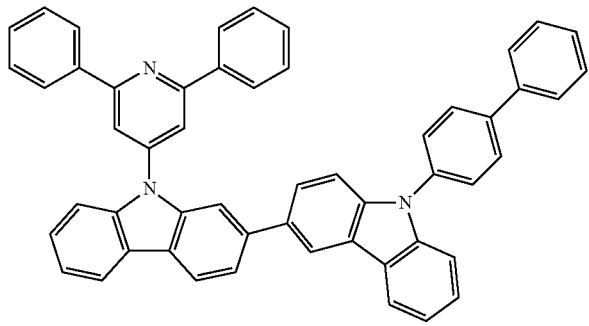
[E-76]
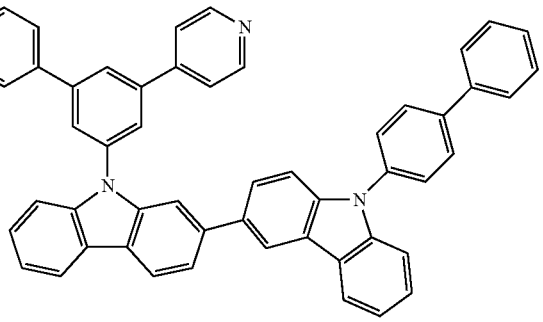
[E-81]
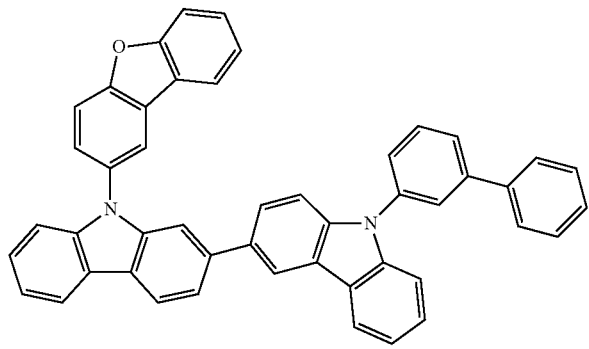
[E-82]
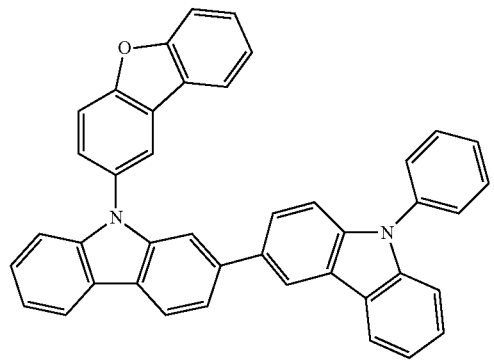
[E-83]
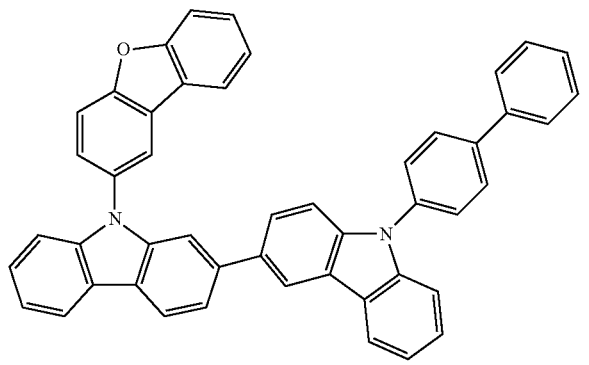
[E-84]
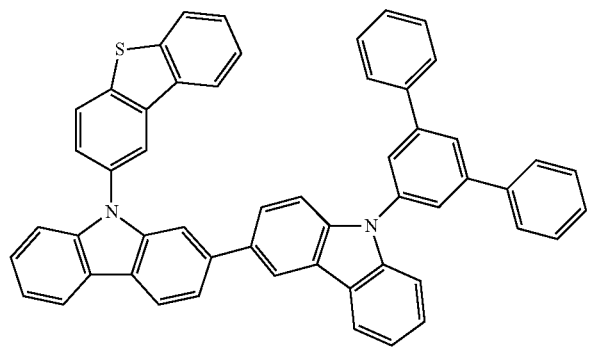
[E-85]
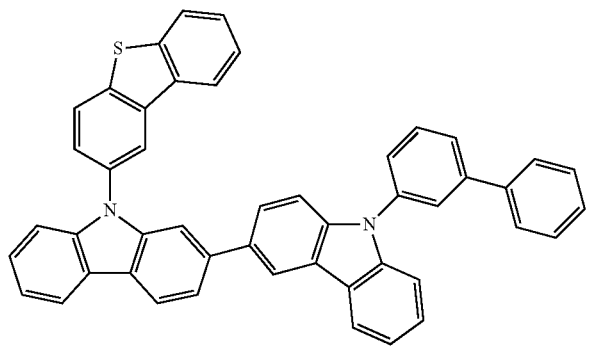
[E-86]
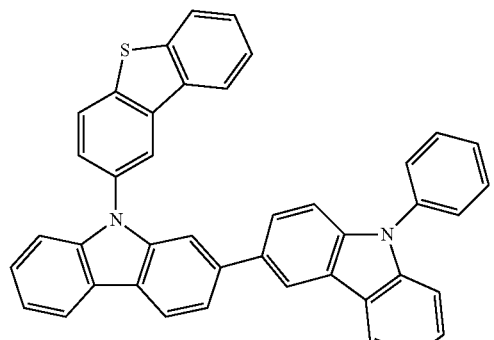

-continued
[E-87]
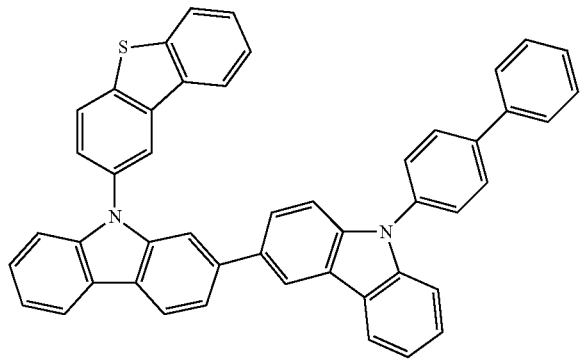
[E-88]
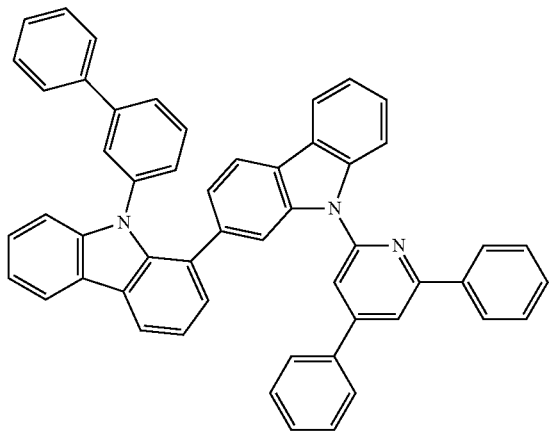
[E-89]
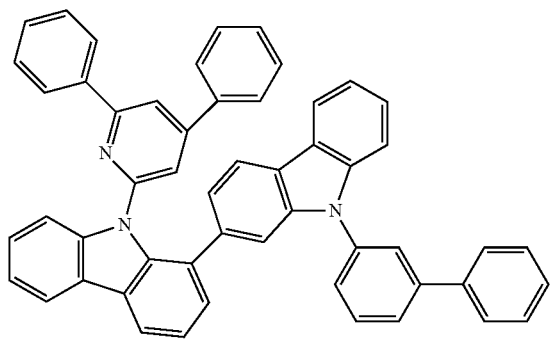
[E-90]
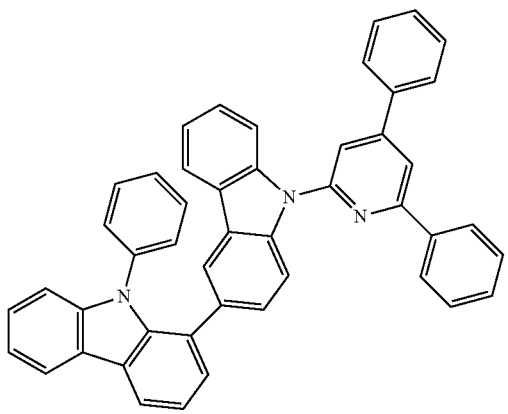
[E-91]
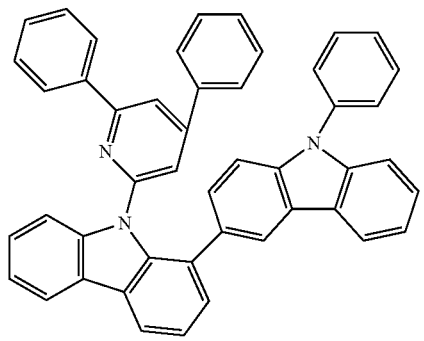
[E-92]
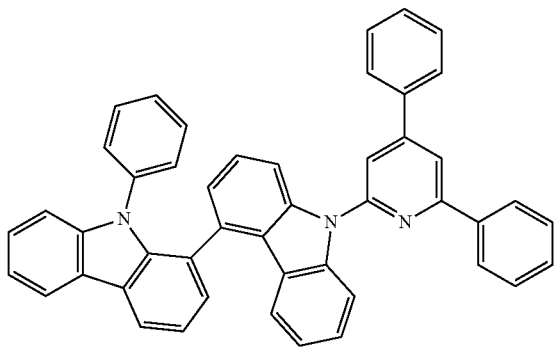
[E-93]
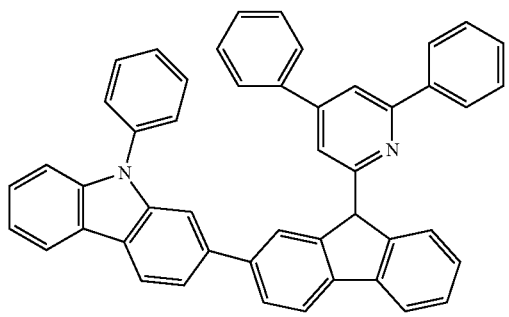
[E-94]
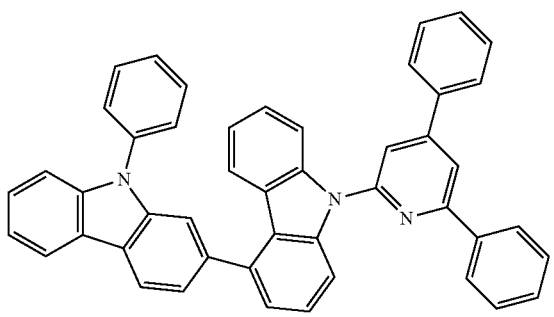

[E-95] 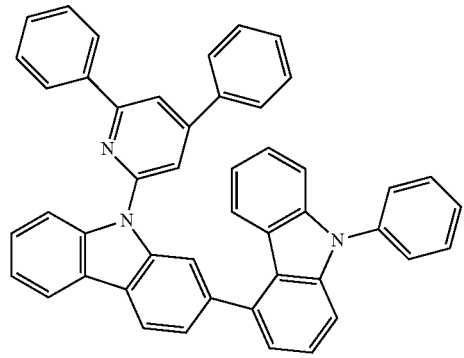
[E-96] 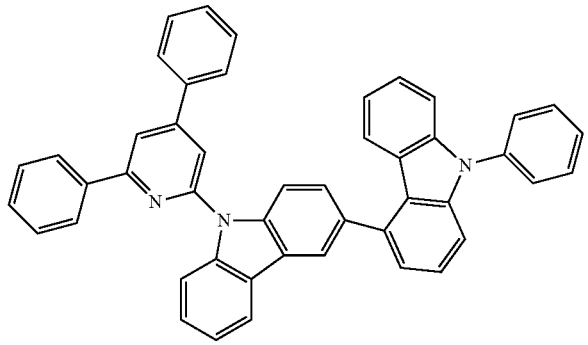
[E-97] 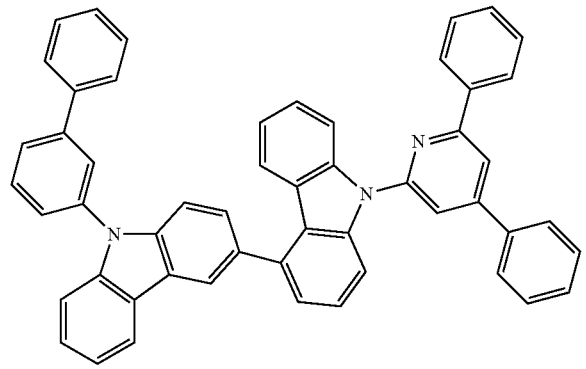
[E-98] 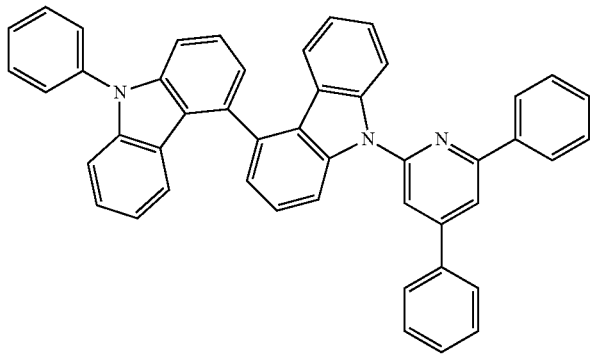
[E-99] 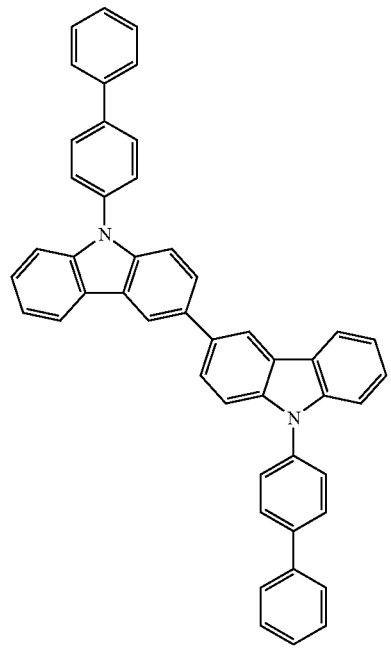
[E-100] 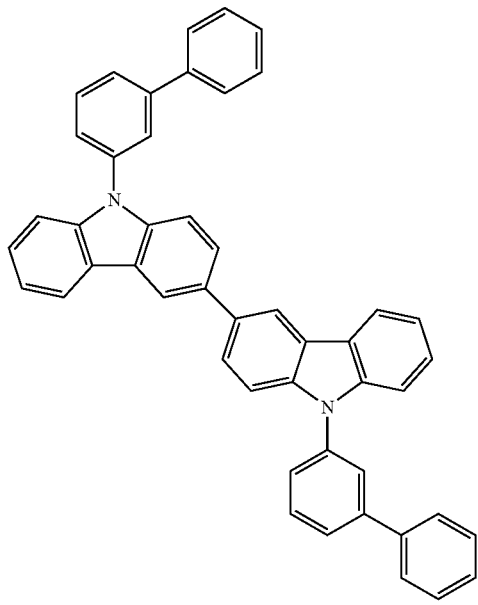

-continued
[E-101]
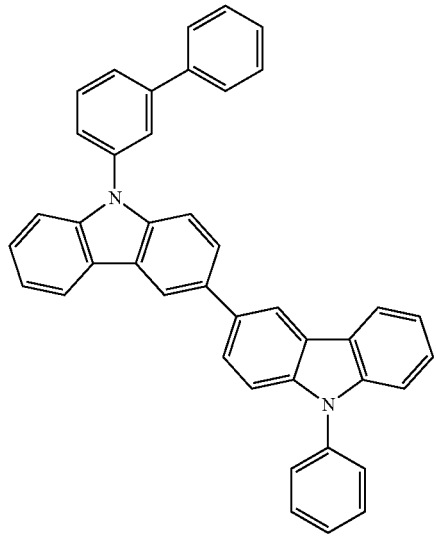
[E-102]
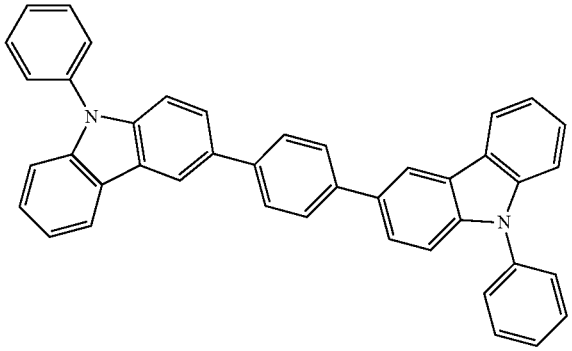
[E-103]
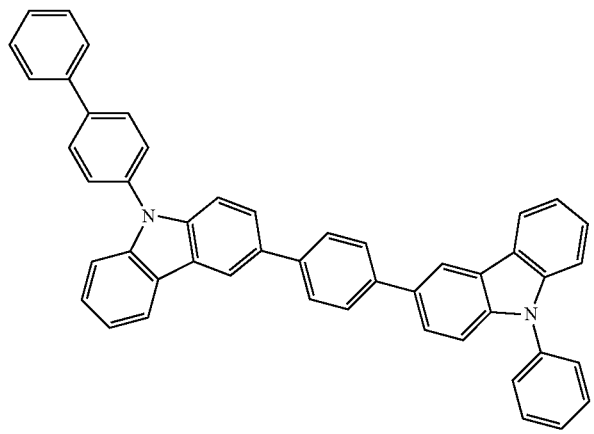
[E-104]
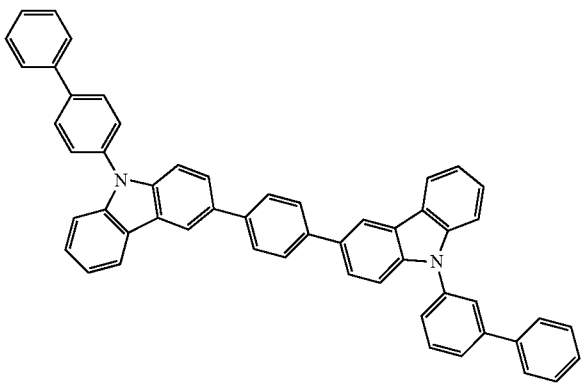
[E-105]
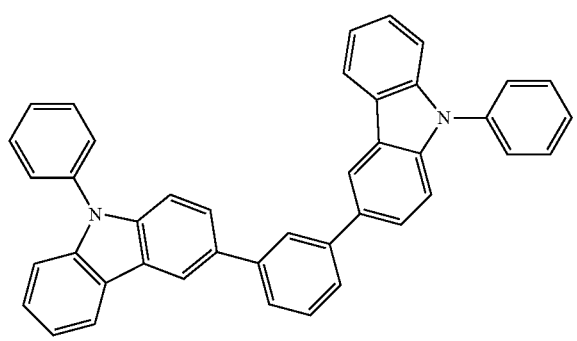
[E-106]
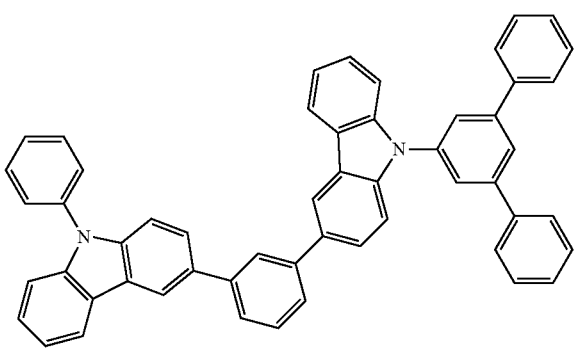

[E-107]
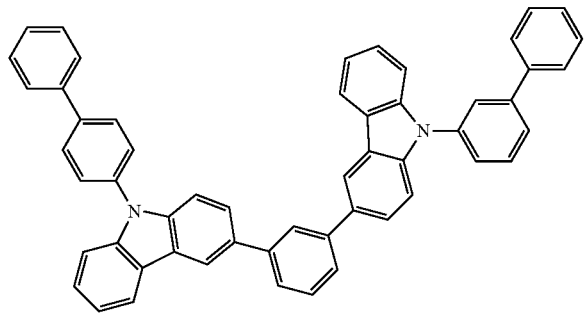
[E-108]
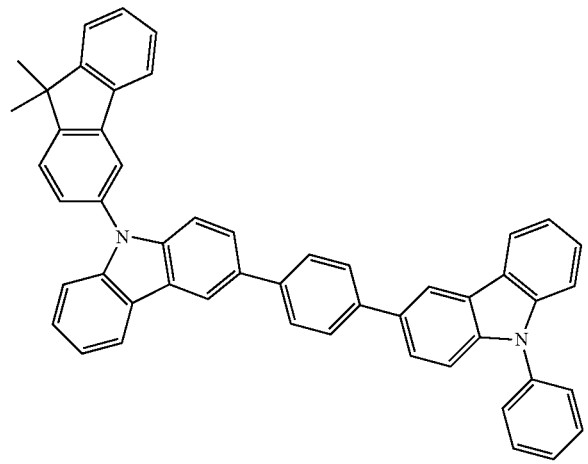
[E-109]
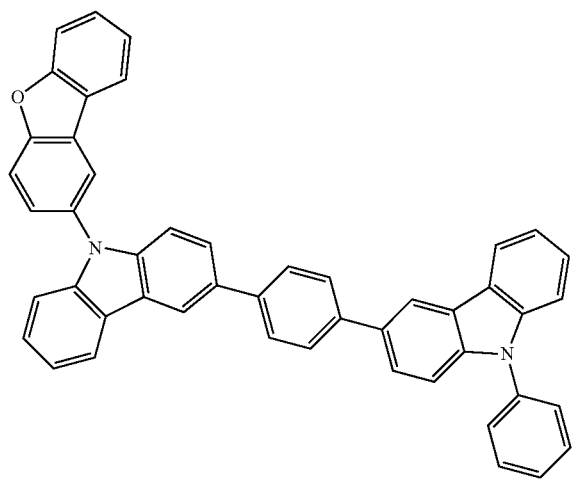
[E-110]
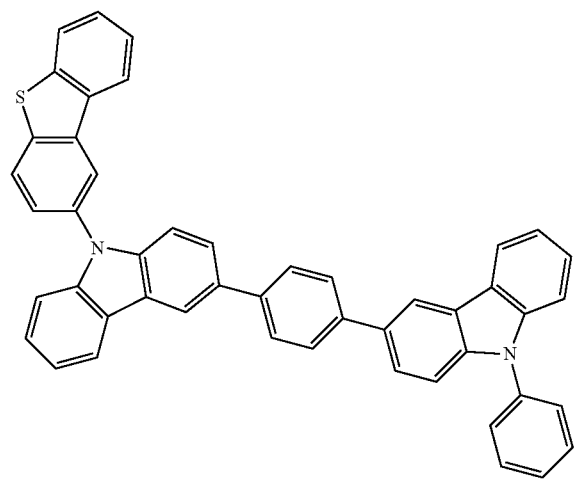
[E-111]
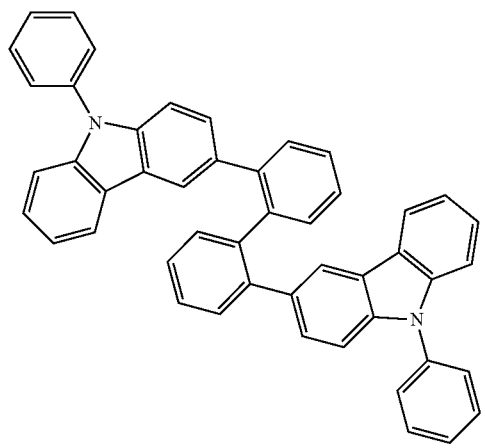
[E-112]
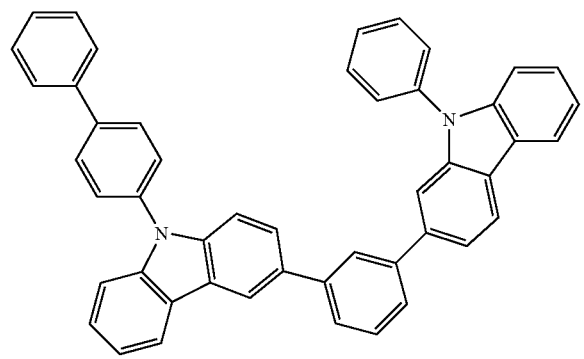

[E-113]
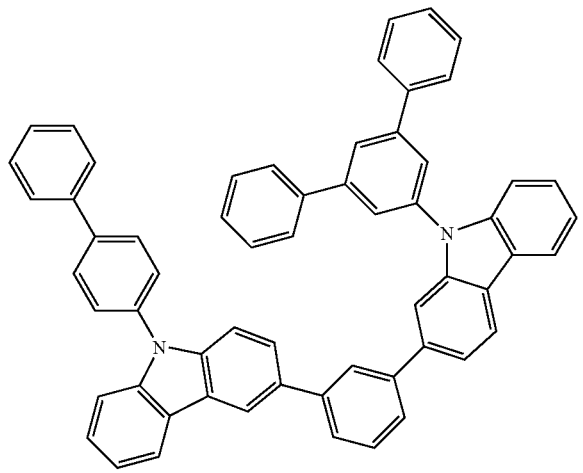
[E-114]
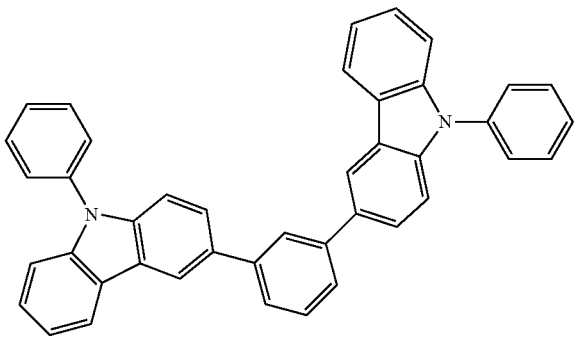
[E-115]
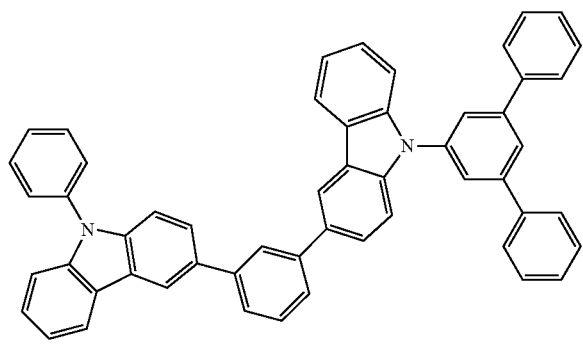
[E-116]
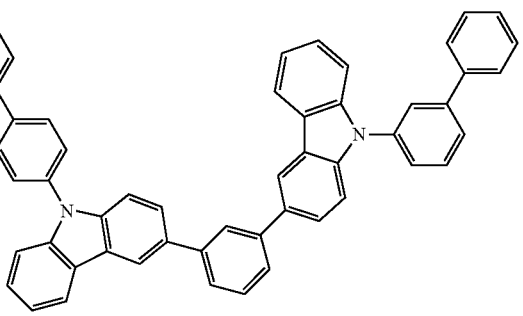
[E-117]
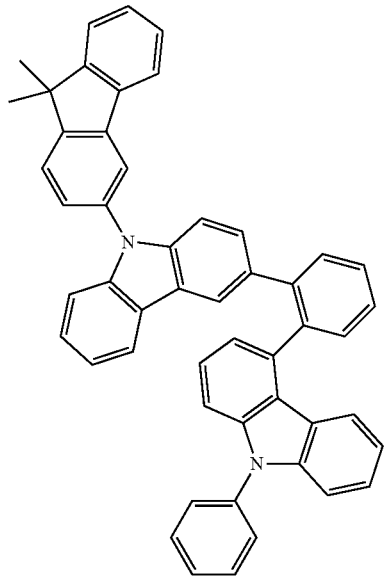
[E-118]
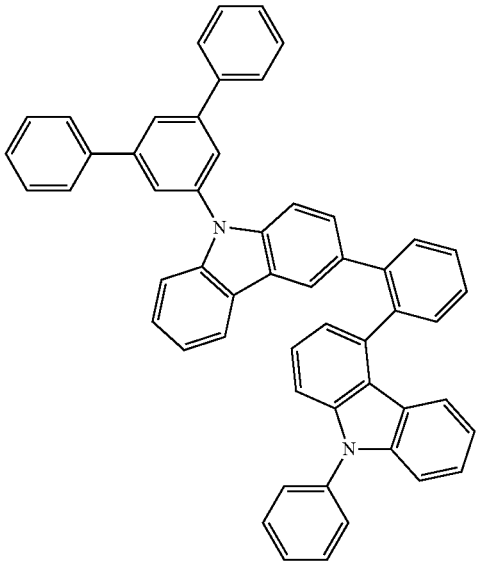

-continued
[E-119]
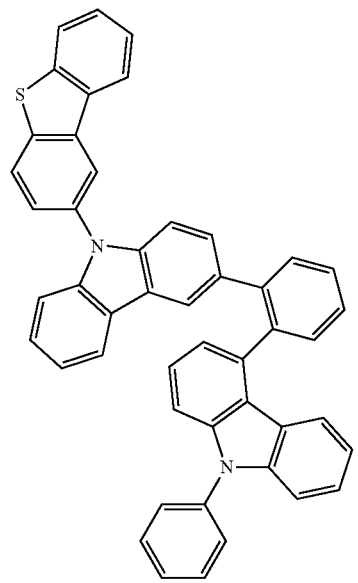
[E-120]
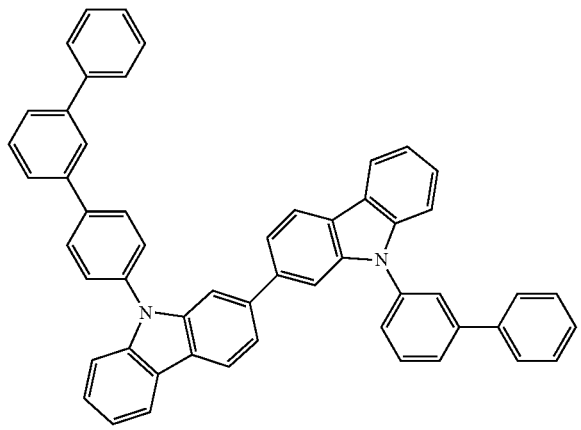
[E-121]
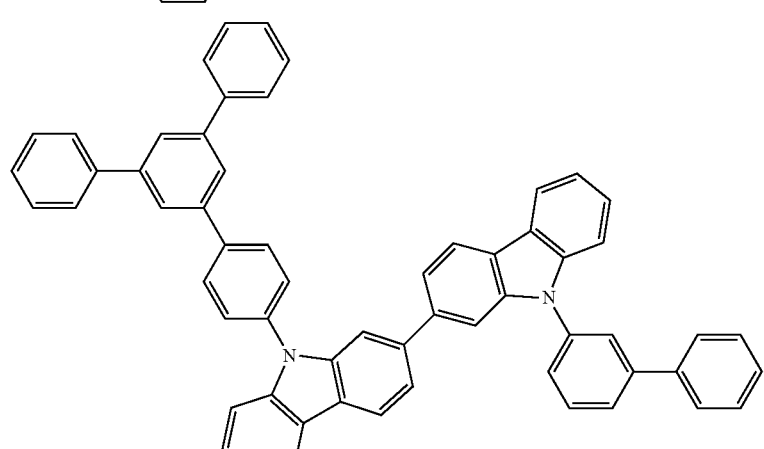
[E-122]
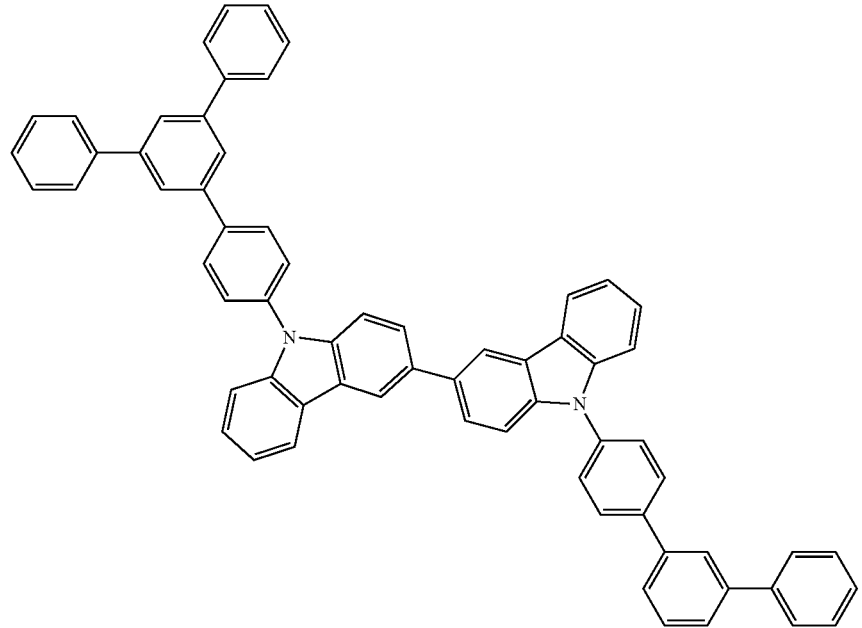

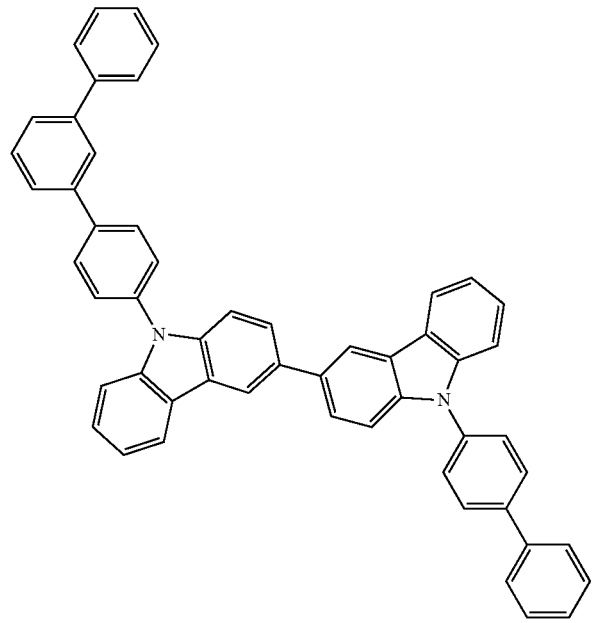
[E-123]
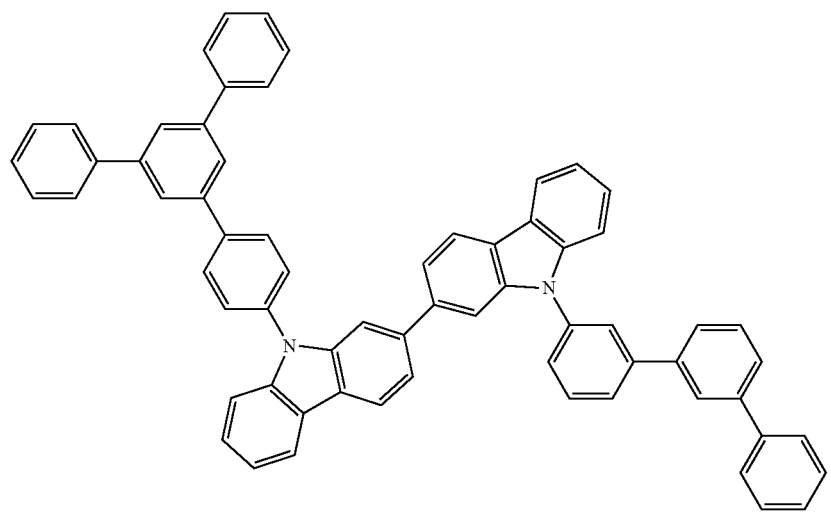
[E-124]

[E-125]
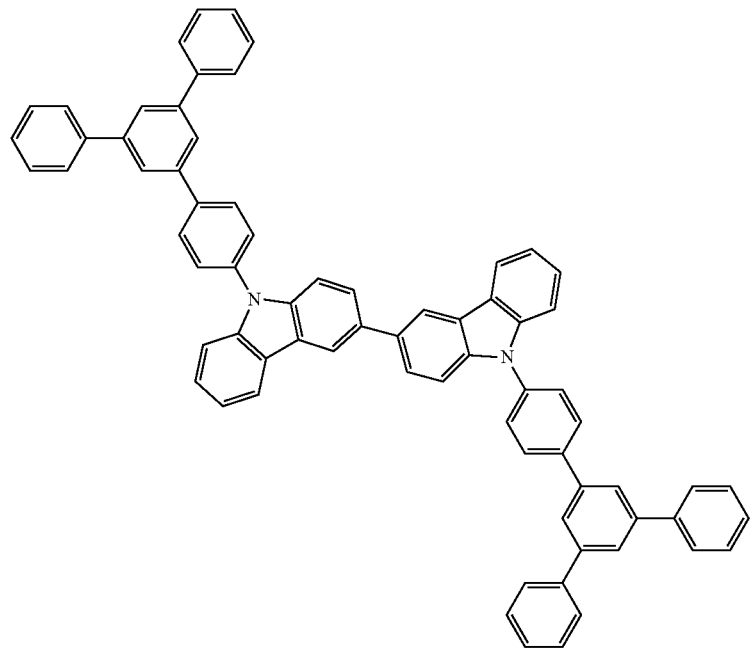
[E-126] [E-127]
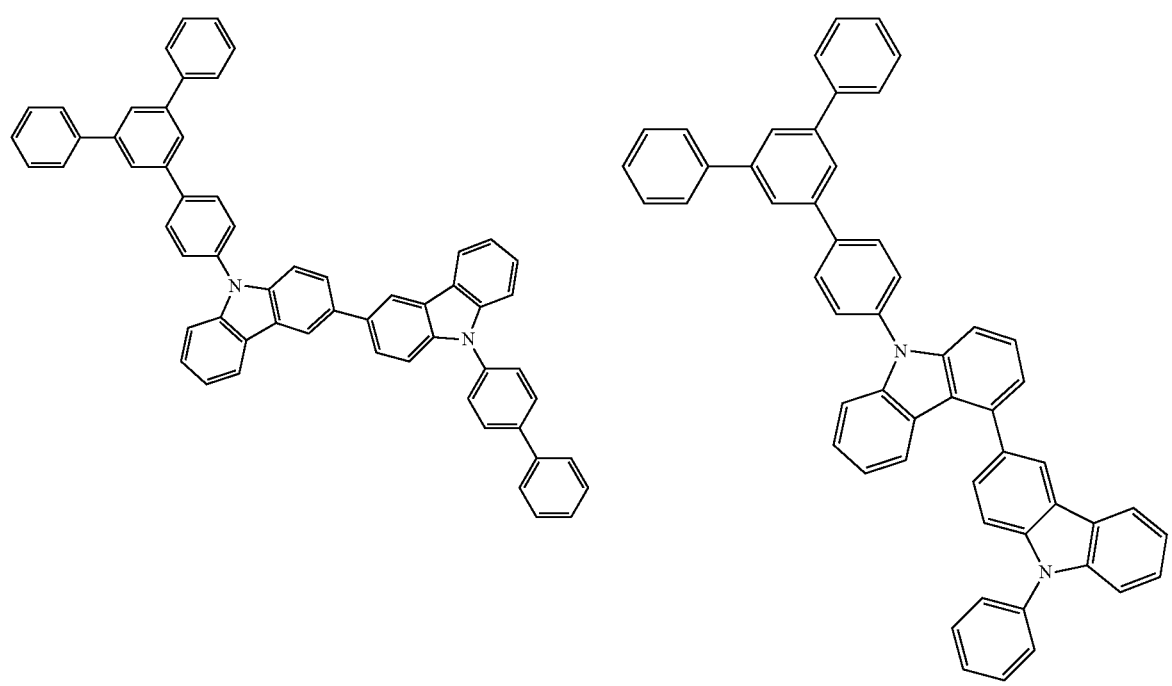

[E-128]
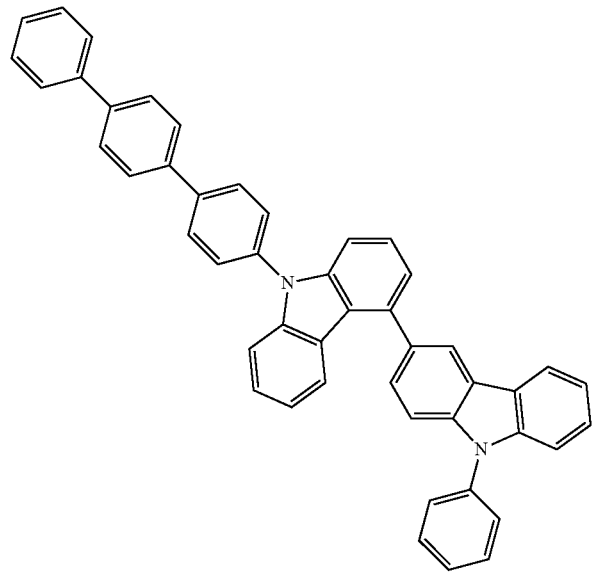
[E-129]
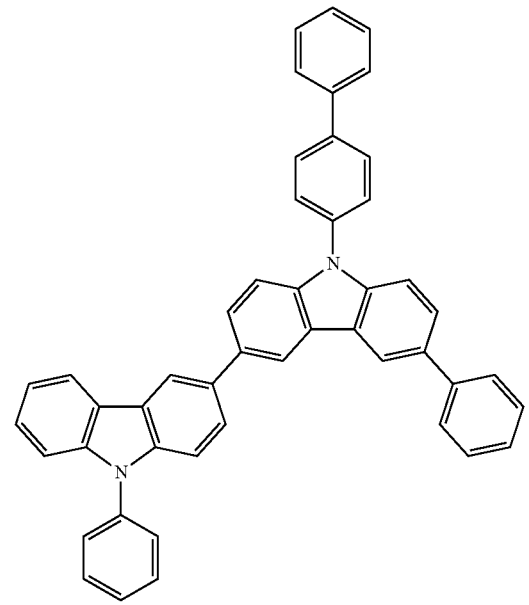
[E-130]
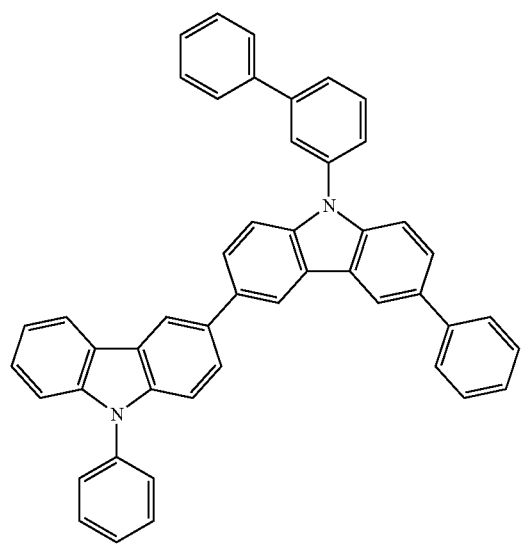
[E-131]
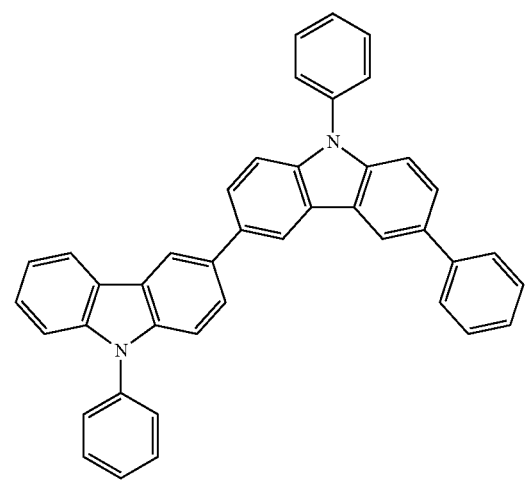

[E-132]
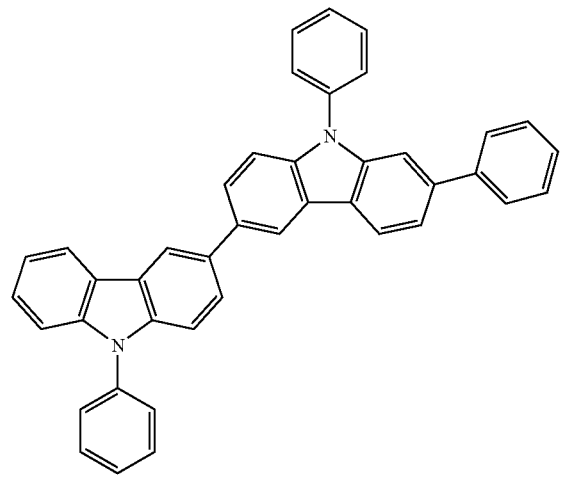
[E-133]
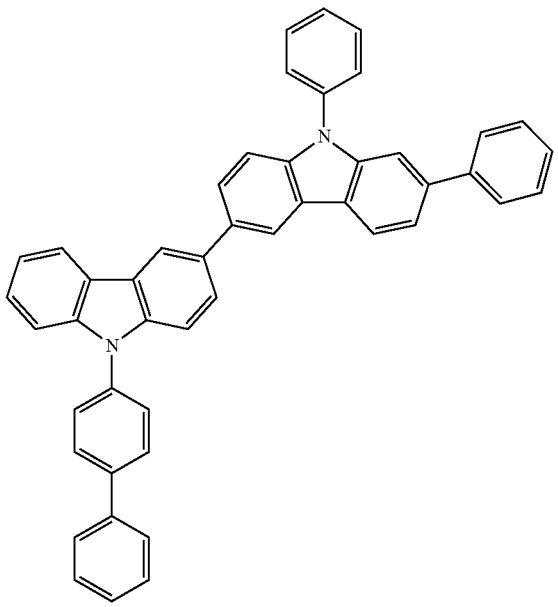
[E-134]
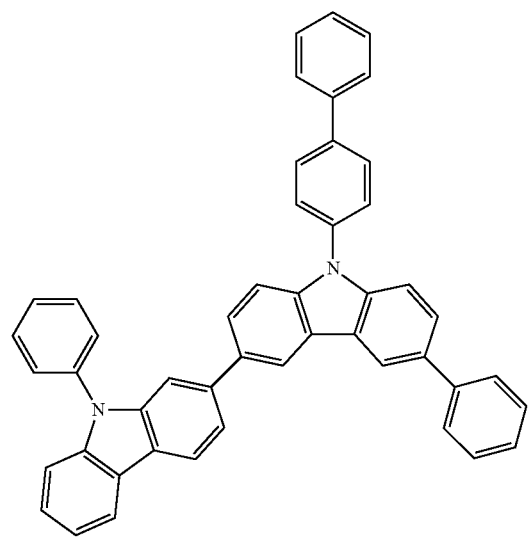
[E-135]
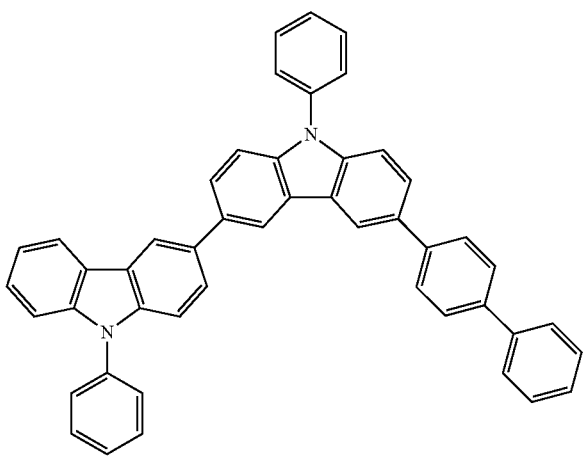

-continued

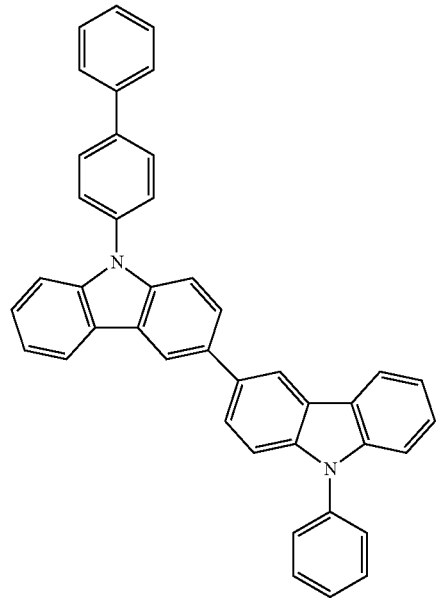
[E-136]

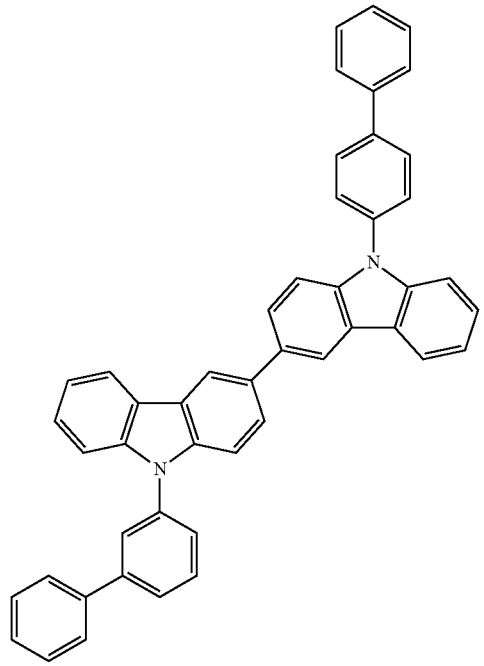
[E-137]

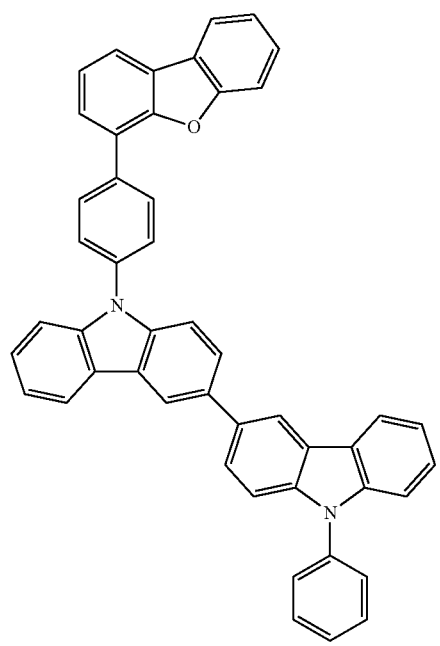
[E-138]

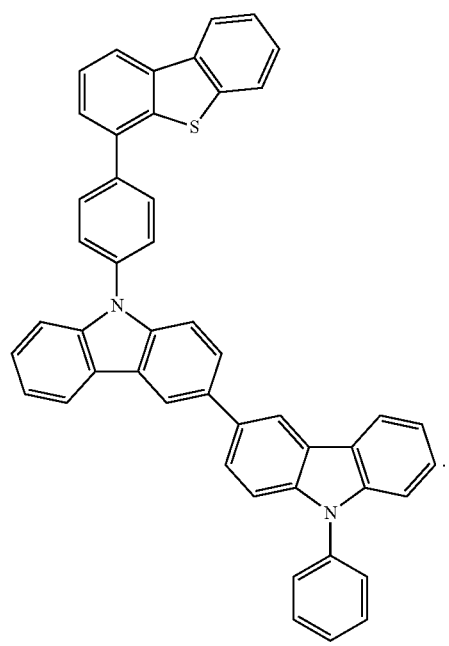
[E-139]

The aforementioned first host compound and second host compound may variously be combined to prepare various compositions.

The composition according to an embodiment of the present invention may include the compound represented by Chemical Formula 1A-II as a first host and Compound C-8 of Group II as a second host.

For example, *—Y$^1$-A$^1$ and *—Y$^2$-A$^2$ of Chemical Formula 2 may be selected from B-1 to B-3 of Group III.

The second compound for an organic optoelectronic diode is used with the first compound for an organic optoelectronic diode in the light emitting layer and increases charge mobility and stability, and thereby luminous efficiency and life-span characteristics may be improved. In addition, a ratio of the second compound for an organic optoelectronic diode and the first compound for an organic optoelectronic diode may be adjusted and thereby charge mobility may be controlled. When the composition of the present invention is used as a host, a combination ratio thereof may be different according to types and properties of a used dopant or when the composition of the present invention is used in an electron transport auxiliary layer, a combination ratio of compounds in the composition may be different according to types of a host and a dopant of an EML layer of an OLED device. For example, they may be included in a weight ratio of about 1:9 to 9:1, specifically 1:9 to 8:2, 1:9 to 7:3, 1:9 to 6:4, or 1:9 to 5:5, 2:8 to 8:2, 2:8 to 7:3, 2:8 to 6:4, or 2:8 to 5:5.

In addition, when the composition of the present invention is used as a host, the first compound for an organic optoelectronic diode and the second compound for an organic optoelectronic diode may be included in a weight ratio of 1:9 to 5:5, 2:8 to 5:5, or 3:7 to 5:5. For example, the first compound for an organic optoelectronic diode and the second compound for an organic optoelectronic diode may be included in a weight ratio of 5:5 or 3:7. Within the ranges, efficiency and life-span may be simultaneously improved.

The composition may further include at least one organic compound in addition to the aforementioned first compound for an organic optoelectronic diode and second compound for an organic optoelectronic diode.

The compound for an organic optoelectronic diode or the composition for an organic optoelectronic diode may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more types thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

In an embodiment of the present invention, the phosphorescent dopant may be a green phosphorescent dopant, for example an Ir complex compound such as $Ir(ppy)_3$. Herein, a wavelength range of the green phosphorescent dopant may be 500 nm to 550 nm.

Hereinafter, an organic optoelectronic diode including the compound for an organic optoelectronic diode or the composition for an organic optoelectronic diode is described.

An organic optoelectronic diode according to another embodiment includes an anode and a cathode facing each other and at least one organic layer disposed between the anode and the cathode, wherein the organic layer includes the compound for an organic optoelectronic diode or the composition for an organic optoelectronic diode.

For example, the organic layer may include a light emitting layer and the light emitting layer may include the compound for an organic optoelectronic diode or the composition for an organic optoelectronic diode of the present invention.

Specifically, the compound for an organic optoelectronic diode or the composition for an organic optoelectronic diode may be included as a host, for example a green host of the light emitting layer.

A maximum light emitting wavelength of the organic optoelectronic diode according to an embodiment of the present invention may be 500 nm to 550 nm.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic diode or the composition for an organic optoelectronic diode.

The organic optoelectronic diode may be any diode to convert electrical energy into photoenergy and vice versa without particular limitation, and may be, for example an organic photoelectric diode, an organic light emitting diode, an organic solar cell, and an organic photo conductor drum.

Herein, an organic light emitting diode as one example of an organic optoelectronic diode is described referring to drawings.

FIGS. 1 and 2 are cross-sectional views of an organic light emitting diode according to embodiments.

Referring to FIG. 1, an organic light emitting diode 100 according to an embodiment includes an anode 120 and a cathode 110 facing each other and an organic layer 105 interposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al and $BaF_2$/Ca, but is not limited thereto.

The organic layer 105 includes a light emitting layer 130 including the aforementioned compound for an organic optoelectronic diode.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic diode of the present invention may be included in the organic layer. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there are no particular descriptions or were synthesized by known methods.

(Preparation of Compound for Organic Optoelectronic Diode)

The compound as one specific examples of the present invention was synthesized through the following steps.

(First Compound for Organic Optoelectronic Diode)

Synthesis of Intermediate

Synthesis Example 1: Synthesis of Intermediate A

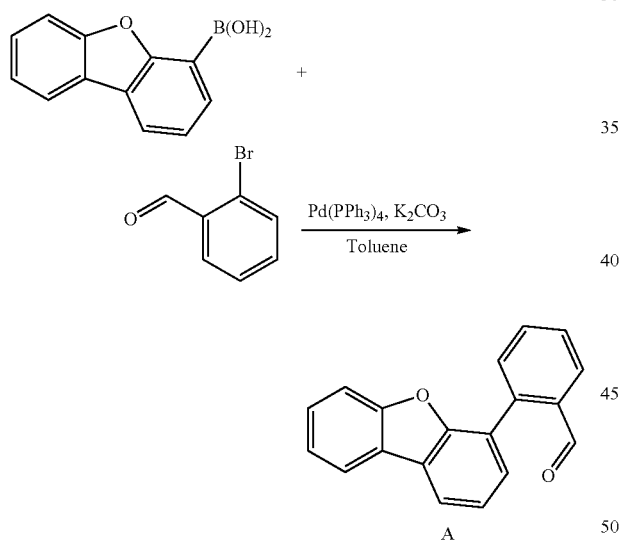

37.81 g (178.36 mmol) of 4-dibenzofuranboronic acid, 30 g (162.14 mmol) of 2-bromobenzaldehyde, 5.62 g (4.86 mmol) of tetrakis(triphenylphosphine) palladium (0), and 44.82 g (324.29 mmol) of potassium carbonate were suspended in 500 ml of toluene and 250 ml of distilled water in a round-bottomed flask and then, refluxed and stirred for 12 hours. When a reaction was complete, the resultant was cooled to room temperature and then extracted. Subsequently, an organic layer obtained therefrom was silica gel filtered and concentrated, methyl alcohol was added thereto to generate a solid, and the solid was filtered and washed to obtain 39.87 g of Intermediate A (a yield of 82%).

LC-Mass (theoretical value: 272.30 g/mol, measured value: M+=272 g/mol)

Synthesis Example 2: Synthesis of Intermediate B

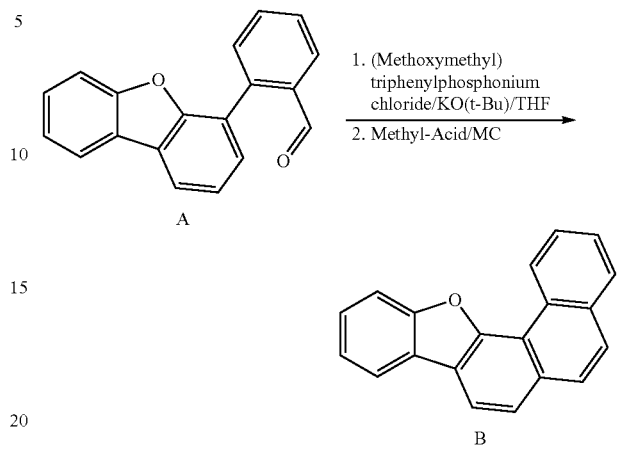

39.87 g (146.42 mmol) of Intermediate A synthesized according to Synthesis Example 1 and 55.21 g (161.06 mmol) of (methoxymethyl)triphenyl phosphonium chloride were suspended in 500 ml of tetrahydrofuran in a round-bottomed flask and then, maintained at 0° C. Subsequently, 19.72 g (175.70 mmol) of potassium t-butoxide was slowly added thereto at 0° C. and then, stirred for 12 hours. When a reaction was complete, an extraction was performed after adding 600 ml of distilled water thereto, an extract therefrom was concentrated and suspended in 500 ml of methylenechloride, dried with magnesium sulfate and filtered with silica gel, and then, concentrated again. The concentrated reaction solution was dissolved in 200 ml of methylenechloride, 15 g of methanesulfonic acid was slowly added thereto, and the obtained mixture was stirred at room temperature for 12 hours. When a reaction was complete, a solid generated therein was filtered, washed with 200 ml of distilled water and 200 ml of methanol, and dried to obtain 24.34 g of Intermediate B (a yield of 62%).

LC-Mass (theoretical value: 272.30 g/mol, measured value: M+=272 g/mol)

Synthesis Example 3: Synthesis of Intermediate C

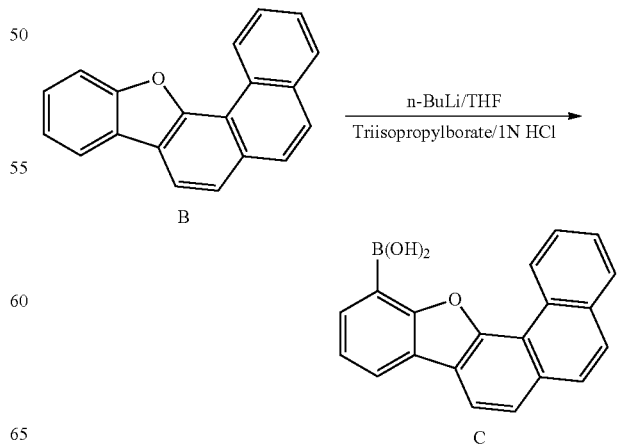

24.34 g (90.72 mmol) of Intermediate B synthesized according to Synthesis Example 2 was dissolved in 250 ml of THF and cooled down to −78° C. 43.5 ml (108.86 mmol) of n-BuLi (2.5 M in Hex) was added thereto in a dropwise fashion and then, stirred at room temperature for 16 hours. The resultant was cooled down to −78° C., 25 ml (108.86 mmol) of triisopropylborate was added thereto, and the obtained mixture was stirred at room temperature for 12 hours. When a reaction was complete, iN HCl was added thereto, the obtained mixture was stirred for one hour, and a solid generated therein was filtered and washed with distilled water and acetone to obtain 22 g of Intermediate C (a yield of 78%).

LC-Mass (theoretical value: 312.13 g/mol, measured value: M+=312 g/mol)

Synthesis Example 4: Synthesis of Intermediate D

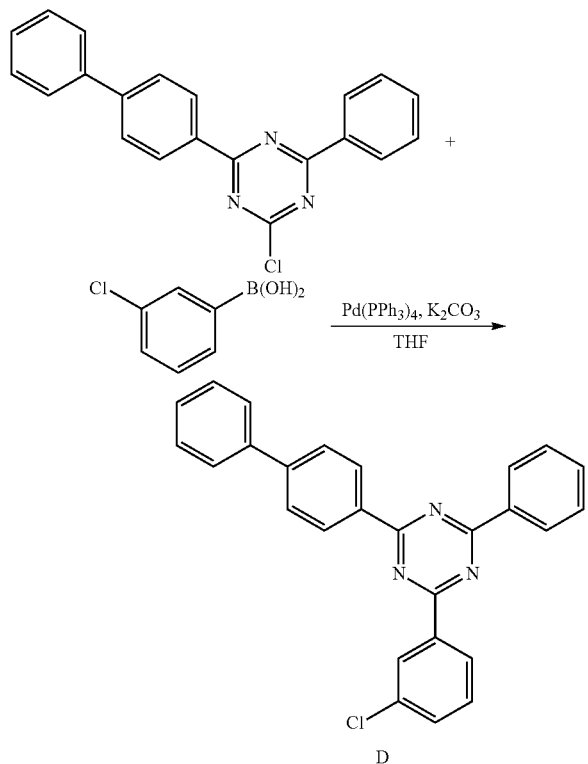

D 30 g (87.26 mmol) of 2-([1,1'-biphenyl]-4-yl)-4-chloro-6-phenyl-1,3,5-triazine, 14.33 g (91.62 mmol) of (3-chlorophenyl)boronic acid, 3.02 g (2.62 mmol) of tetrakis(triphenylphosphine) palladium (0), and 24.12 g (174.52 mmol) of potassium carbonate were suspended in 435 ml of tetrahydrofuran and 200 ml of distilled water in a round-bottomed flask and then, refluxed and stirred for 12 hours. When a reaction was complete, the resultant was cooled down to room temperature and then extracted. Subsequently, an organic layer obtained therefrom was silica gel filtered and concentrated, methyl alcohol was added thereto to generate a solid, and the solid was filtered and washed to obtain 28 g of Intermediate D (a yield of 76%).

LC-Mass (theoretical value: 419.90 g/mol, measured value: M+=419 g/mol)

Synthesis Example 5: Synthesis of Intermediate E

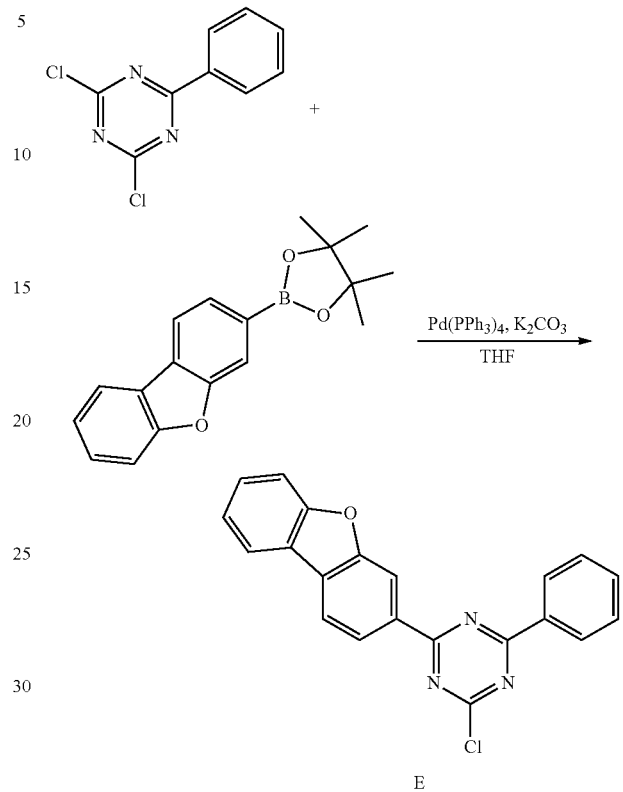

E 10 g (44.24 mmol) of 2,4-dichloro-6-phenyl-1,3,5-triazine, 15.61 g (53.08 mmol) of 2-(dibenzo[b,d]furan-3-yl)-4,4,5,5-tetramethyl-1,3,2-dioxaborolane, 1.53 g (1.33 mmol) of tetrakis(triphenylphosphine)palladium (0), and 12.22 g (88.48 mmol) of potassium carbonate were suspended in 200 ml of THF and 100 ml of distilled water in a round-bottomed flask and then, refluxed and stirred for 12 hours. When a reaction was complete, a solid generated therein was filtered and purified through silica gel column to obtain 6.0 g of Compound E as a desired compound (a yield of 38%).

LC-Mass (theoretical value: 357.79 g/mol, measured value: M+=0.357 g/mol)

Synthesis Example 6: Synthesis of Intermediate F

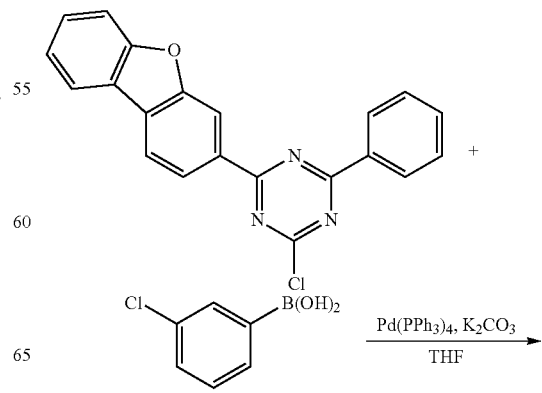

-continued

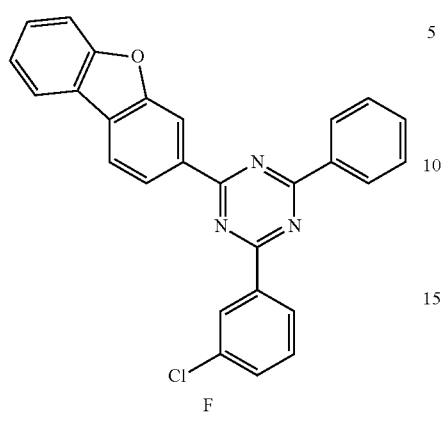

F 5.8 g of Compound F (a yield of 80%) was synthesized according to the same method as Synthesis Example 4 except that 6.0 g (16.77 mmol) of 2-chloro-4-(dibenzo[b,d]furan-3-yl)-6-phenyl-1,3,5-triazine, 2.88 g (18.45 mmol) of (3-chlorophenyl)boronic acid, 0.58 g (0.50 mmol) of tetrakis (triphenylphosphine)palladium (0), and 4.63 g (33.54 mmol) of potassium carbonate were suspended in 80 ml of THF and 40 ml of distilled water in a round-bottomed flask.

LC-Mass (theoretical value: 433.89 g/mol, measured value: M+=433 g/mol)

Synthesis Example 7: Synthesis of Compound 26

6 g (19.22 mmol) of Compound C synthesized according to Synthesis Example 3, 8.48 g (20.18 mmol) of Compound D synthesized according to Synthesis Example 4, 0.55 g (0.96 mmol) of Pd(dba)$_2$, 0.4 g (1.92 mmol) of P(t-Bu)$_3$, and 12.52 g (38.44 mmol) of Cs$_2$CO$_3$ were suspended in 100 ml of 1,4-dioxane in a round-bottomed flask and then, refluxed and stirred for 12 hours. When a reaction was complete, the resultant was cooled down to room temperature, distilled water was added thereto, and a solid generated therein was filtered and washed again with distilled water/acetone/MeOH, sequentially. Then, the solid was recrystallized with toluene to obtain 7.0 g of Compound 26 (a yield of 56%) as a desired compound.

LC-Mass (theoretical value: 651.75 g/mol, measured value: M+=651 g/mol)

Synthesis Example 8: Synthesis of Compound 27

5.6 g of Compound 27 (a yield of 66%) was synthesized according to the same method as Synthesis Example 7 except that 4 g (12.82 mmol) of Compound C according to Synthesis Example 3 and 5.8 g (13.45 mmol) of Compound F according to Synthesis Example 6 were put in a round-bottomed flask.

LC-Mass (theoretical value: 665.74 g/mol, measured value: M+=665 g/mol)

Comparison of T1 of Comparative Compound and Compound of the Present Invention by Simulation

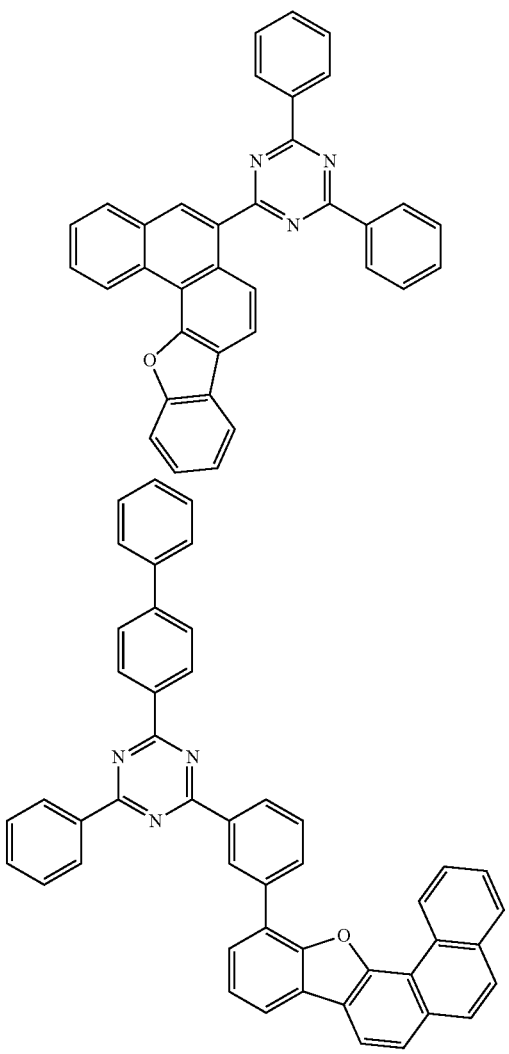

T1 (simulation)=2.4 eV Compound 26 T1 (simulation)=2.61 eV (Manufacture of Organic Light Emitting Diode)

Example 1

A glass substrate coated with ITO (indium tin oxide) as a 1500 Å-thick thin film was ultrasonic wave-washed with distilled water. After washed with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing Compound A, and a hole transport layer was formed on the injection layer by depositing Compound B to be 50 Å thick and Compound C to be 1020 Å thick. On the hole transport layer, a 400 Å-thick light emitting layer was formed by vacuum-depositing Compound 26 of Synthesis Example 7 as a host and being doped with 10 wt % of tris(2-phenylpyridine)iridium (III) [Ir(ppy)$_3$] as a dopant. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows.

A structure of ITO/Compound A (700 Å)/Compound B (50 Å)/Compound C (1020 Å)/EML [Compound 26: Ir(ppy)$_3$=90 wt %:10 wt %] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 2 and Comparative Example 1

The diodes according to Example 2 and Comparative Example I were manufactured in the same method as Example 1 except that Compound 27 (Example 2) or CBP alone was used respectively instead of Compound 26.

Example 3

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing N4,N4'-diphenyl-N4,N4'-bis (9-phenyl-9H-carbazol-3-yl)biphenyl-4,4'-diamine (Compound A), and a hole transport layer was formed by depositing 1,4,5,8,9,11-hexaazatriphenylene-hexacarbonitrile (HAT-CN) (Compound B) in a thickness of 50 Å on the injection layer, and depositing N-(biphenyl-4-yl)-9,9-dimethyl-N-(4-(9-phenyl-9H-carbazol-3-yl)phenyl)-9H-fluoren-2-amine (Compound C) in a thickness of 1020 Å. On the hole transport layer, a 400 Å-thick light emitting layer was formed by vacuum-depositing Compound 26 and Compound E-137 simultaneously as a host and tris(4-methyl-2,5-diphenylpyridine)iridium(III) (Compound D) as a dopant in a doping amount of 10 wt %. Herein, Compound 26 and Compound E-137 were used in a ratio of 3:7.

Subsequently, a 300 Å-thick electron transport layer was formed by vacuum-depositing 8-(4-(4-(naphthalen-2-yl)-6-(naphthalen-3-yl)-1,3,5-triazin-2-yl)phenyl)quinoline (Compound E) and Liq simultaneously in a 1:1 ratio on the light emitting layer, and Liq (15 Å) and Al (1200 Å) were sequentially vacuum-deposited on the electron transport layer to form a cathode, manufacturing an organic light emitting diode.

The organic light emitting diode has five organic thin layers, specifically

ITO/A (700 Å)/B (50 Å)/C (1020 Å)/EML[Compound 26:E-137:D=X:X:10%] (400 Å)/E:Liq (300 Å)/Liq (15 Å)/Al (1200 Å).

(X=a weight ratio)

Example 4 to Example 6

Organic light emitting diodes according to Examples 4 to 6 were manufactured by using the first host, the second host, and a weight ratio thereof as shown in Table 1.
Evaluation Luminous efficiency and life-span characteristics of the organic light emitting diodes according to Examples 1 to 6 and Comparative Example 1 were evaluated. Specific measurement methods are as follows, and the results are shown in Table 1.

(1) Measurement of Current Density Change Depending on Voltage Change

The obtained organic light emitting diodes were measured regarding a current value flowing in the unit diode, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T97 life-spans of the organic light emitting diodes according to Examples 1 to 6 and Comparative Example 1 were measured as a time when their luminance decreased down to 97% relative to the initial luminance after emitting light with 5000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$.

TABLE 1

| Examples | First host | Second host | First host: Second host (wt/wt) | Driving voltage (V) | Luminous efficiency (cd/A) | Life-spanT 97 (h) |
|---|---|---|---|---|---|---|
| Example 1 | Compound 26 | — | — | 4.56 | 65.4 | 100 |
| Example 2 | Compound 27 | — | — | 4.12 | 66.7 | 120 |
| Example 3 | Compound 26 | E-137 | 3:7 | 4.16 | 69.2 | 280 |
| Example 4 | Compound 27 | E-137 | 3:7 | 4.02 | 69.1 | 300 |
| Example 5 | Compound 26 | E-137 | 5:5 | 4.04 | 73.0 | 350 |
| Example 6 | Compound 27 | E-137 | 5:5 | 3.96 | 72.7 | 370 |
| Comparative Example 1 | CBP | — | — | 7.20 | 19.5 | 1 |

Referring to Table 1, the organic light emitting diodes according to Examples 1 to 6 exhibited remarkably improved driving voltage, luminous efficiency, and life-span characteristics simultaneously compared with the organic light emitting diode of Comparative Example 1.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS 100, 200: organic light emitting diode
105: organic layer
110: cathode
120: anode
130: light emitting layer
140: hole auxiliary layer

The invention claimed is:

1. A compound for an organic optoelectronic diode represented by Chemical Formula 1A-I, Chemical Formula 1A-II, or Chemical Formula 1A-III,

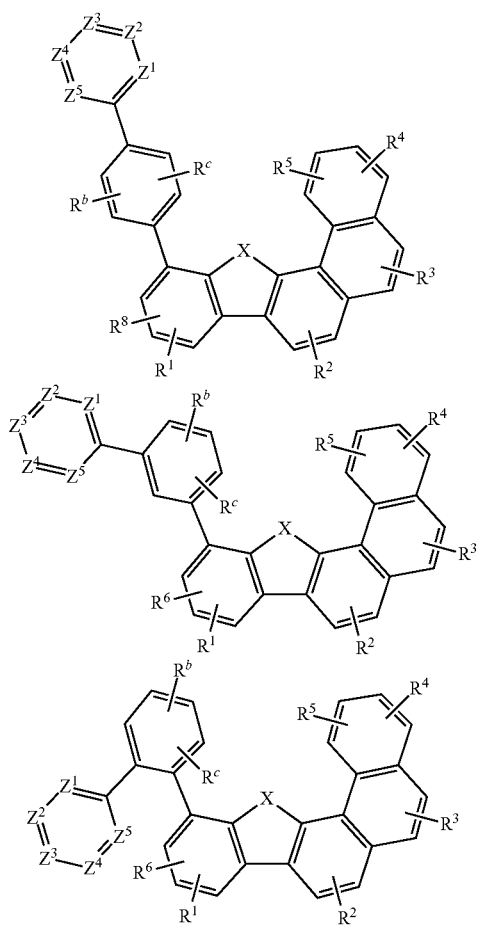

wherein, in Chemical Formula 1A-I, Chemical Formula 1A-II, and Chemical Formula 1A-III,
$Z^1$ to $Z^5$ are independently N or $CR^a$,
at least one of $Z^1$ to $Z^5$ is N,
X is O or S,
$R^b$, $R^c$, and $R^1$ to $R^6$ are independently hydrogen, deuterium, a substituted or unsubstituted C1 to C10 alkyl group, or a substituted or unsubstituted C6 to C18 aryl group,
each $R^a$ is independently hydrogen, deuterium, a substituted or unsubstituted C1 to C10 alkyl group, a substituted or unsubstituted C6 to C18 aryl group, or a substituted or unsubstituted C2 to C20 heterocyclic group,
each $R^a$ is independently present or adjacent ones thereof are linked with each other to form a substituted or unsubstituted aliphatic, aromatic, or heteroaromatic monocyclic or polycyclic ring, and
the "substituted" refers to replacement of at least one hydrogen by deuterium, a cyano group, a C1 to C20 alkyl group, a C6 to C30 aryl group, or a C2 to C30 heteroaryl group.

2. The compound for an organic optoelectronic diode of claim 1, wherein moiety

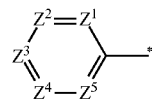

of Chemical Formula 1A-I, Chemical Formula 1A-II, and Chemical Formula 1A-III is a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuranpyridinyl group, a substituted or unsubstituted benzofuranpyrimidinyl group, a substituted or unsubstituted benzothiophenepyridinyl group, a substituted or unsubstituted benzothiophenepyrimidinyl group, or a combination thereof.

3. The compound for an organic optoelectronic diode of claim 1, wherein moiety

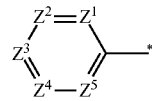

of Chemical Formula 1A-I, Chemical Formula 1A-II, and Chemical Formula 1A-III is selected from substituents of Group I:

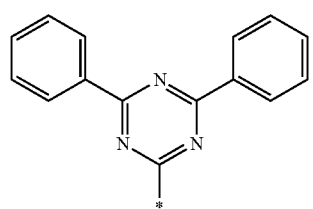

[Group I]

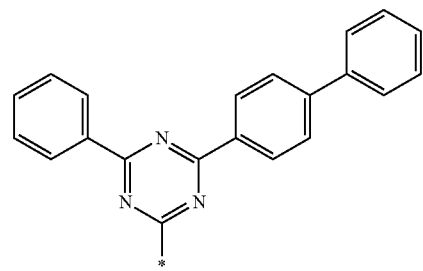
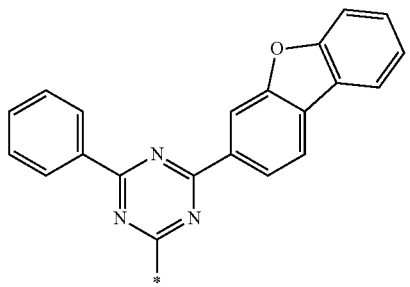
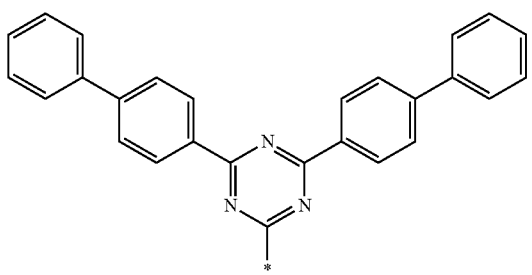
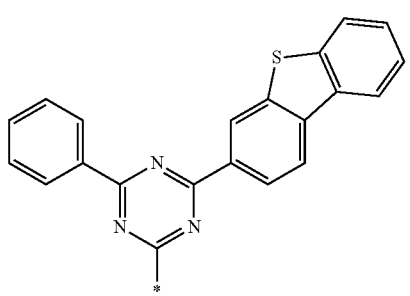
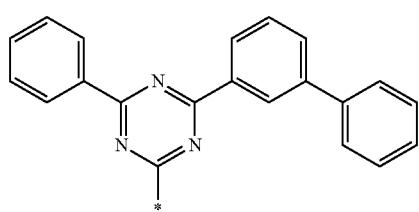
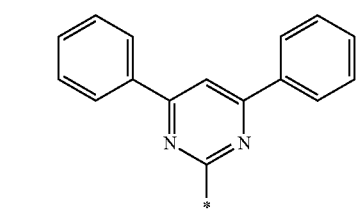
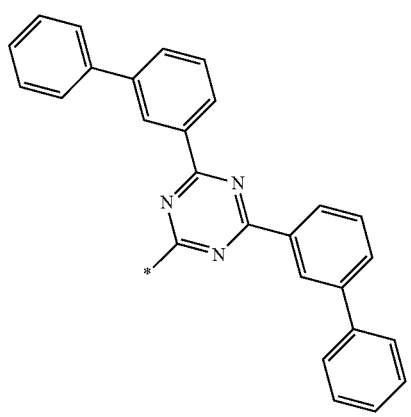
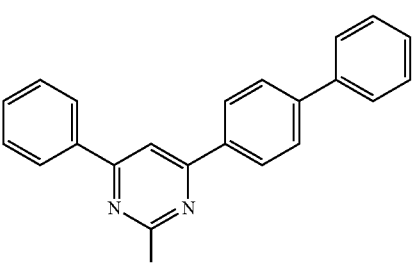
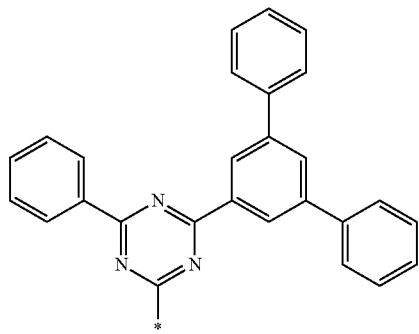
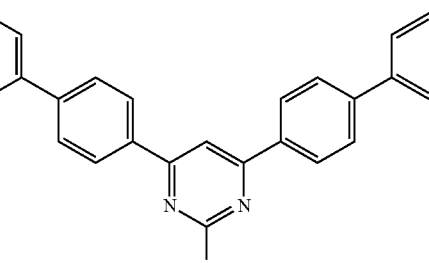
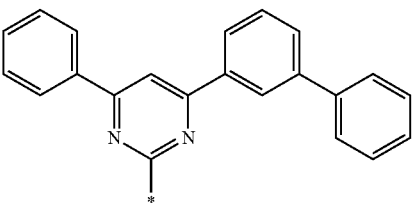

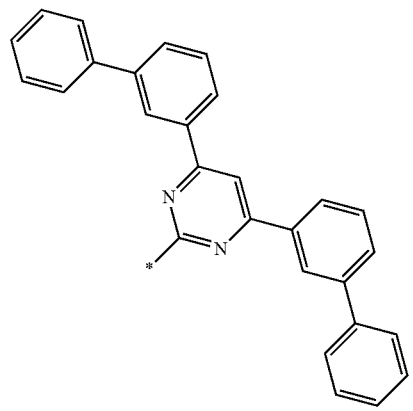
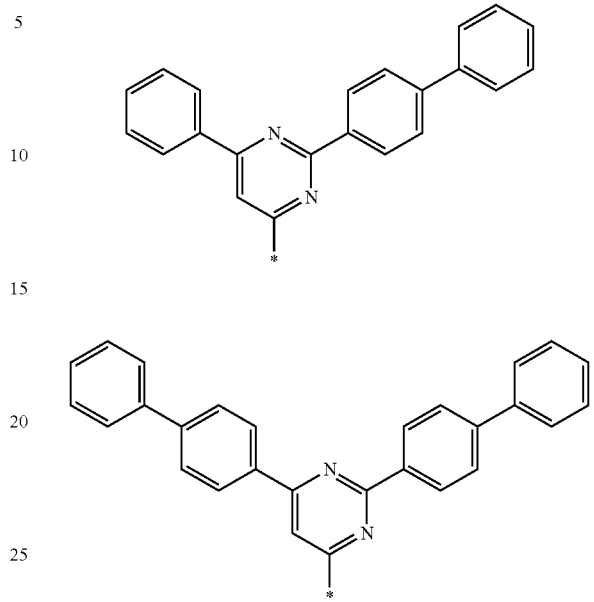
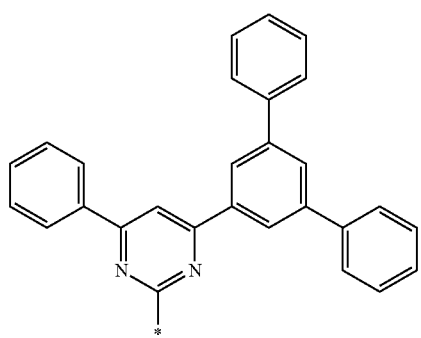
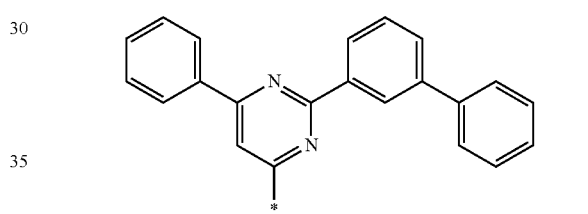
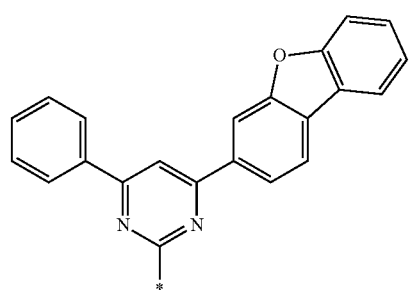
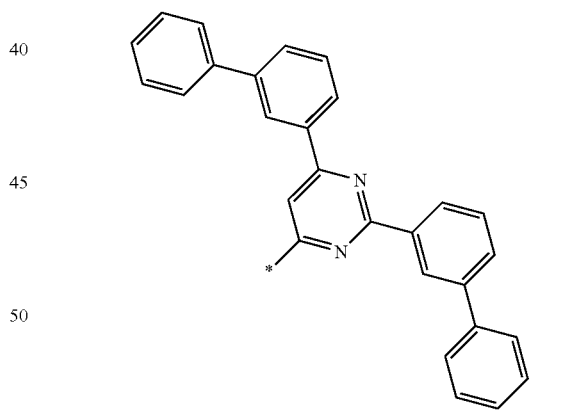
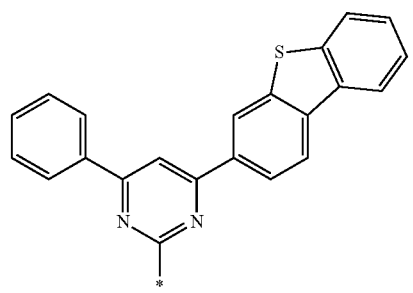
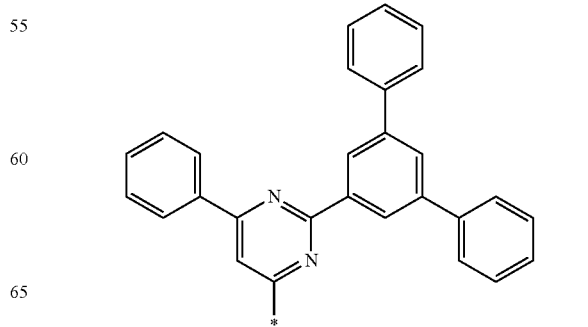
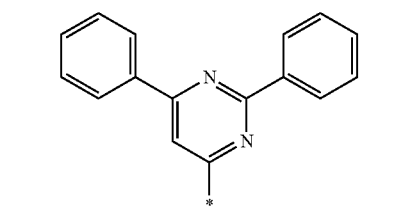

-continued
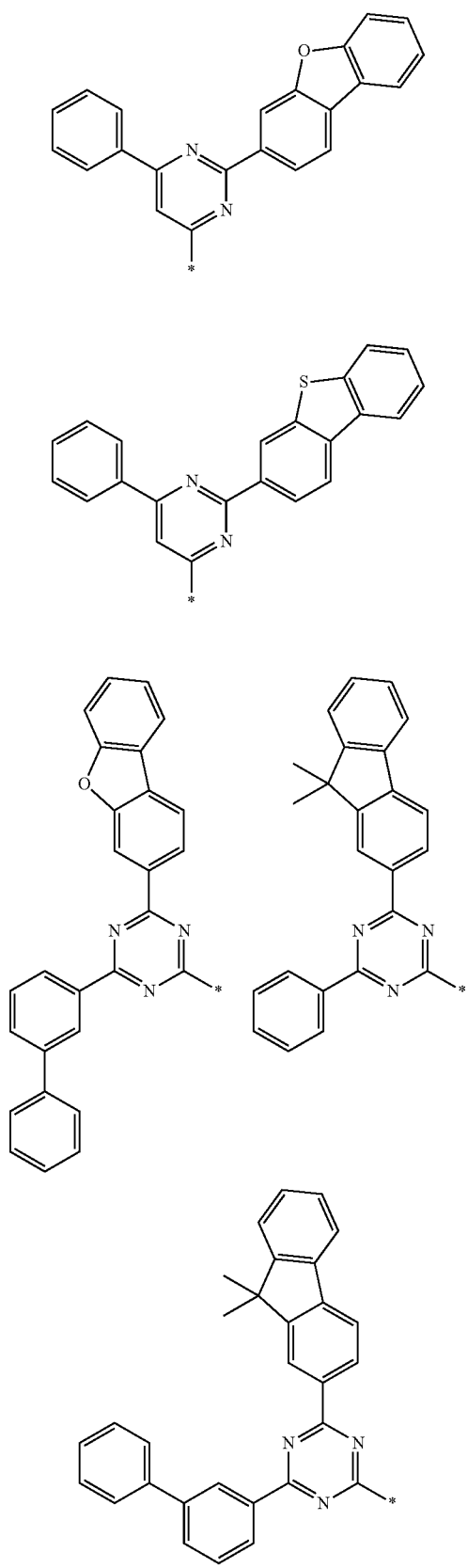
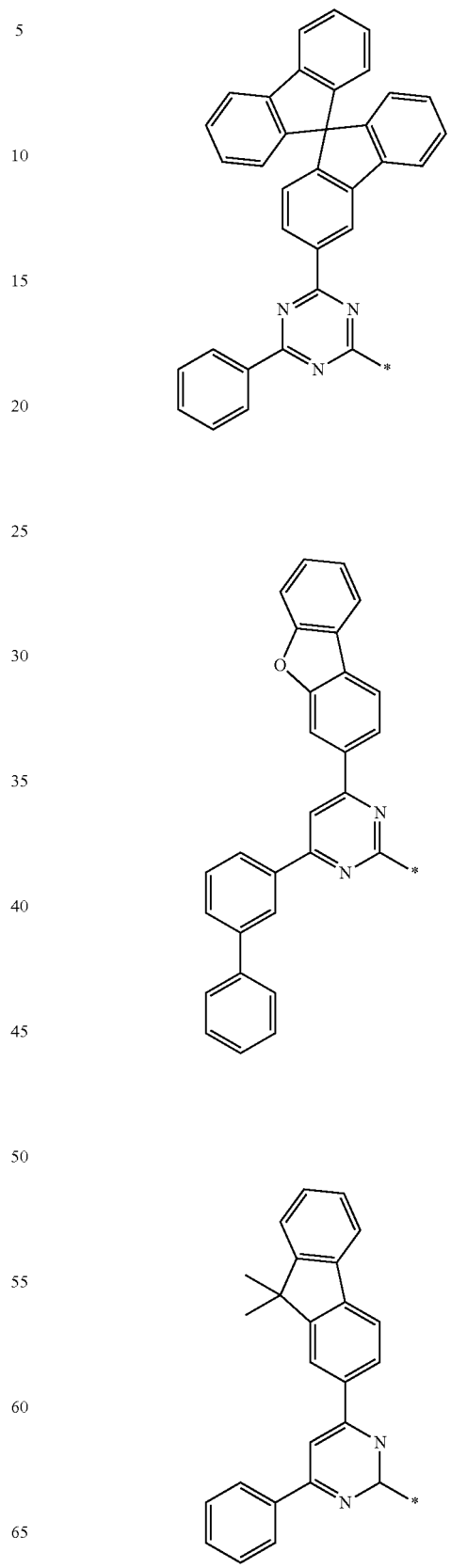

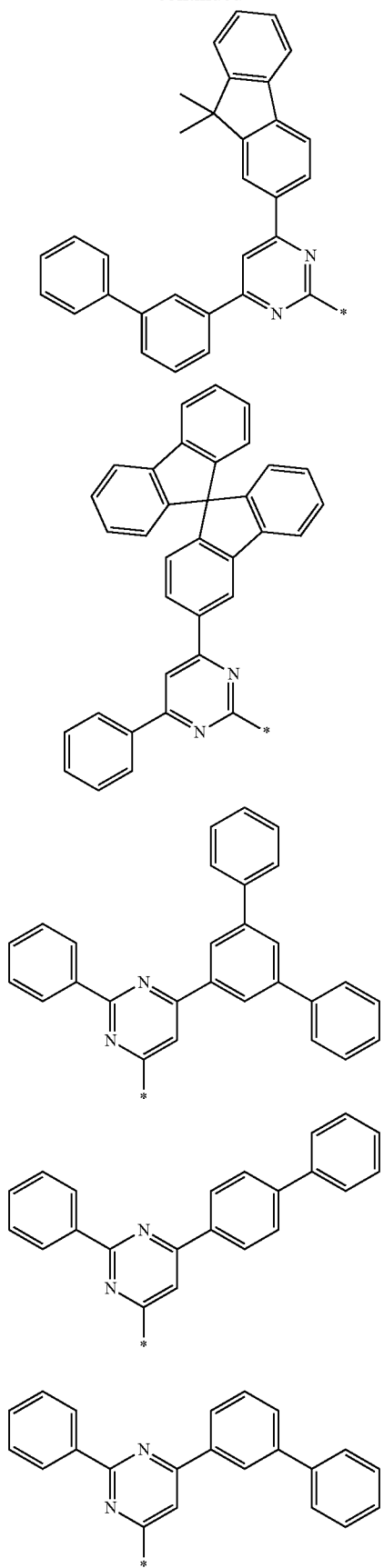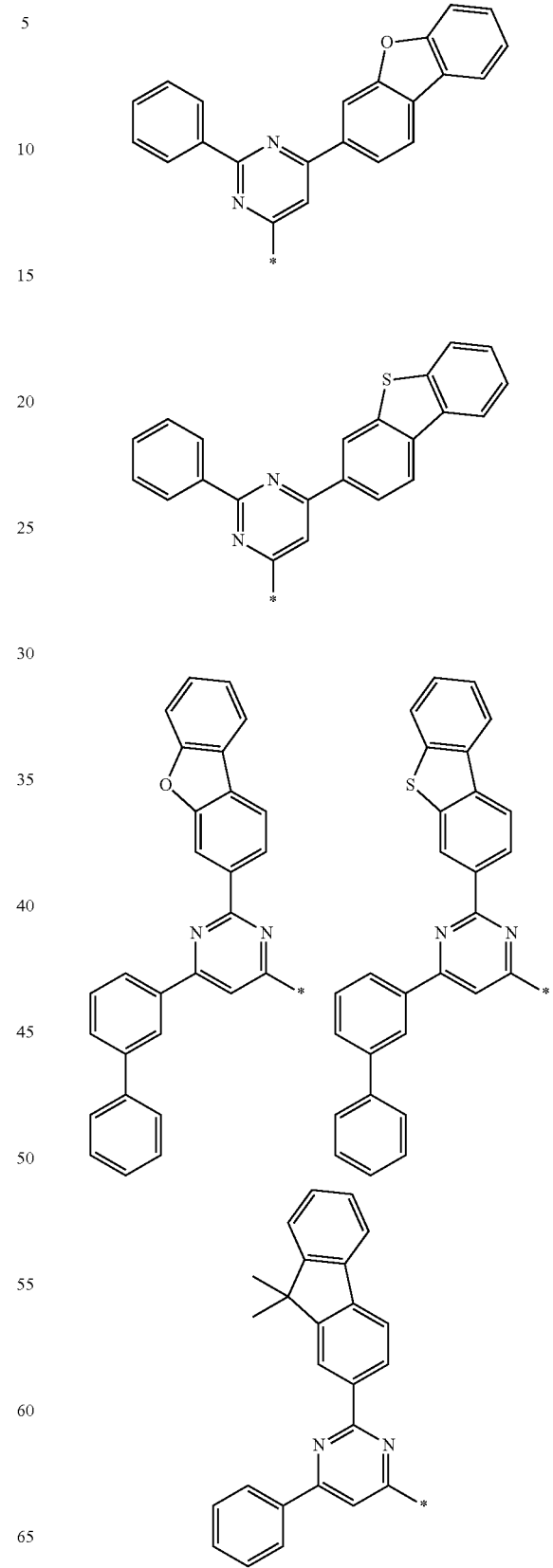

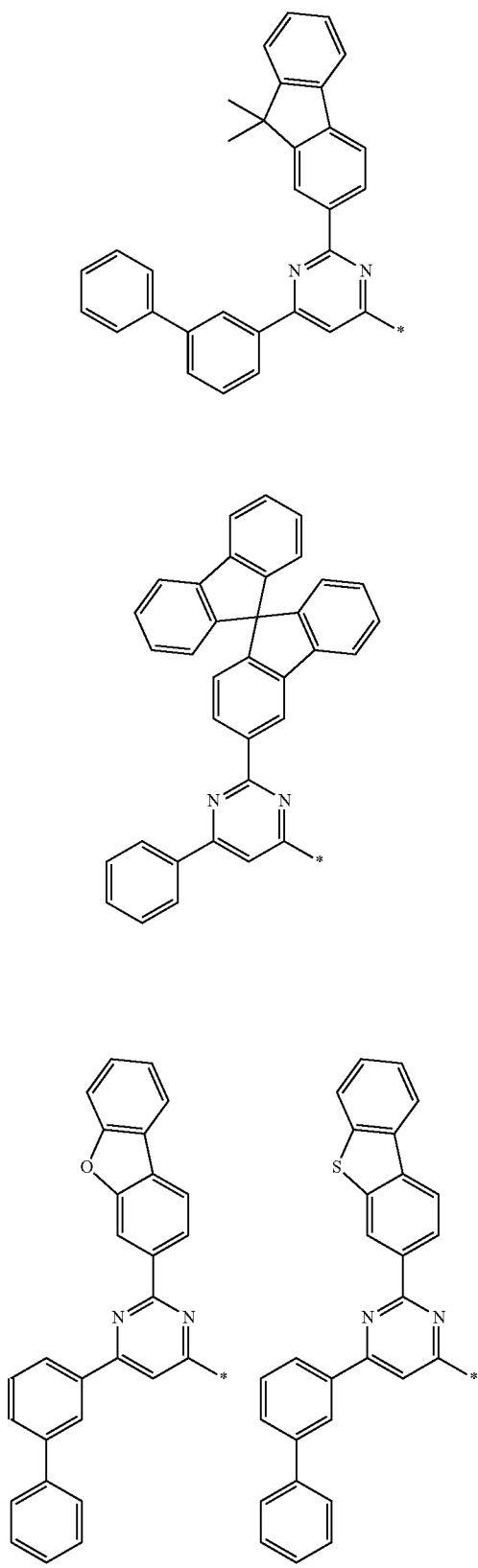
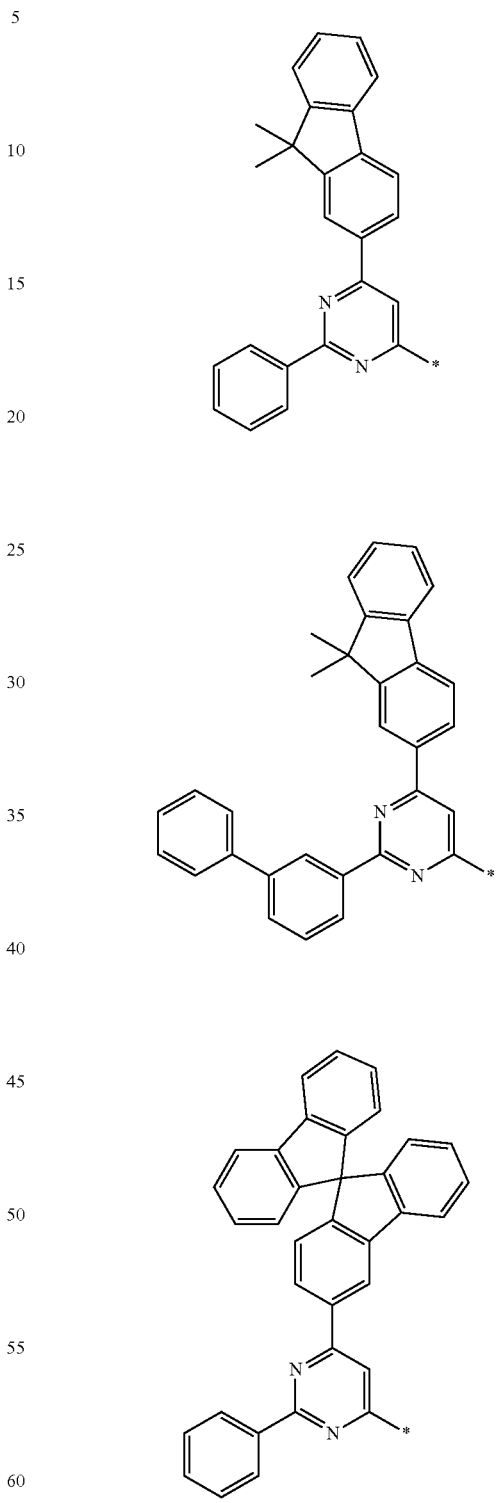
wherein, in Group I,
\* is a linking point with "L" of Chemical Formula 1.
4. The compound for an organic optoelectronic diode of claim 1, which is selected from compounds of Group 1:

[Group 1]
1
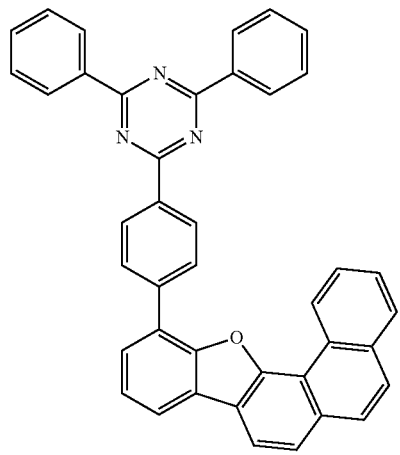
2
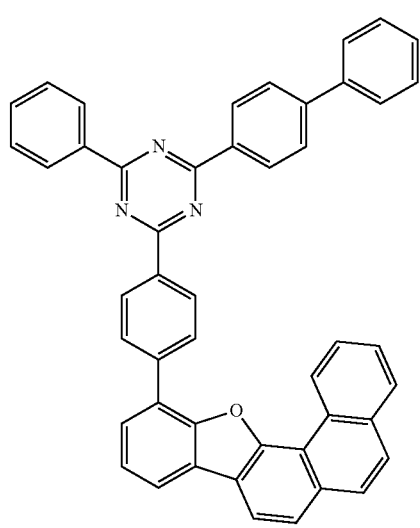
4
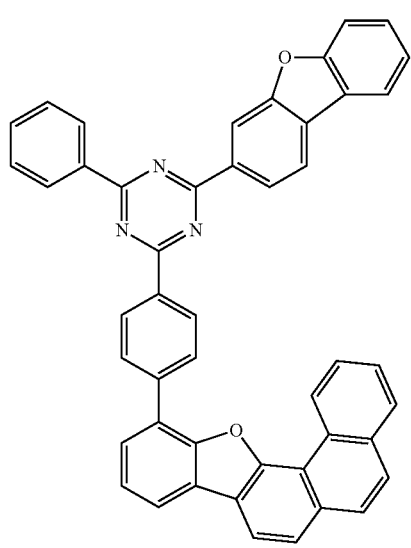
5
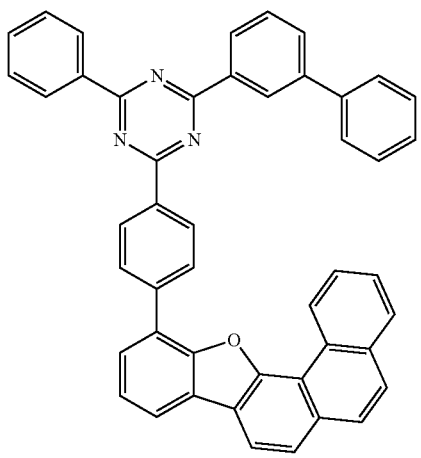
6
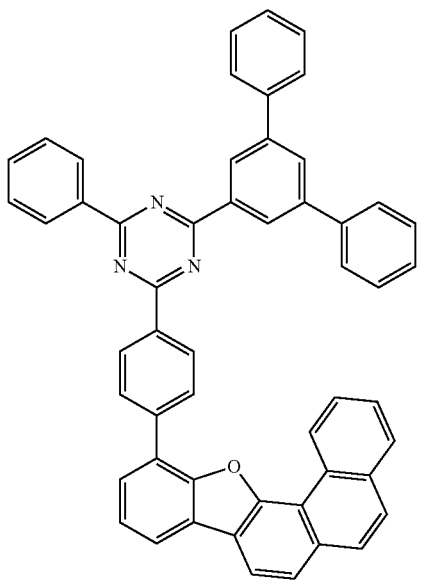
7
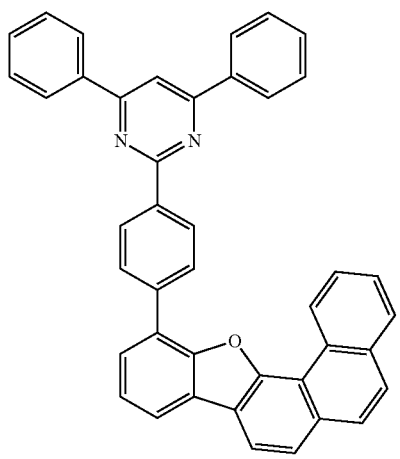

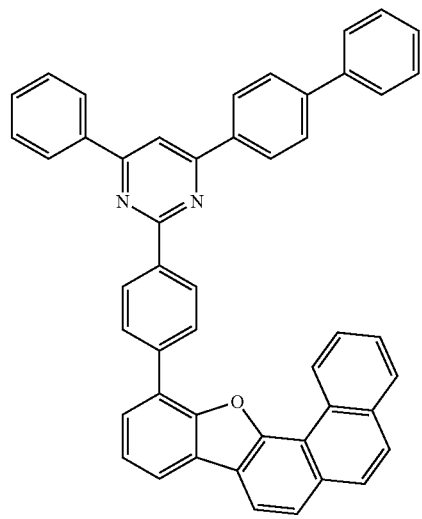
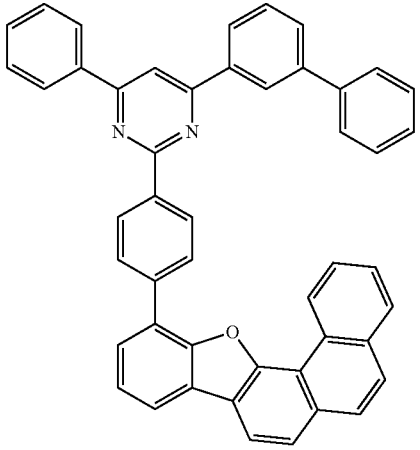
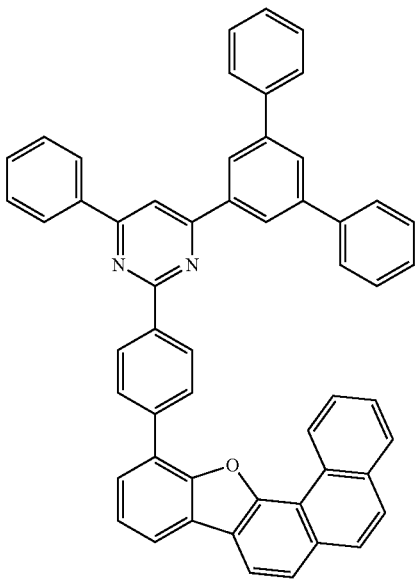
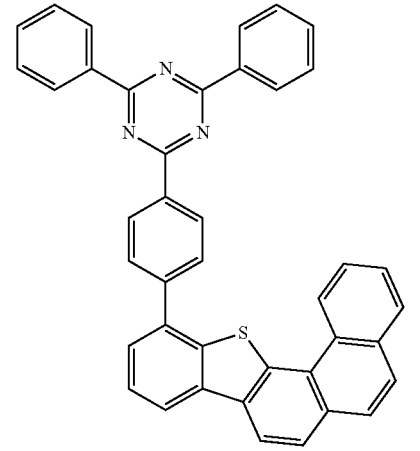

121
-continued
14
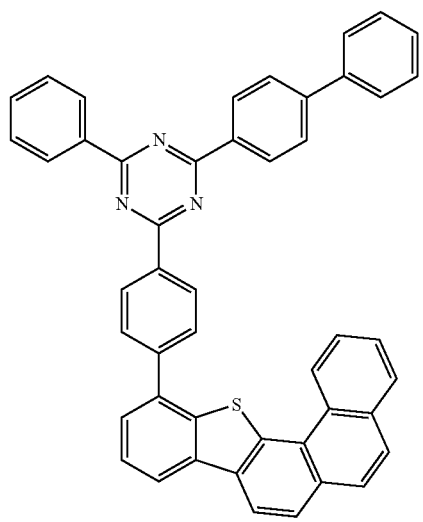
15
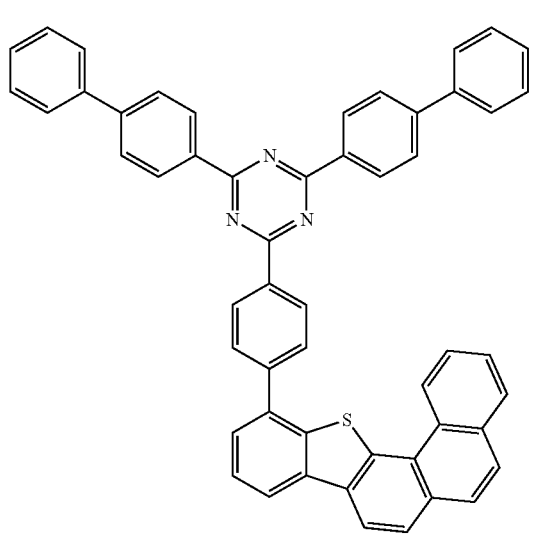
16
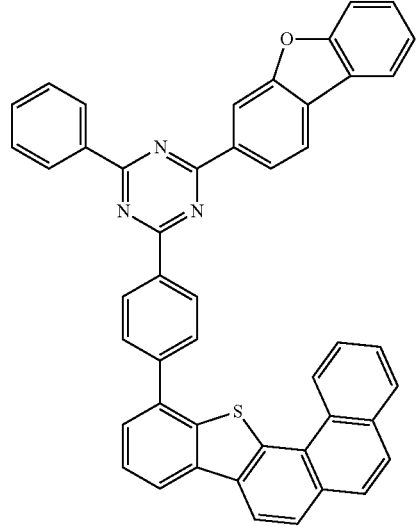
122
-continued
17
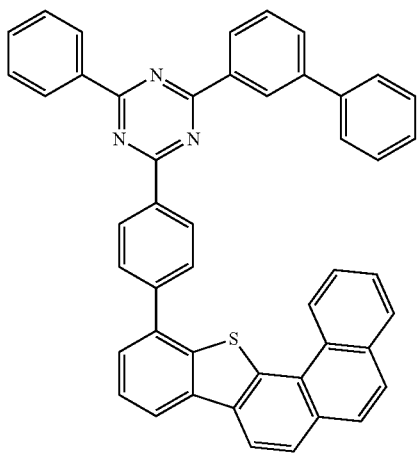
18
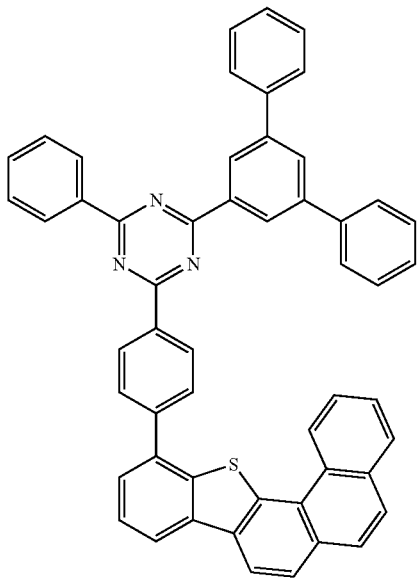
19
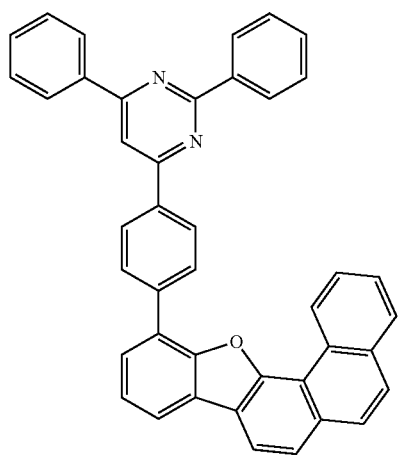

123
-continued
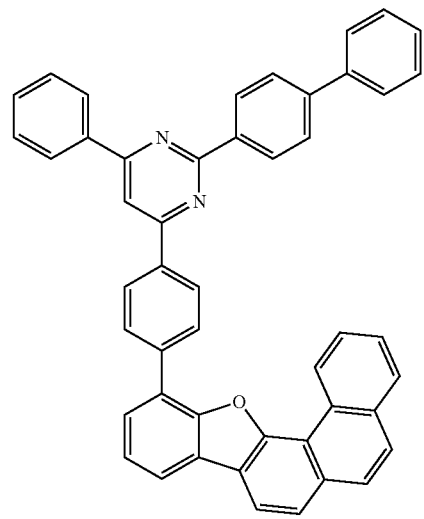
20
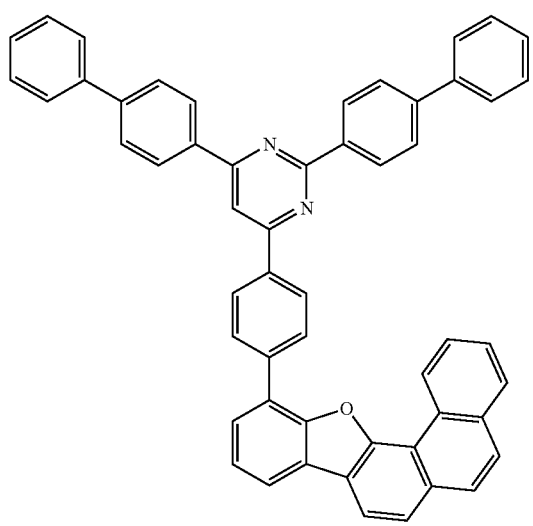
21
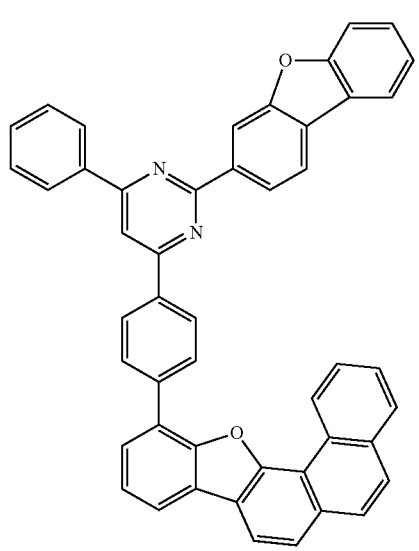
22
124
-continued
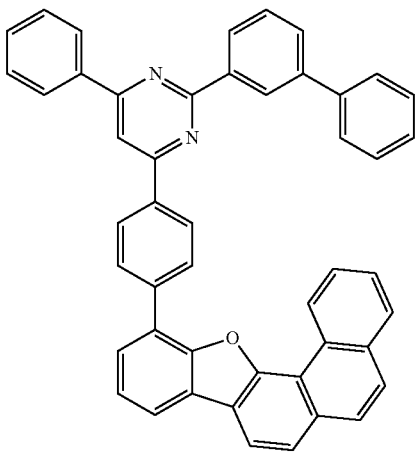
23
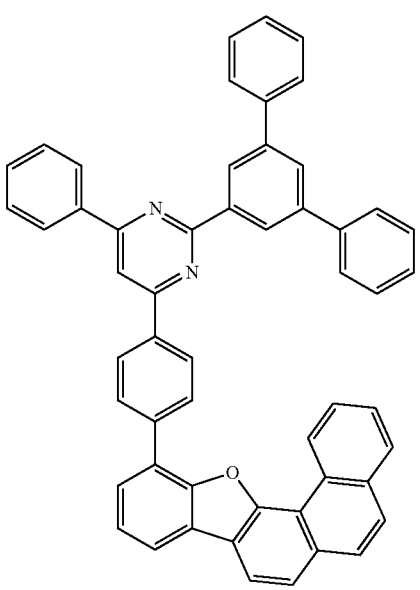
24
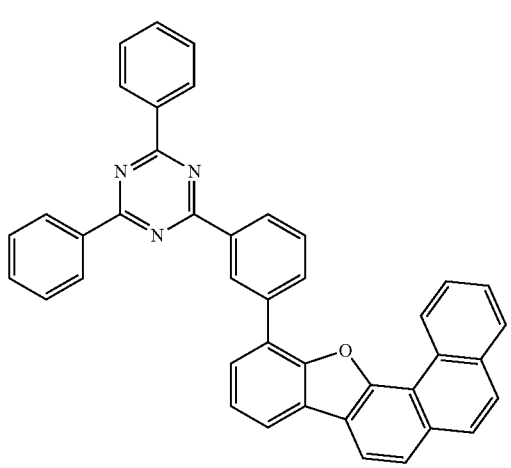
25

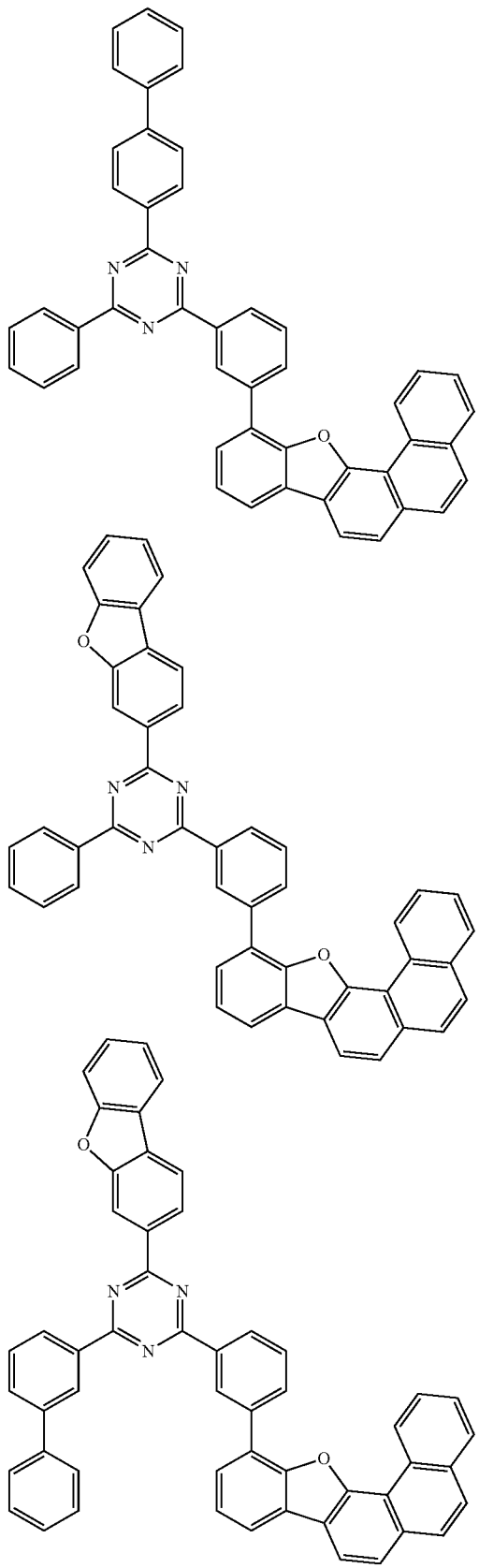
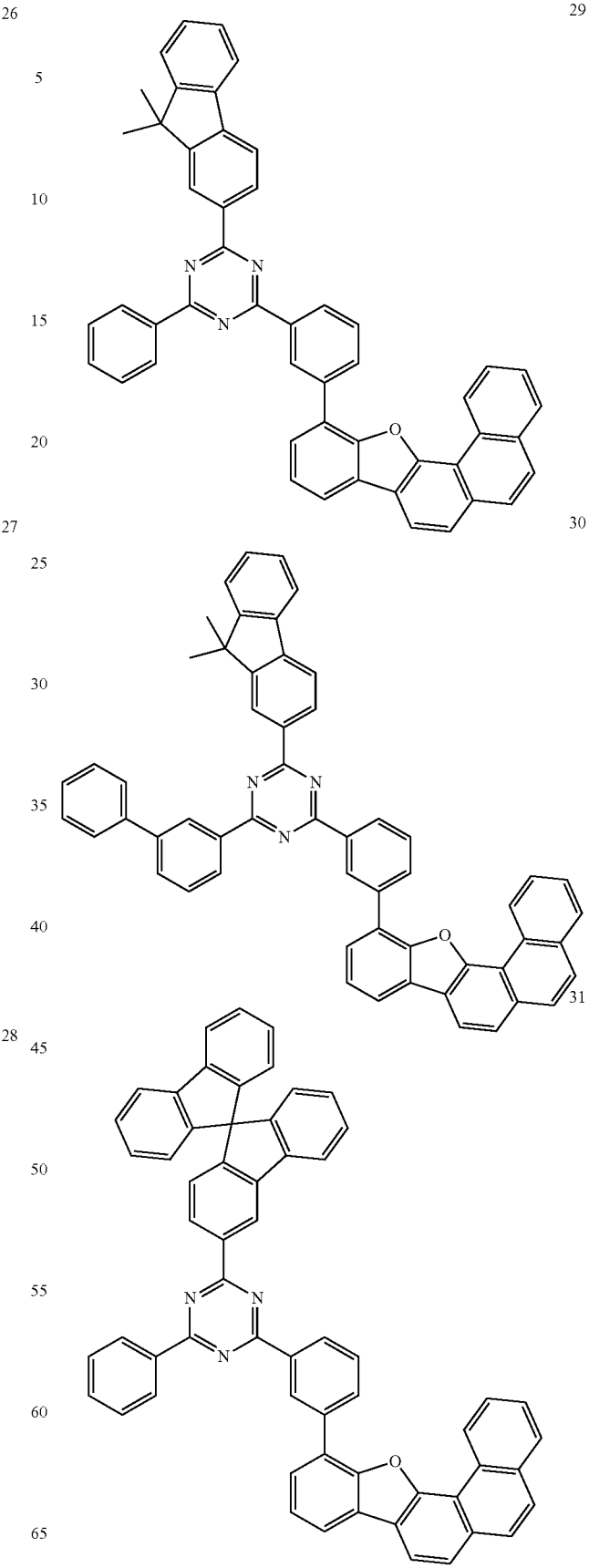

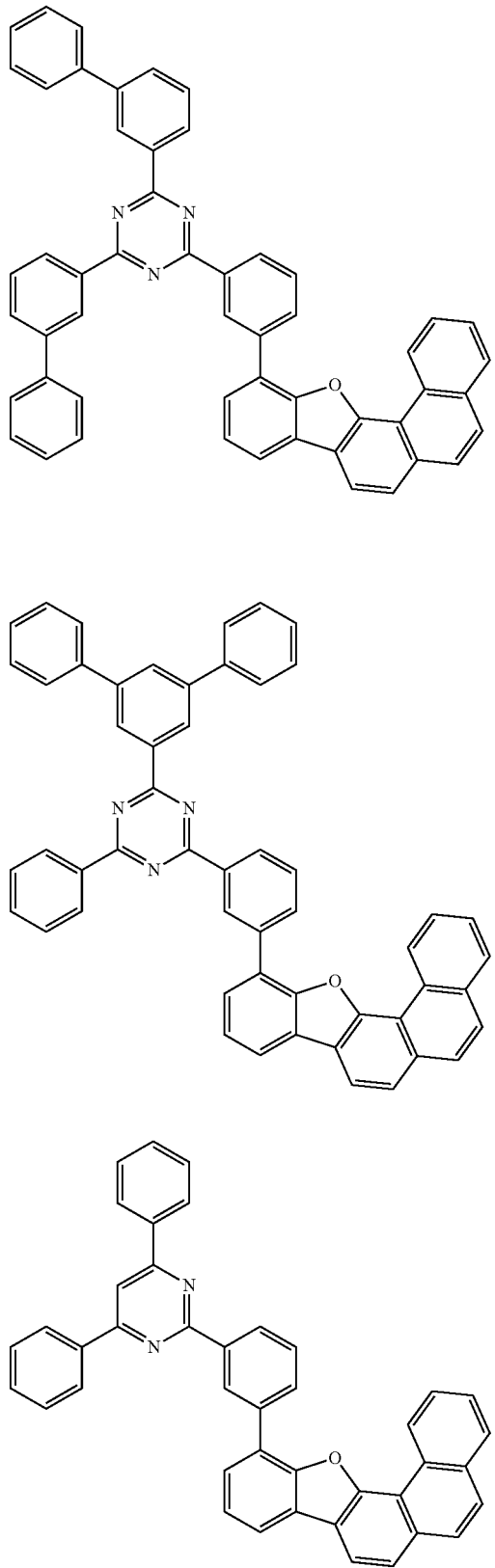
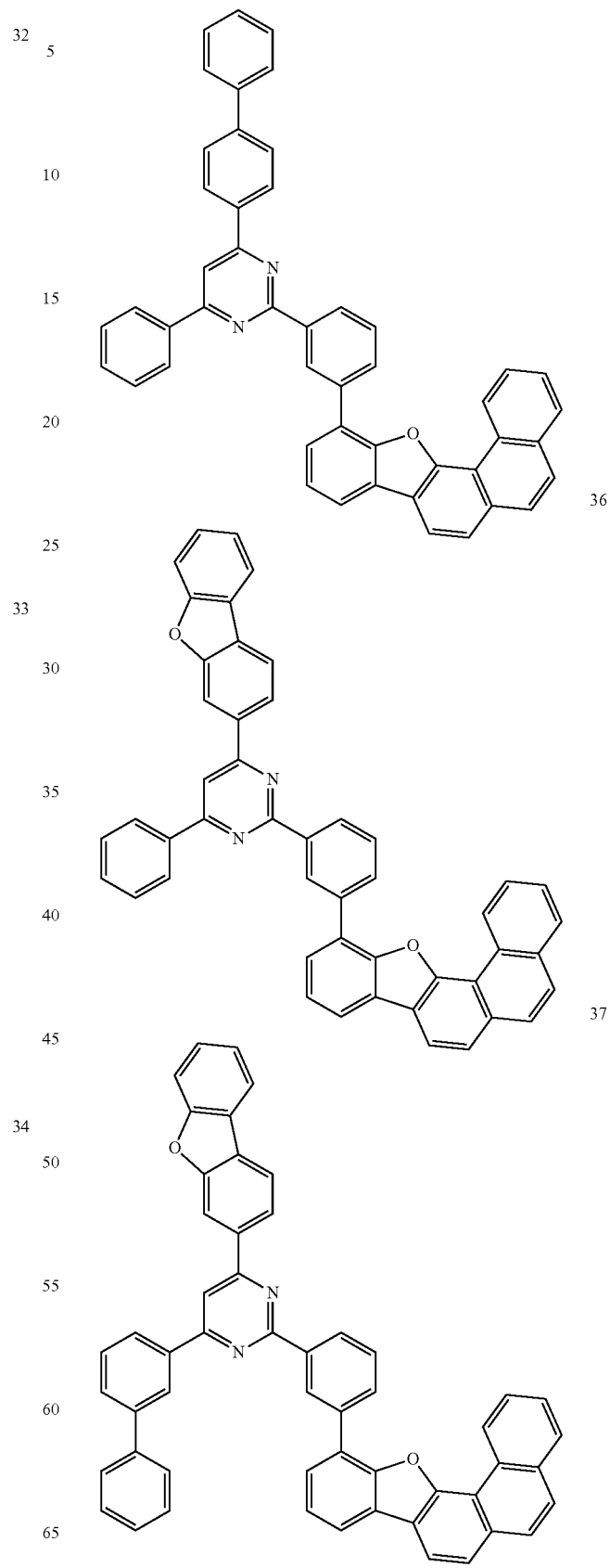

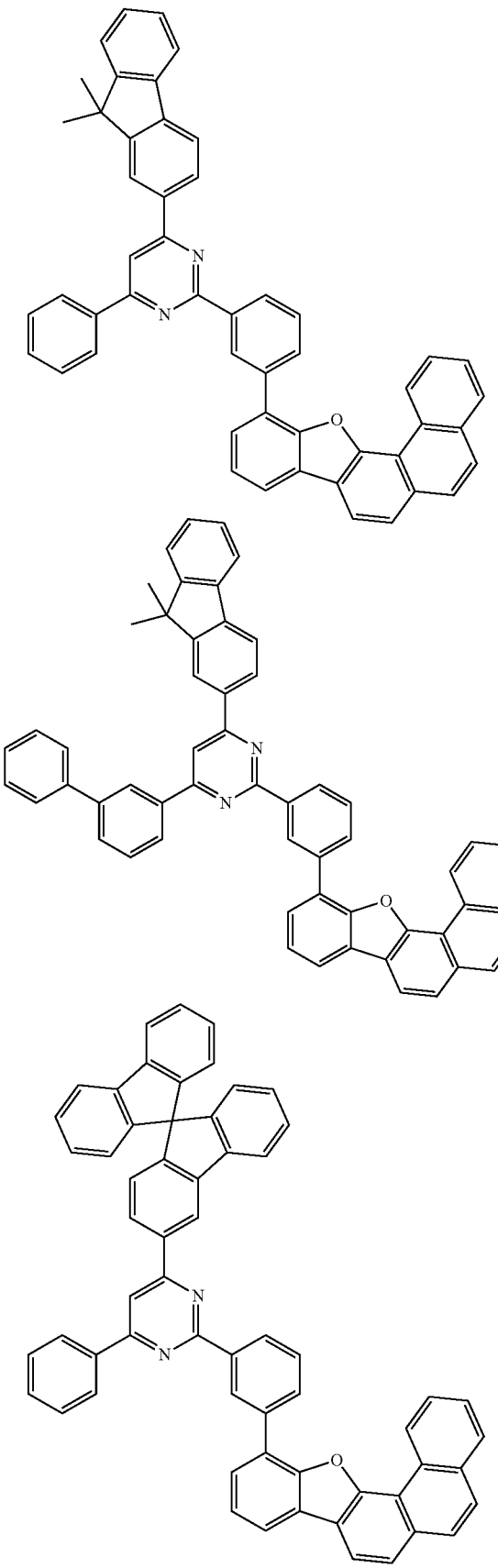
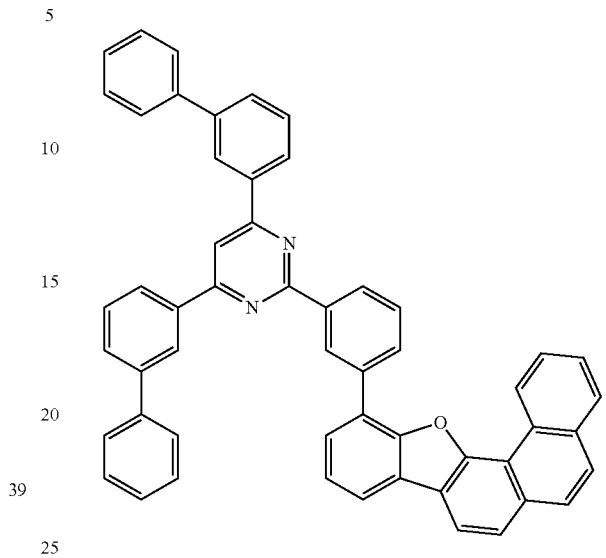
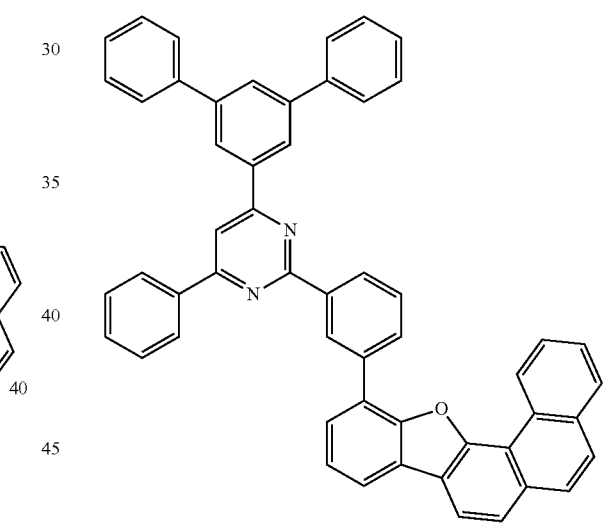
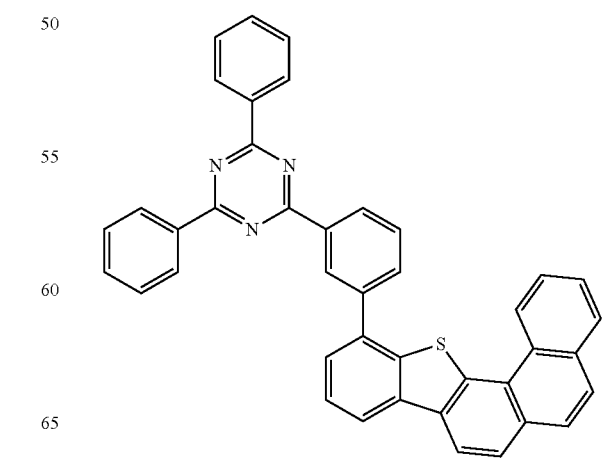

-continued
131
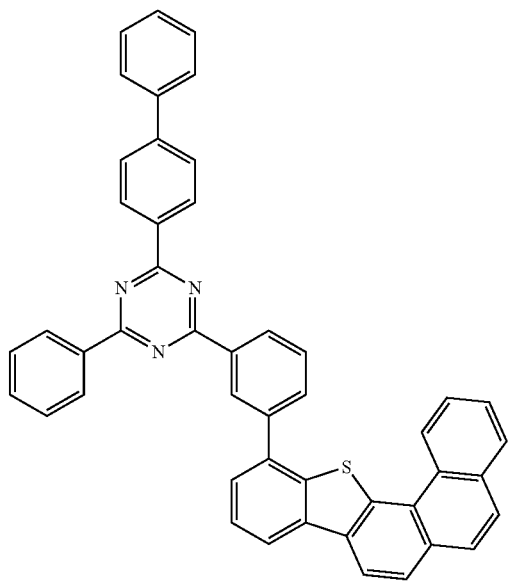
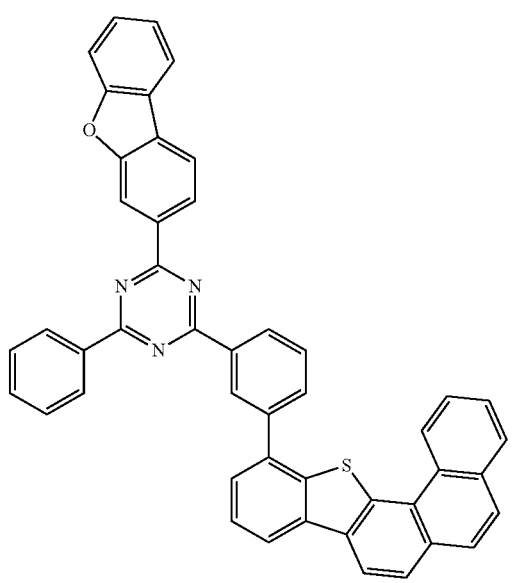
-continued
132
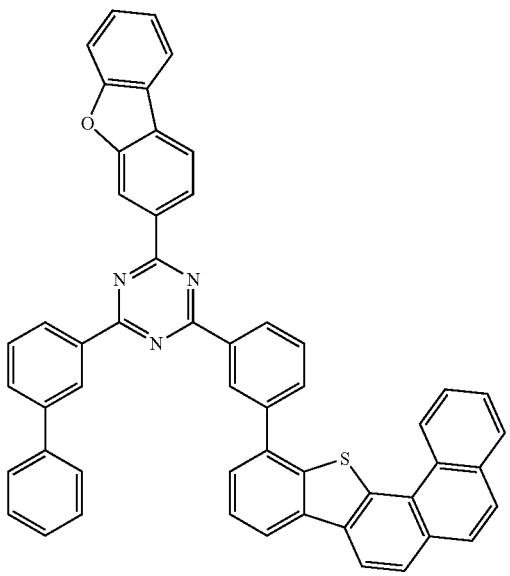
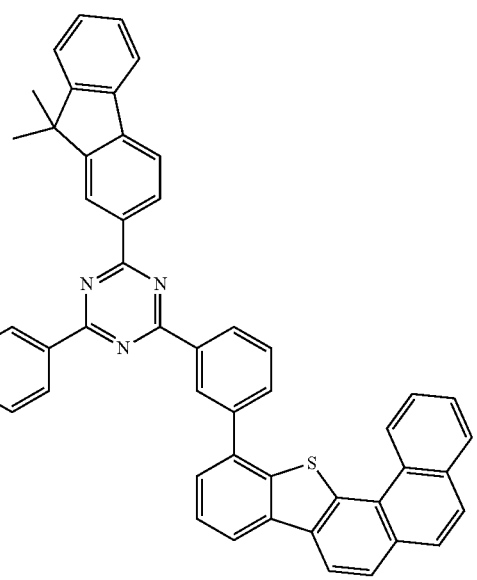

133
-continued

48

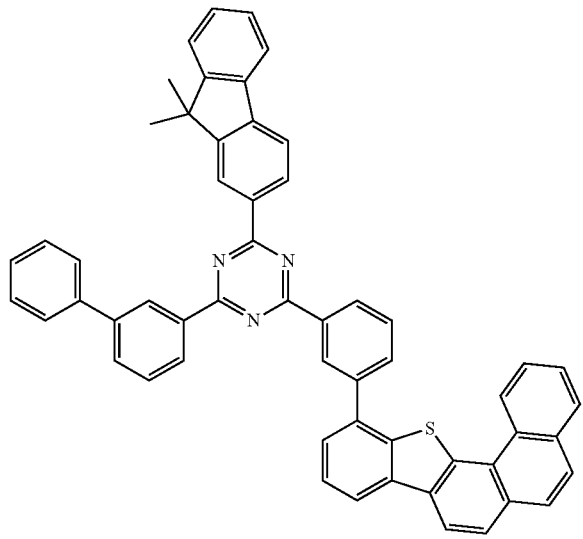

49

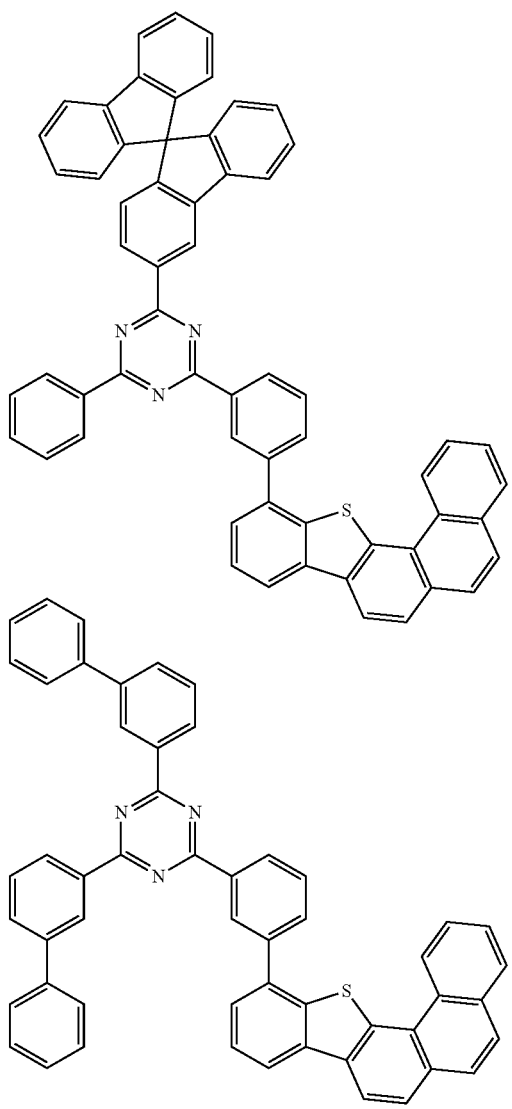

50

134
-continued

51

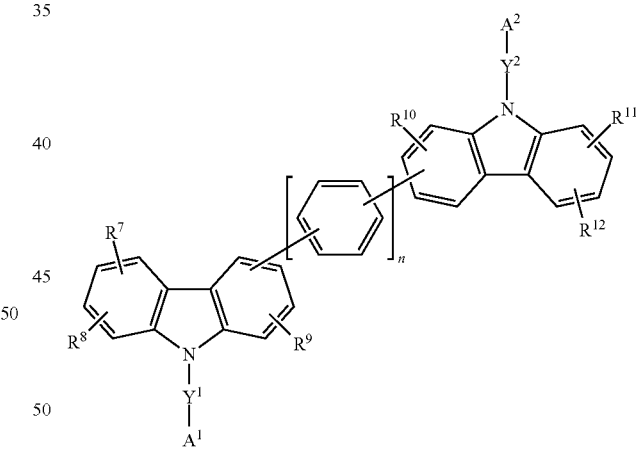

5. The compound for an organic optoelectronic diode of claim 1, wherein T1 energy is 2.55 eV to 2.65 eV.

6. A composition for an organic optoelectronic diode, comprising
the first compound for an organic optoelectronic diode of claim 1; and
a second compound for an organic optoelectronic diode represented by Chemical Formula 2:

[Chemical Formula 2]

wherein, in Chemical Formula 2,
$Y^1$ and $Y^2$ are independently a single bond, a substituted or unsubstituted C6 to C30 arylene group, a substituted or unsubstituted C2 to C30 heteroarylene group, or a combination thereof,
$A^1$ and $A^2$ are independently a substituted or unsubstituted C6 to C30 aryl group, a substituted or unsubstituted C2 to C30 heterocyclic group, or a combination thereof,
$R^7$ to $R^{12}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof,
n is one of integers of 0 to 2; and the "substituted" refers to replacement of at least one hydrogen by deuterium, a C1 to C4 alkyl group, a C6 to C18 aryl group, or a C2 to C30 heteroaryl group.

7. The composition for an organic optoelectronic diode of claim 6, wherein $A^1$ and $A^2$ of Chemical Formula 2 are independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted dibenzofuranyl group, a substituted or unsubstituted dibenzothiophenyl group, a substituted or unsubstituted carbazolyl group, a substituted or unsubstituted fluorenyl group, or a combination thereof.

8. The composition for an organic optoelectronic diode of claim 6, wherein

Chemical Formula 2 includes a moiety of Group II, and moieties *—$Y^1$-$A^1$ and *—$Y^2$-$A^2$ of Chemical Formula 2 are each independently a moiety of Group III:

[Group II]

C-1
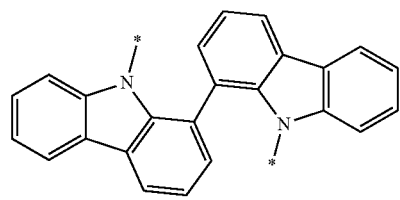

C-2
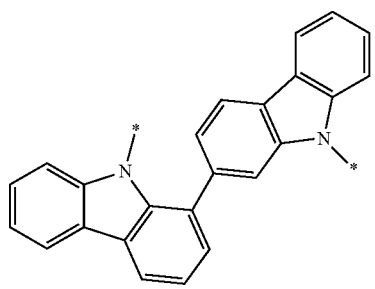

C-3
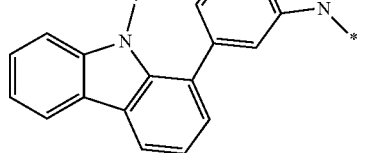

C-4
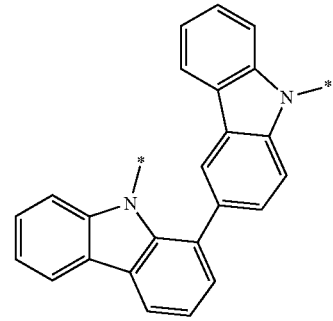

C-5
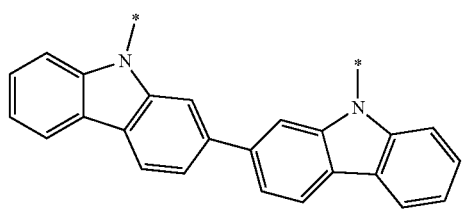

C-6
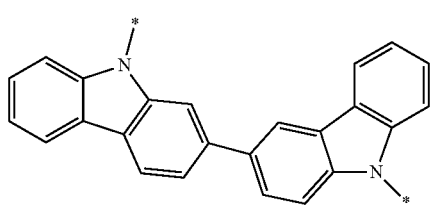

C-7
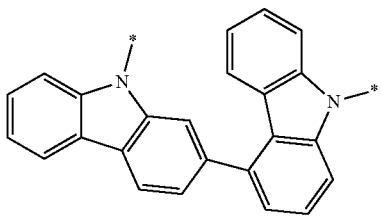

C-8
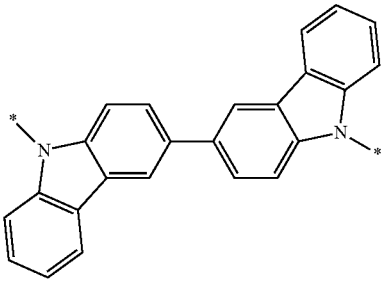

C-9
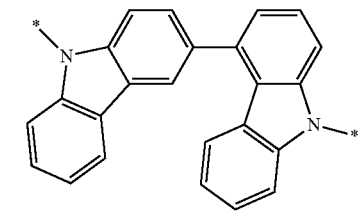

C-10
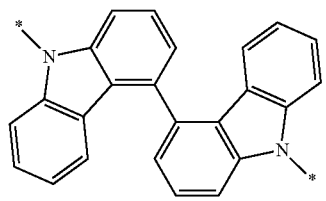

C-11
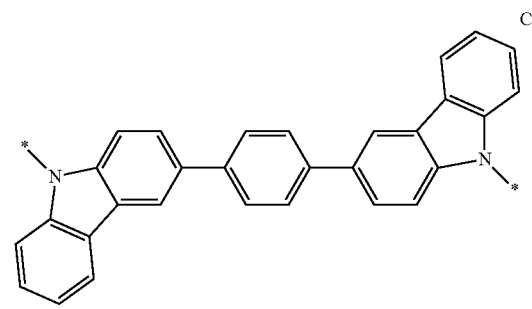
C-12
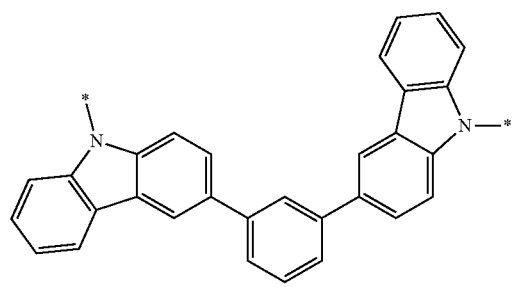
C-13
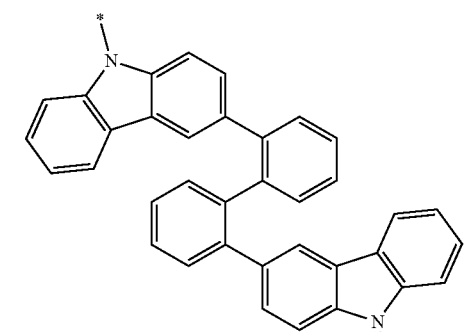
C-14
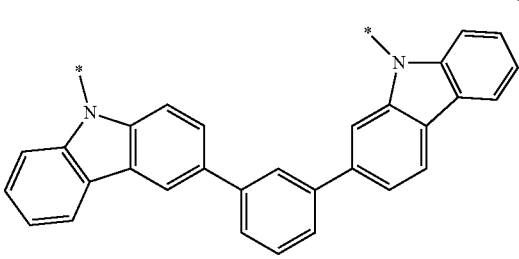
C-15
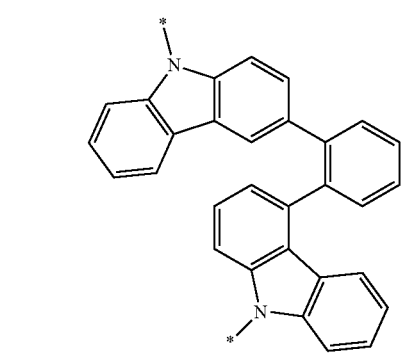
C-16
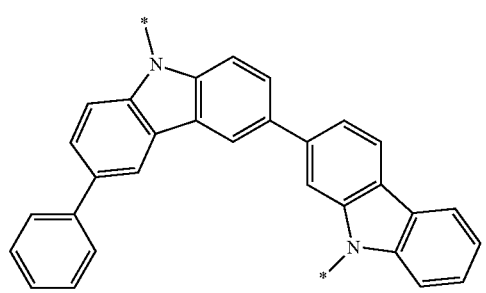
C-17
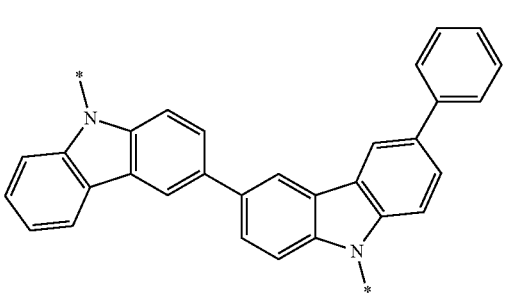
C-18
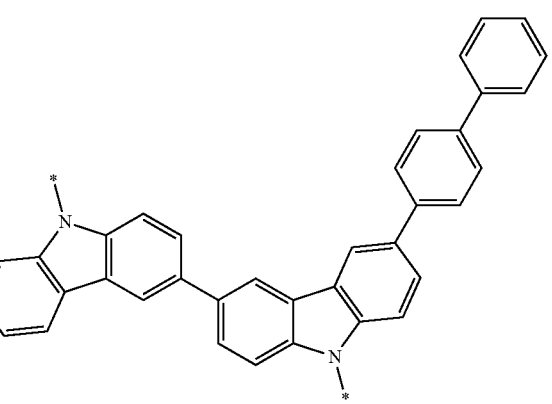
[Group III]
B-1
B-2
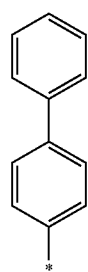

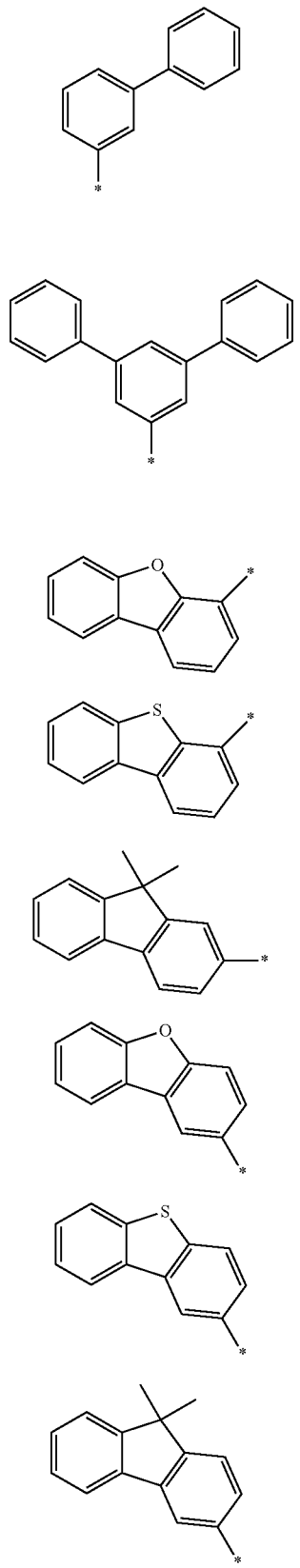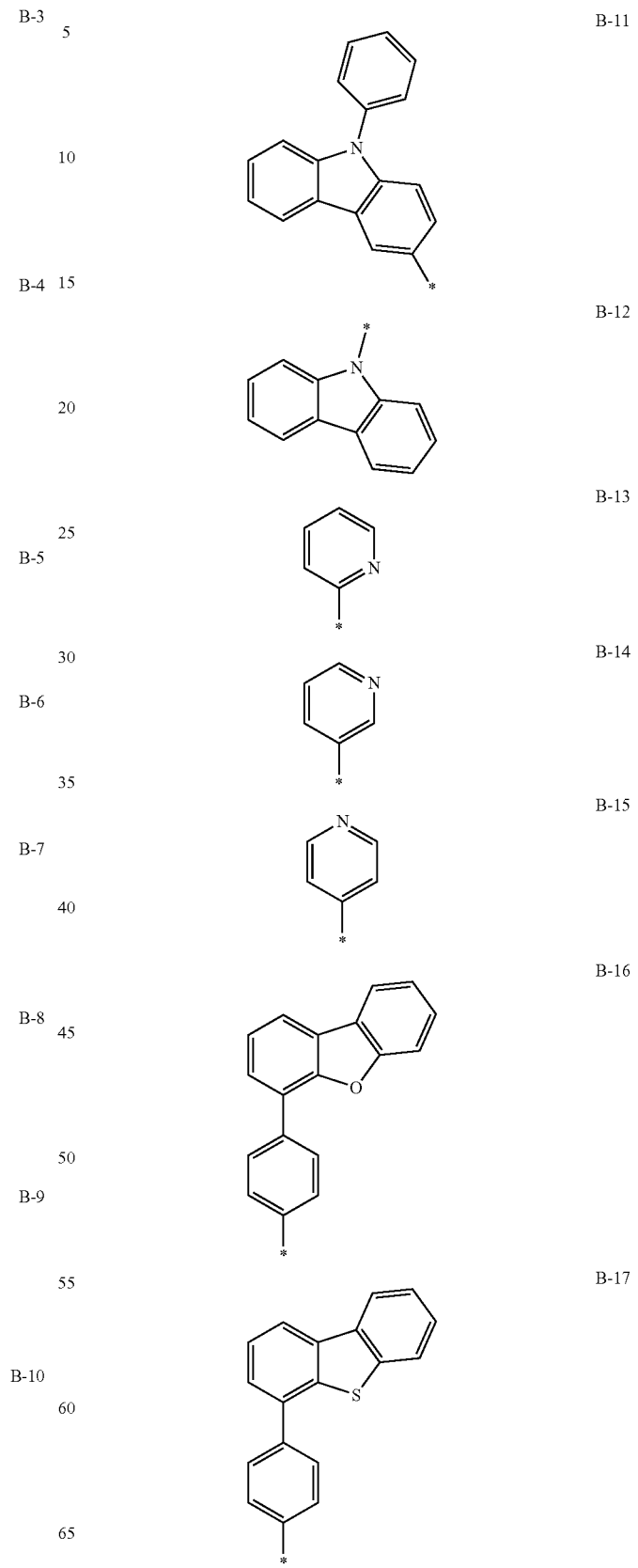

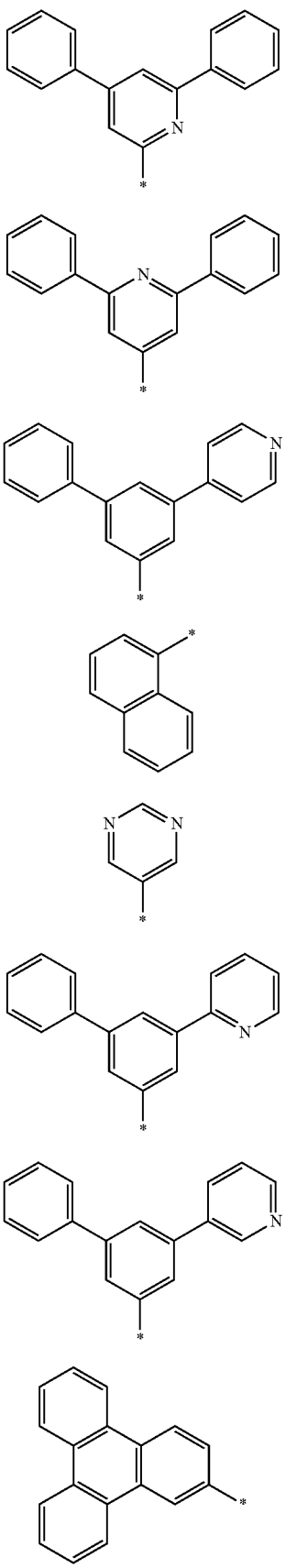

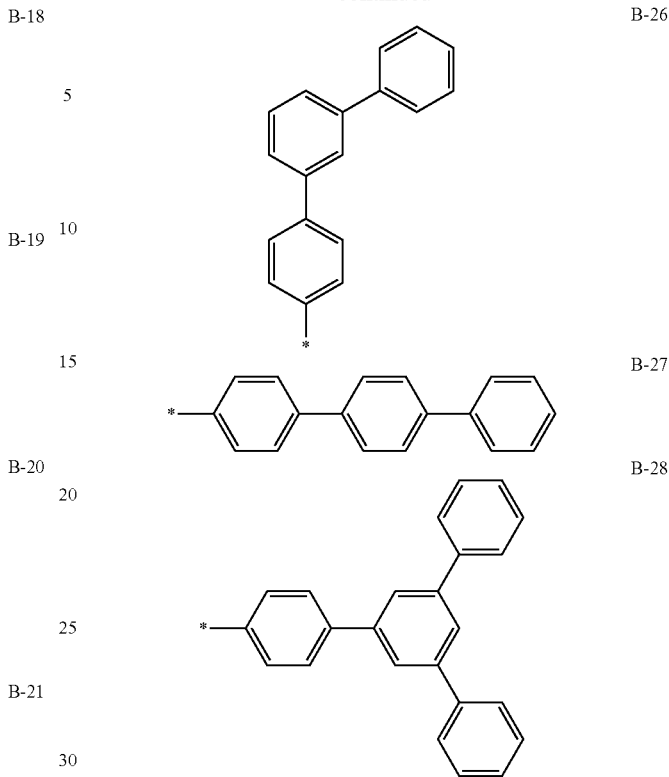

wherein, in Groups II and III, * is a linking point.

9. The composition for an organic optoelectronic diode of claim 8, wherein
Chemical Formula 2 includes a moiety represented by Chemical Formula C-8 or Chemical Formula C-17 of Group II, and
moieties *—$Y^1$-$A^1$ and *—$Y^2$-$A^2$ are each independently a moiety represented by B-1, B-2, or B-3 of Group III.

10. An organic optoelectronic diode comprising
an anode and a cathode facing each other, and
at least one organic layer disposed between the anode and the cathode,
wherein the organic layer comprises the compound for an organic optoelectronic diode of claim 1.

11. The organic optoelectronic diode of claim 10, wherein the organic layer comprises a light emitting layer, and
the compound for an organic optoelectronic diode or the composition for an organic optoelectronic diode is included as a host of the light emitting layer.

12. The organic optoelectronic diode of claim 10, wherein a maximum light emitting wavelength is 500 nm to 550 nm.

13. A display apparatus comprising the organic optoelectronic diode of claim 10.

14. An organic optoelectronic diode comprising
an anode and a cathode facing each other, and
at least one organic layer disposed between the anode and the cathode,
wherein the organic layer comprises the composition for an organic optoelectronic diode of claim 6.

15. The organic optoelectronic diode of claim 14, wherein the organic layer comprises a light emitting layer, and
the compound for an organic optoelectronic diode or the composition for an organic optoelectronic diode is included as a host of the light emitting layer.

16. The organic optoelectronic diode of claim 14, wherein a maximum light emitting wavelength is 500 nm to 550 nm.

17. A display apparatus comprising the organic optoelectronic diode of claim 14.

* * * * *